United States Patent
Pai et al.

(10) Patent No.: US 7,144,363 B2
(45) Date of Patent: Dec. 5, 2006

(54) SYSTEMS FOR HEART TREATMENT

(75) Inventors: Suresh Pai, Mountain View, CA (US); Nicanor Domingo, Brisbane, CA (US); James G. Whayne, Chapel Hill, NC (US)

(73) Assignee: Extensia Medical, Inc., Mountain View, CA (US)

( * ) Notice: Subject to any disclaimer, the term of this patent is extended or adjusted under 35 U.S.C. 154(b) by 590 days.

(21) Appl. No.: 10/269,844

(22) Filed: Oct. 11, 2002

(65) Prior Publication Data

US 2003/0078465 A1 Apr. 24, 2003

Related U.S. Application Data

(60) Provisional application No. 60/368,918, filed on Mar. 29, 2002, provisional application No. 60/329,694, filed on Oct. 16, 2001.

(51) Int. Cl.
*A61N 1/362* (2006.01)
(52) U.S. Cl. .......................................... 600/16; 600/37
(58) Field of Classification Search ........ 606/151–158; 600/16–17, 37; 623/1.1; 128/898
See application file for complete search history.

(56) References Cited

U.S. PATENT DOCUMENTS

| | | | |
|---|---|---|---|
| 6,629,921 B1 * | 10/2003 | Schweich et al. | 600/16 |
| 6,723,038 B1 * | 4/2004 | Schroeder et al. | 600/16 |
| 6,793,618 B1 * | 9/2004 | Schweich et al. | 600/37 |
| 2002/0087173 A1 | 7/2002 | Alferness et al. | |
| 2002/0169502 A1 | 11/2002 | Mathis | |
| 2002/0169504 A1 | 11/2002 | Alferness et al. | |
| 2003/0078465 A1 | 4/2003 | Pai et al. | |
| 2003/0083538 A1 | 5/2003 | Adams et al. | |
| 2003/0105520 A1 | 6/2003 | Alferness et al. | |
| 2003/0130731 A1 | 7/2003 | Vidlund et al. | |

OTHER PUBLICATIONS

Baim, Donald S. "Percutaneous Treatment of Mitral Regurgitation," Brigham and Women's Hospital, Harvard Medical School, Boston MA, Published at www.tctmd.com, Sep. 17, 2003.
Liel-Cohen et al. "Design of a New Surgical Approach for Ventricular Remodeling to Relieve Ischemic Mitral Regurgitation," Circulation, 2000;101:2756-2763.
Hung et al. "Reverse Ventricular Remodeling Reduces Ischemic Mitral Regurgitation," Circulation, 2002;106:2594-2600.

* cited by examiner

*Primary Examiner*—Mark Bockelman
(74) *Attorney, Agent, or Firm*—Patent Law Office of Frank P. Becking

(57) ABSTRACT

Described are devices and methods for treating degenerative, congestive heart disease and related valvular dysfunction. Percutaneous and minimally invasive surgical tensioning structures offer devices that mitigate changes in the ventricular structure (i.e., remodeling) and deterioration of global left ventricular performance related to tissue damage precipitating from ischemia, acute myocardial infarction (AMI) or other abnormalities. These tensioning structures can be implanted within various major coronary blood-carrying conduit structures (arteries, veins and branching vessels), into or through myocardium, or into engagement with other anatomic structures that impact cardiac output to provide tensile support to the heart muscle wall which resists diastolic filling pressure while simultaneously providing a compressive force to the muscle wall to limit, compensate or provide therapeutic treatment for congestive heart failure and/or to reverse the remodeling that produces an enlarged heart.

10 Claims, 54 Drawing Sheets

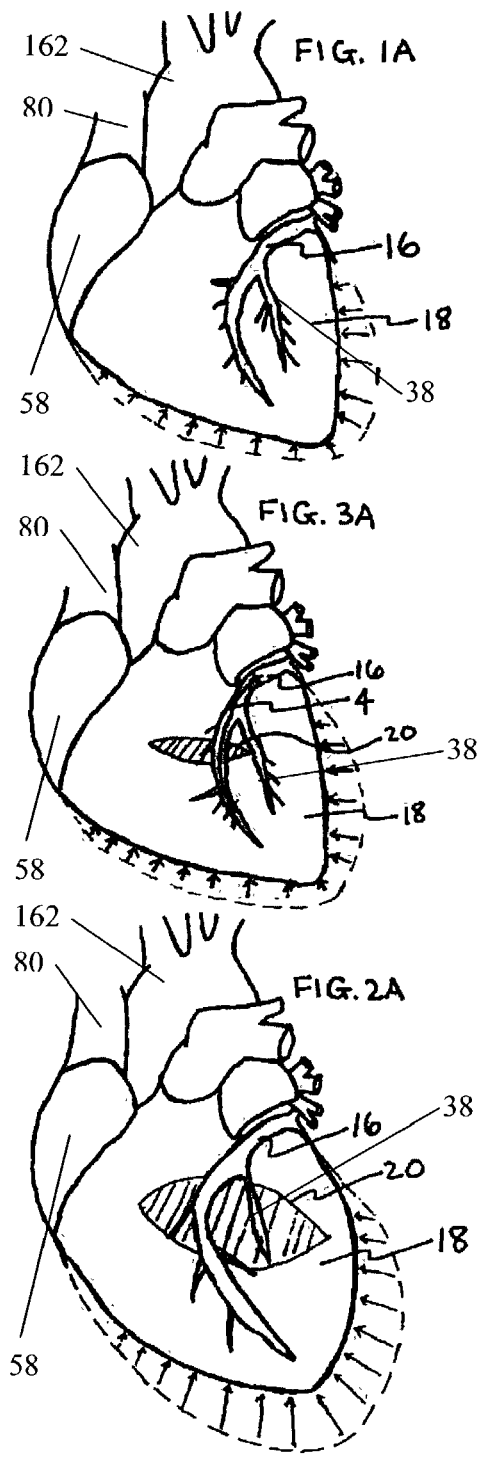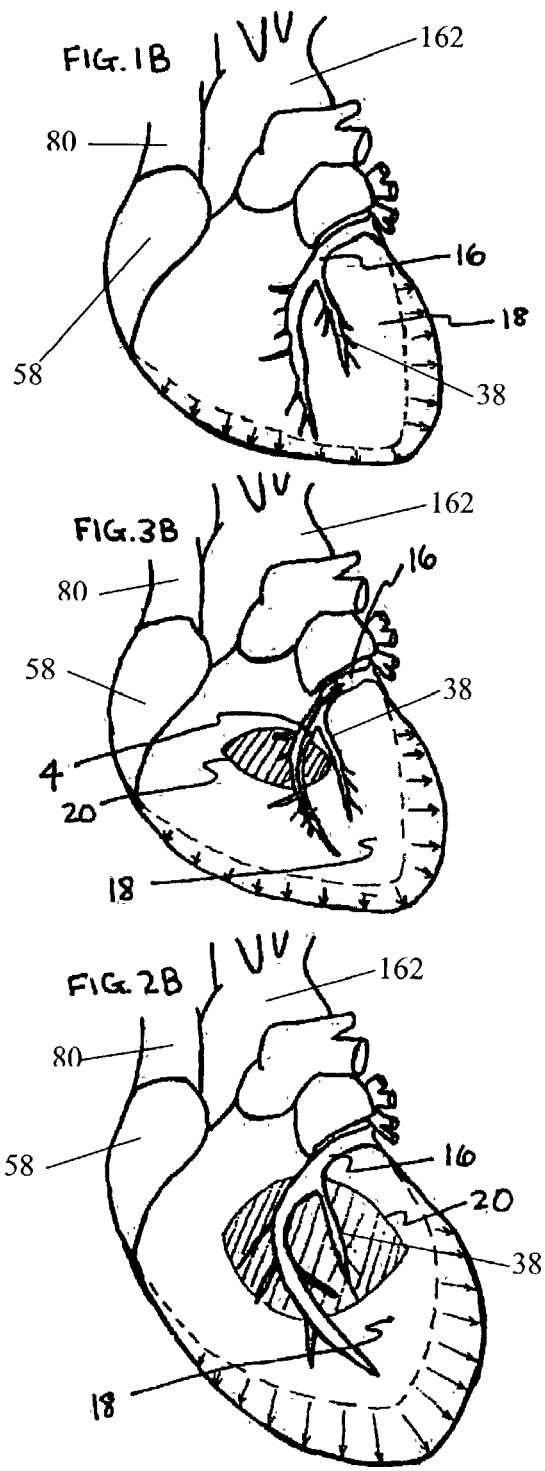

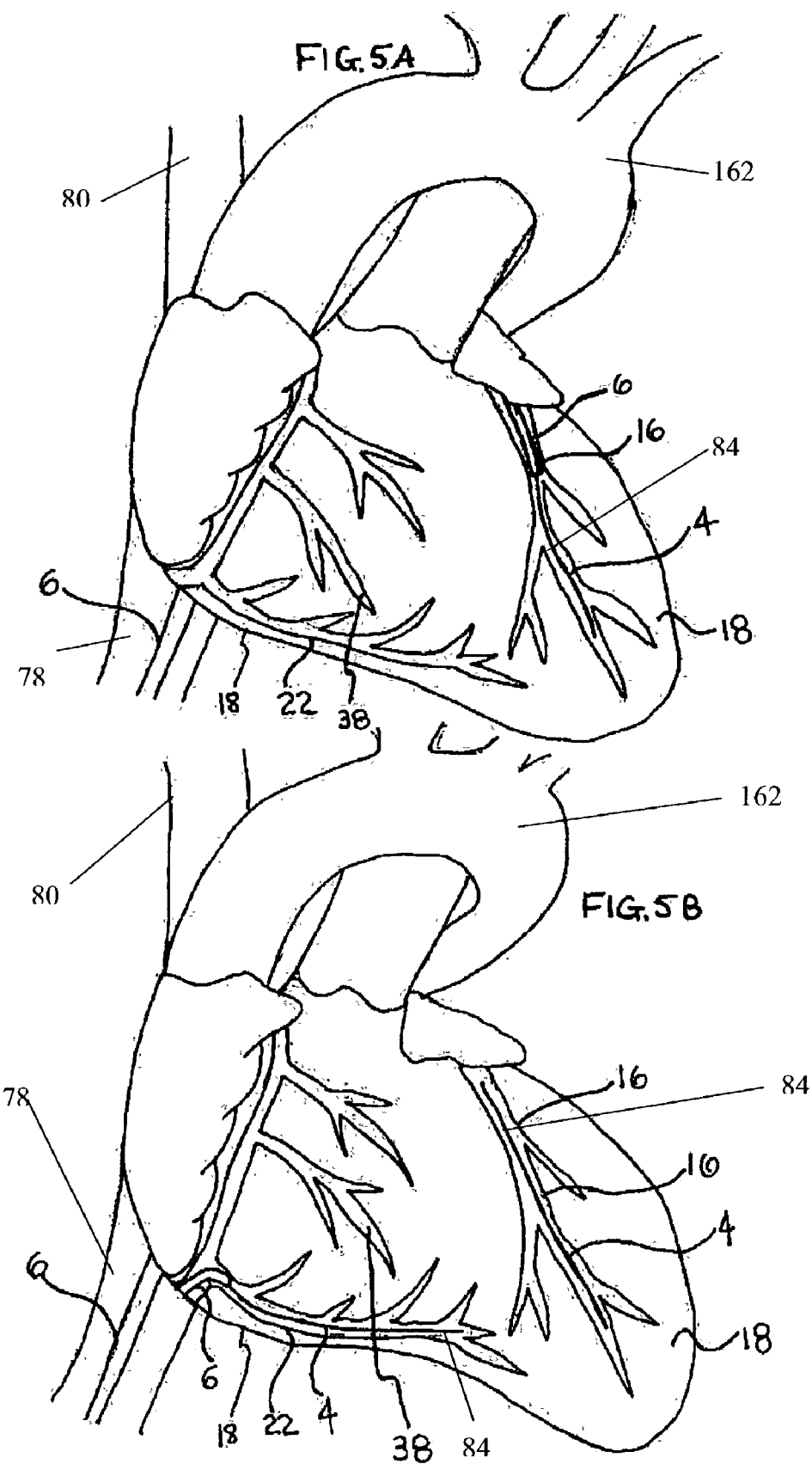

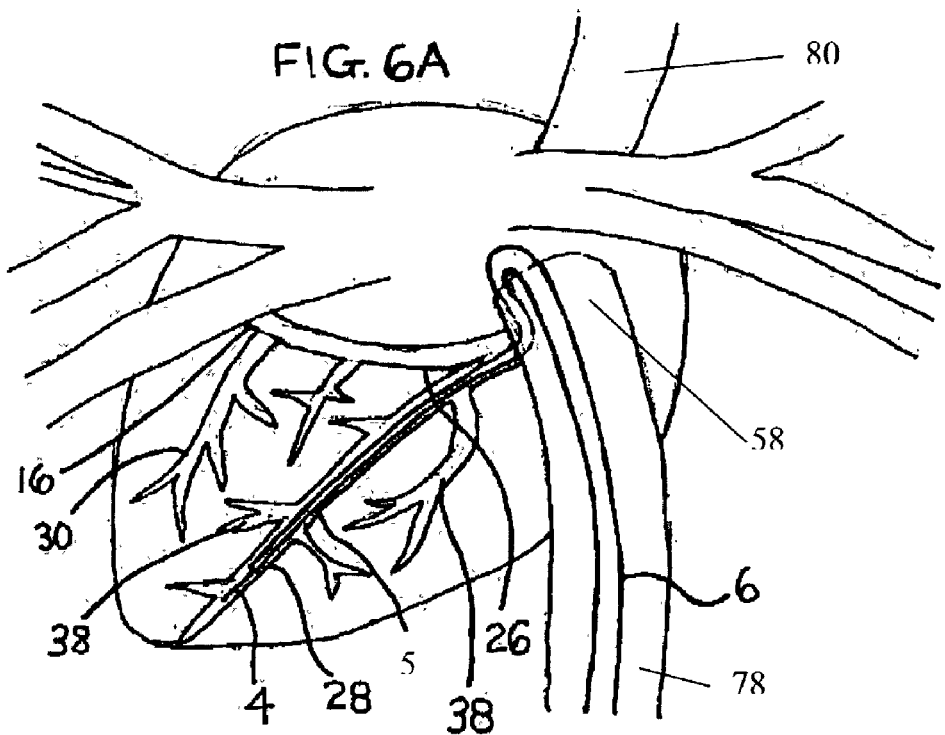
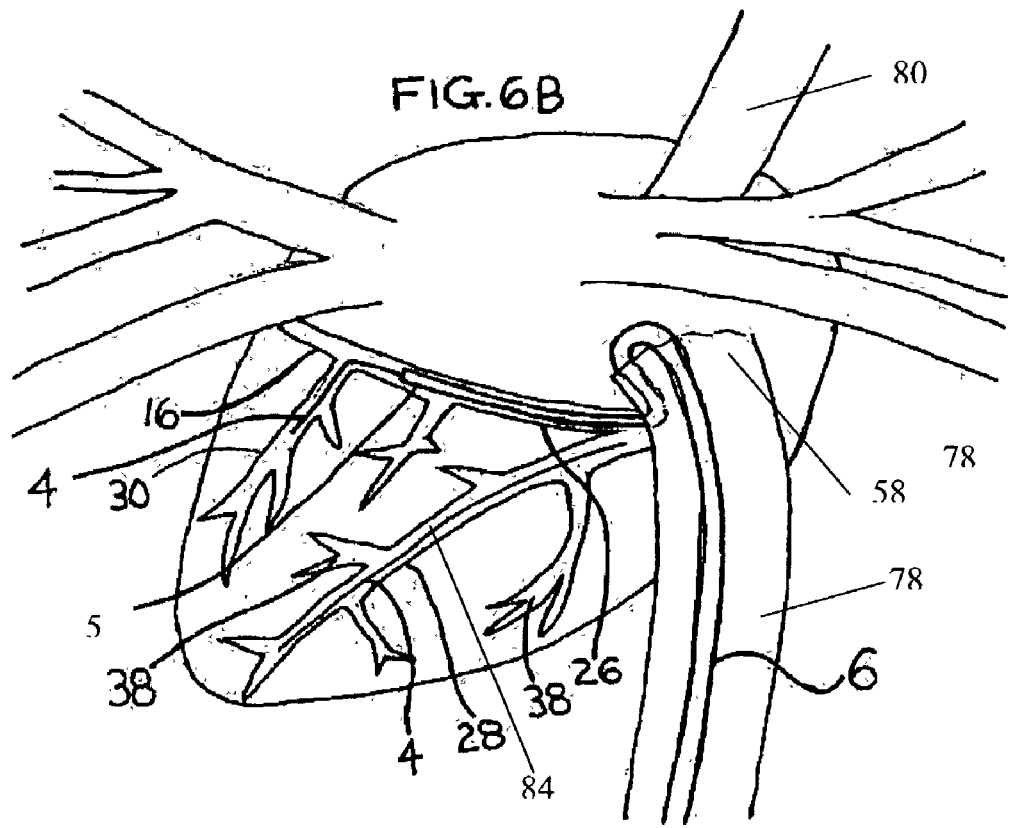

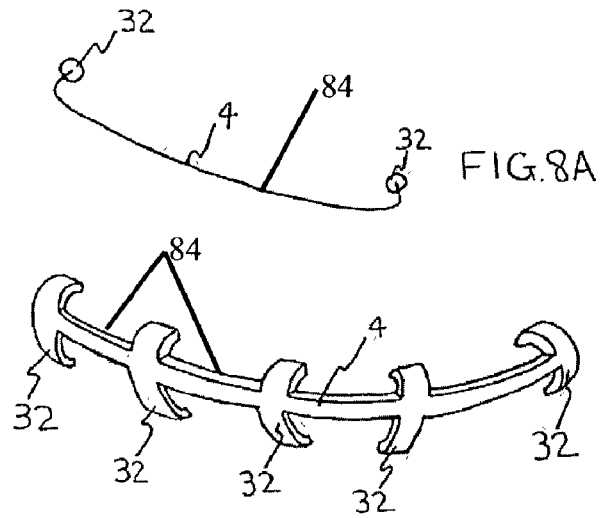
FIG. 8A
FIG. 8B
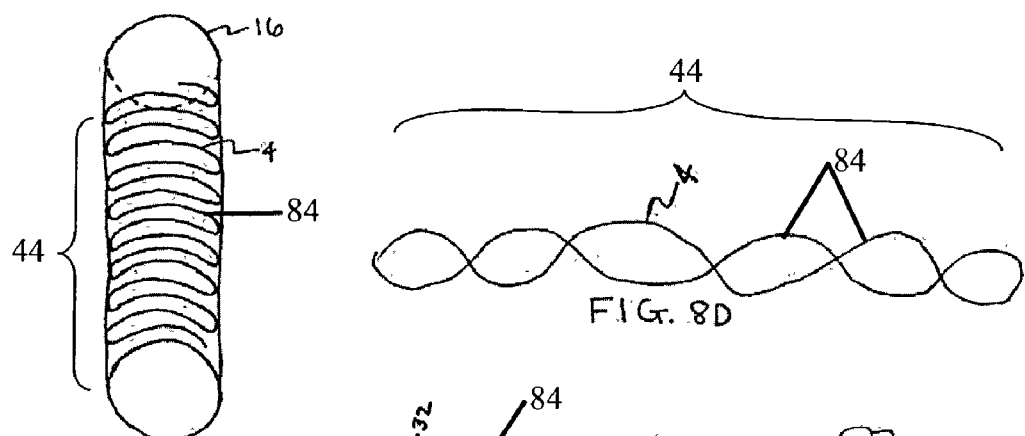
FIG. 8C
FIG. 8D
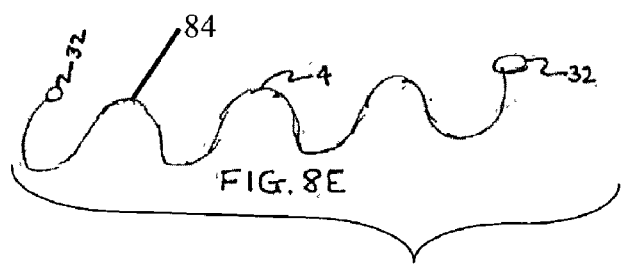
FIG. 8E
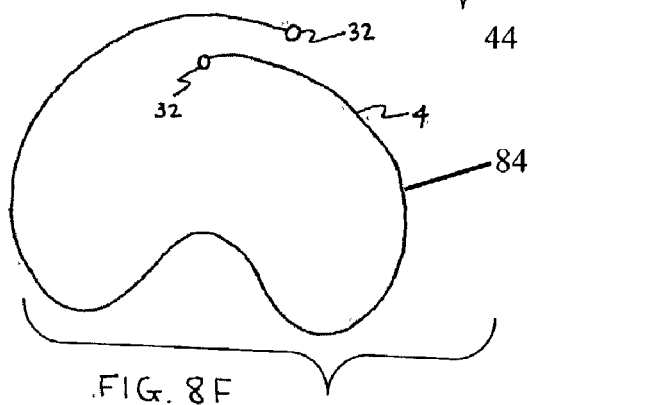
FIG. 8F

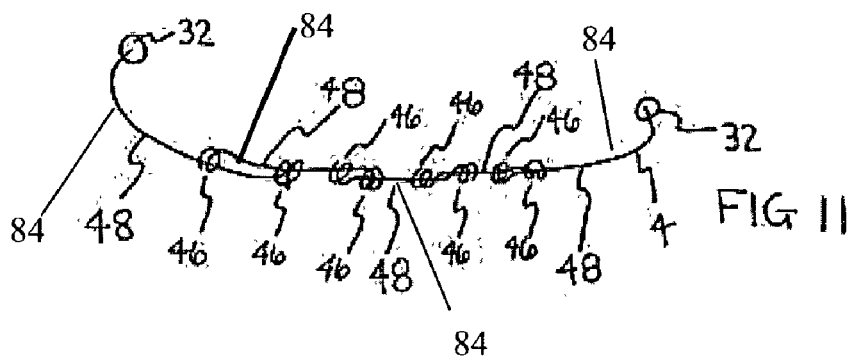
FIG. 11
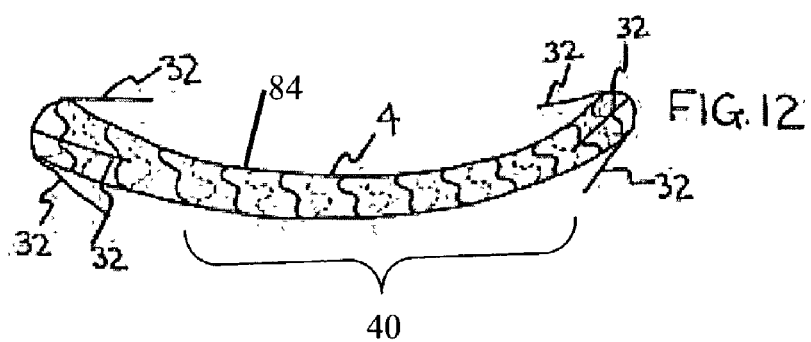
FIG. 12
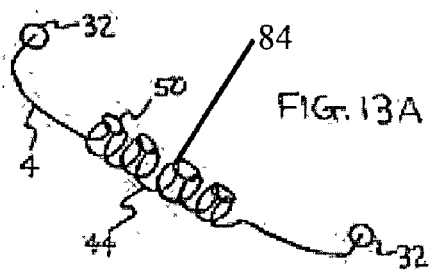
FIG. 13A
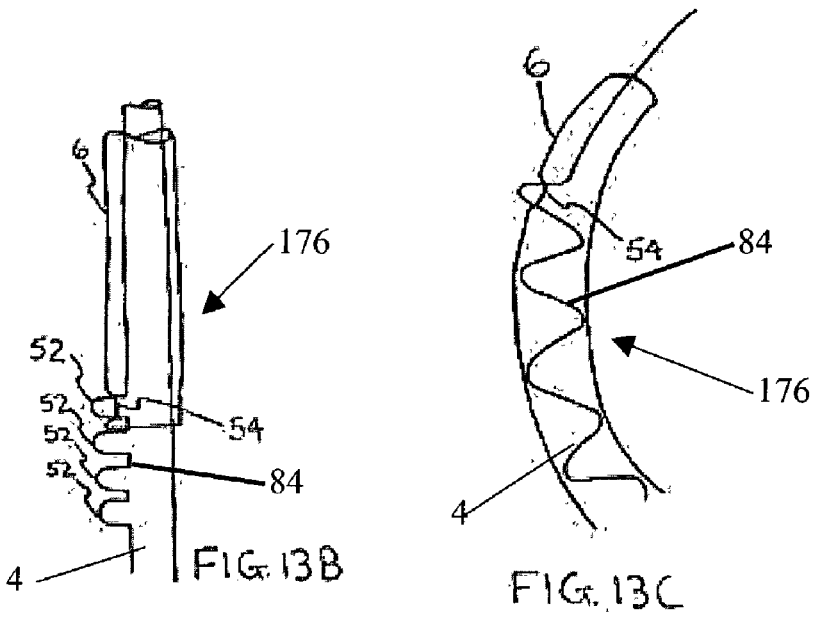
FIG. 13B
FIG. 13C

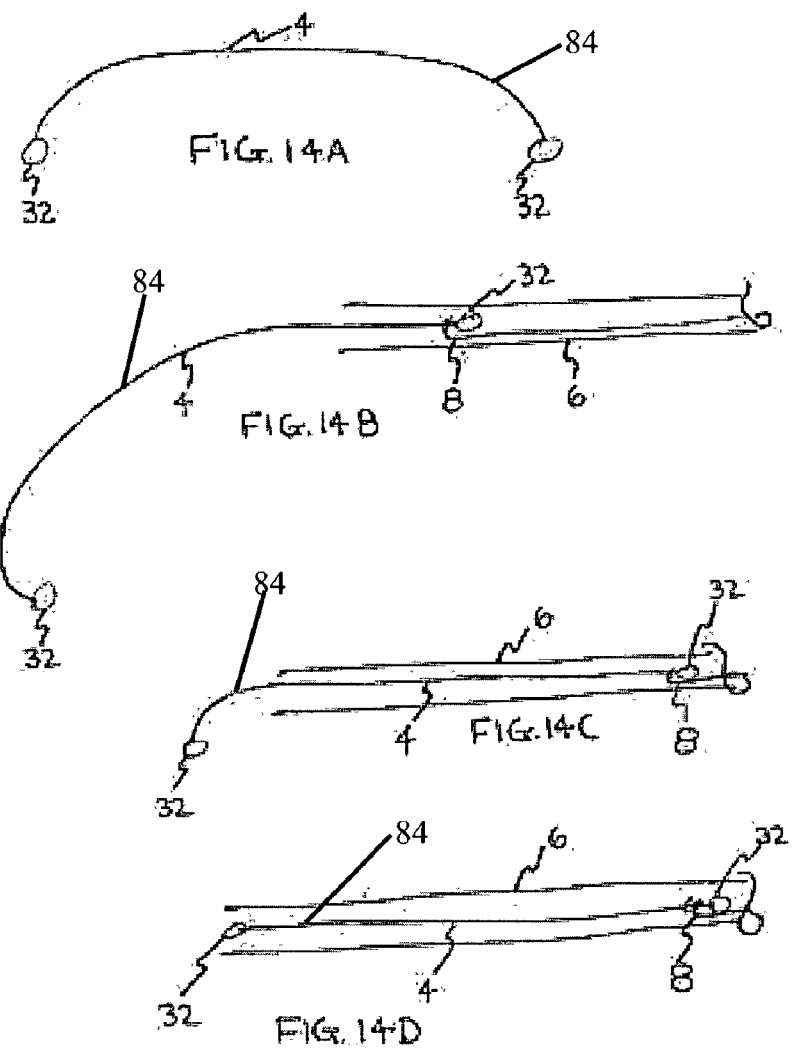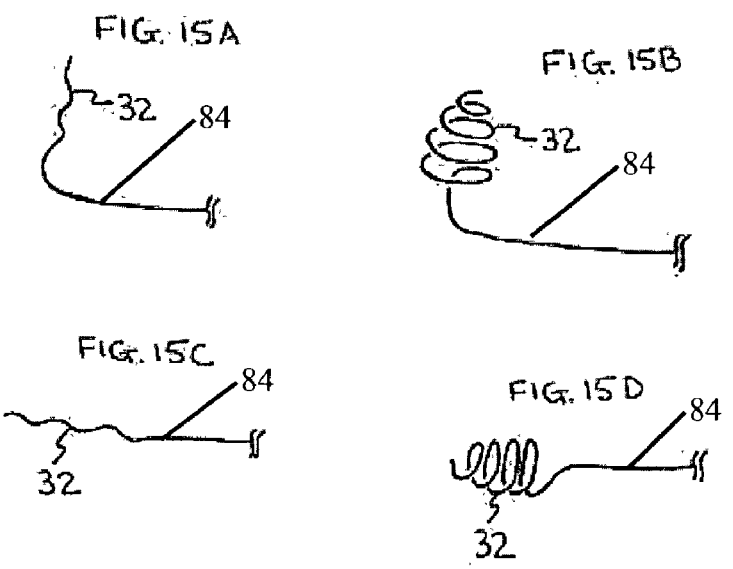

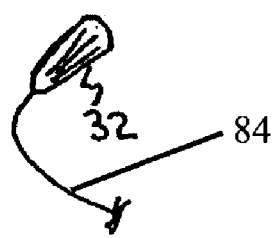
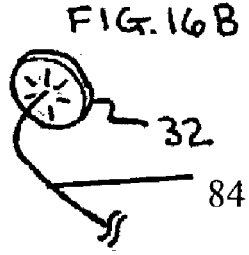
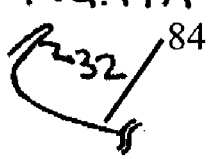
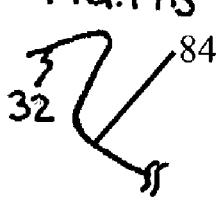
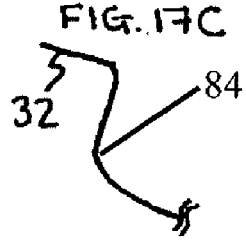
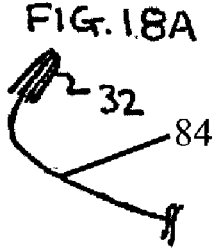
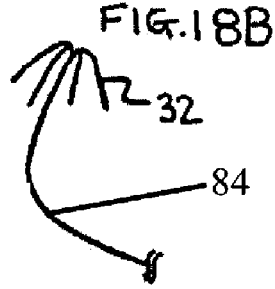
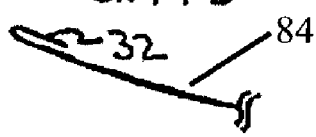
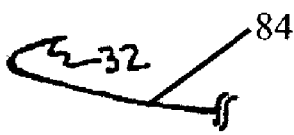
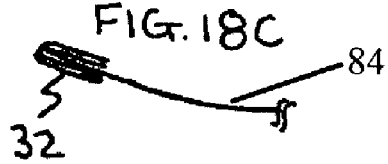
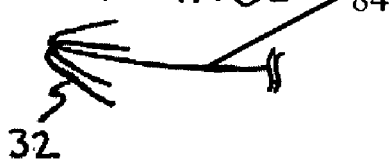

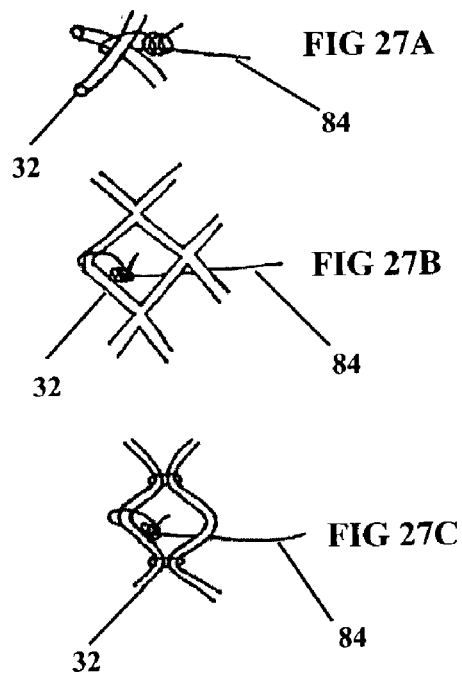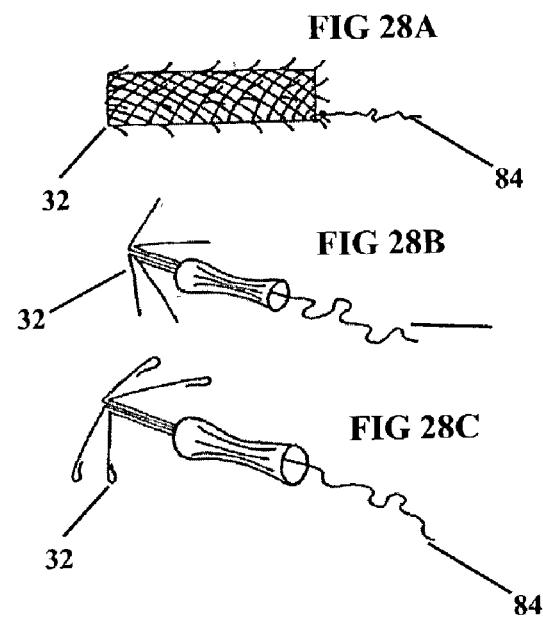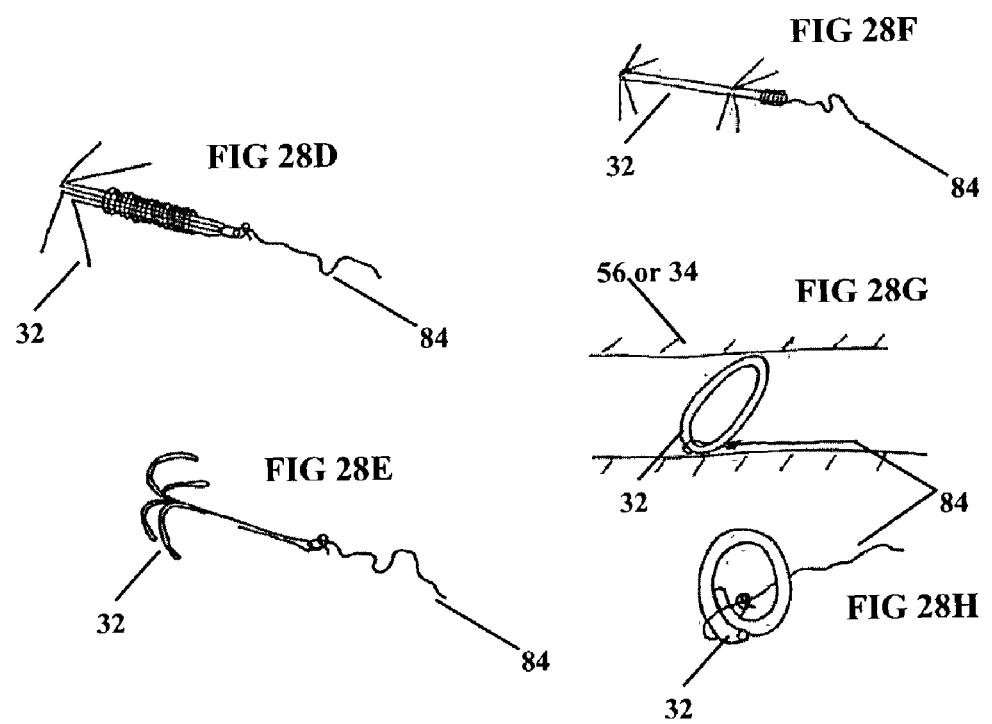

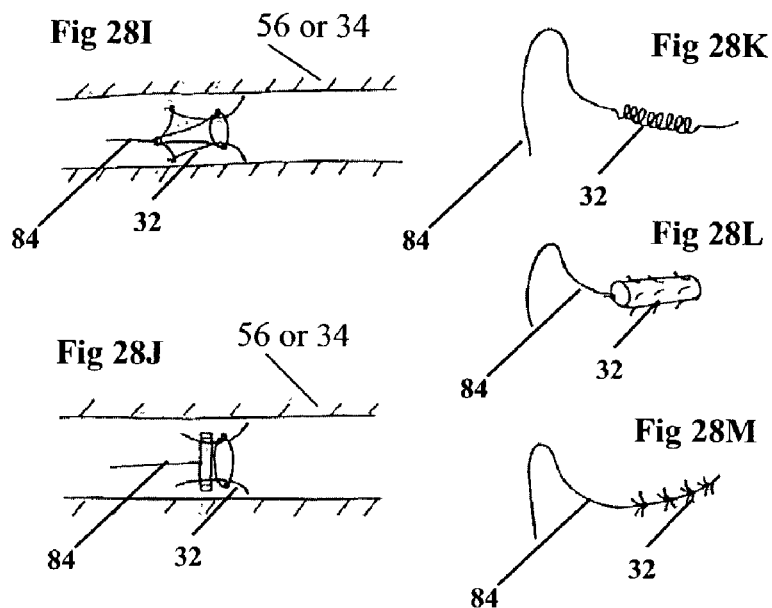
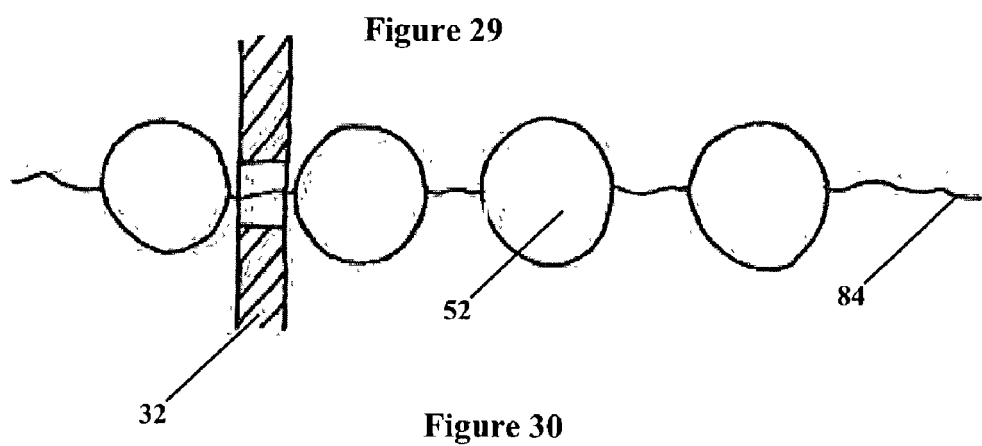
Figure 29
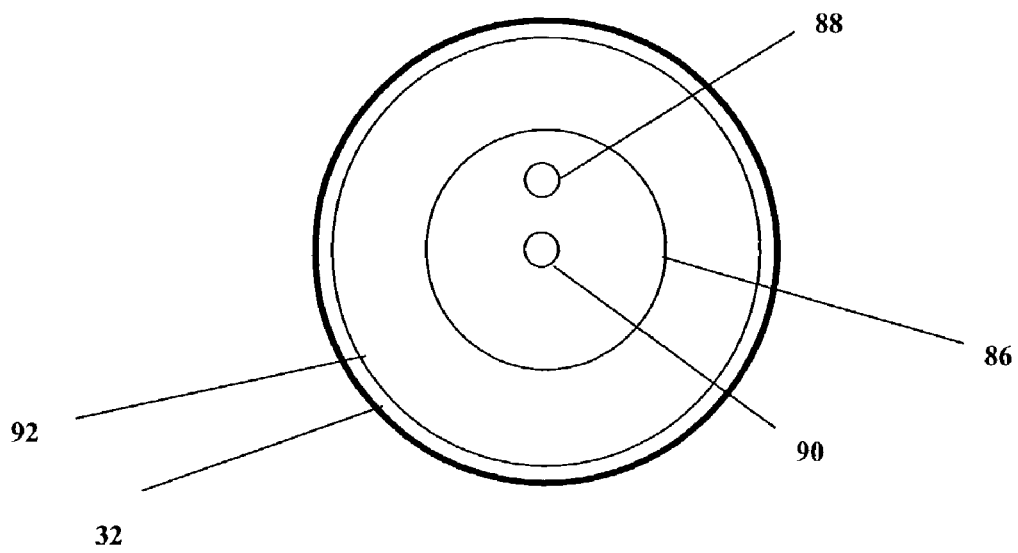
Figure 30

Figure 32A
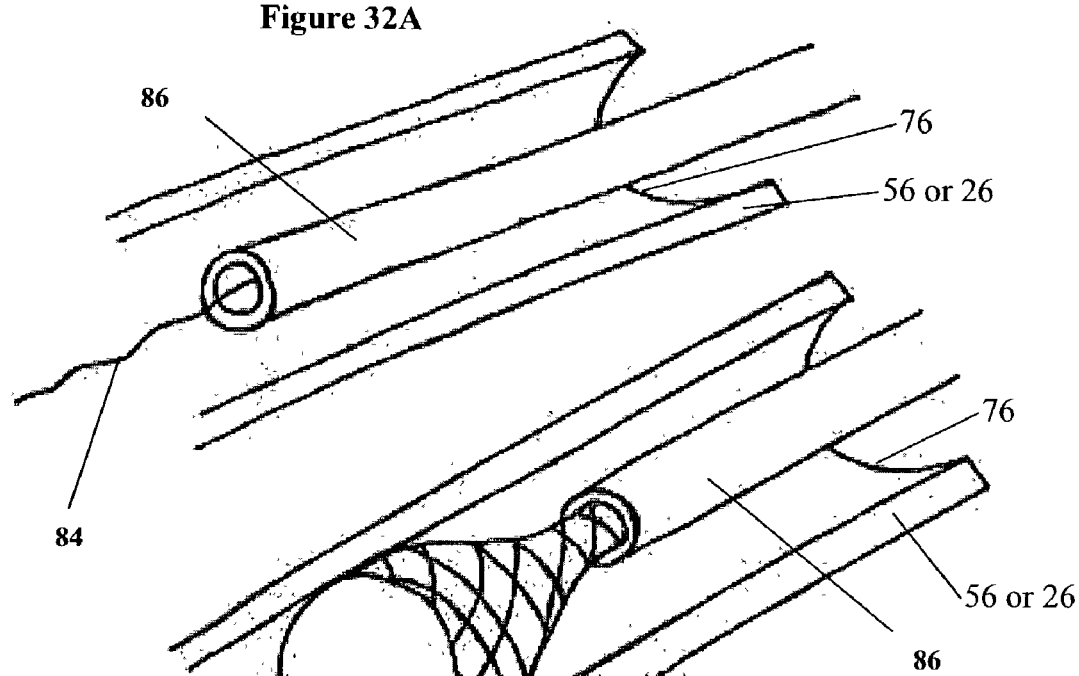
Figure 32 B
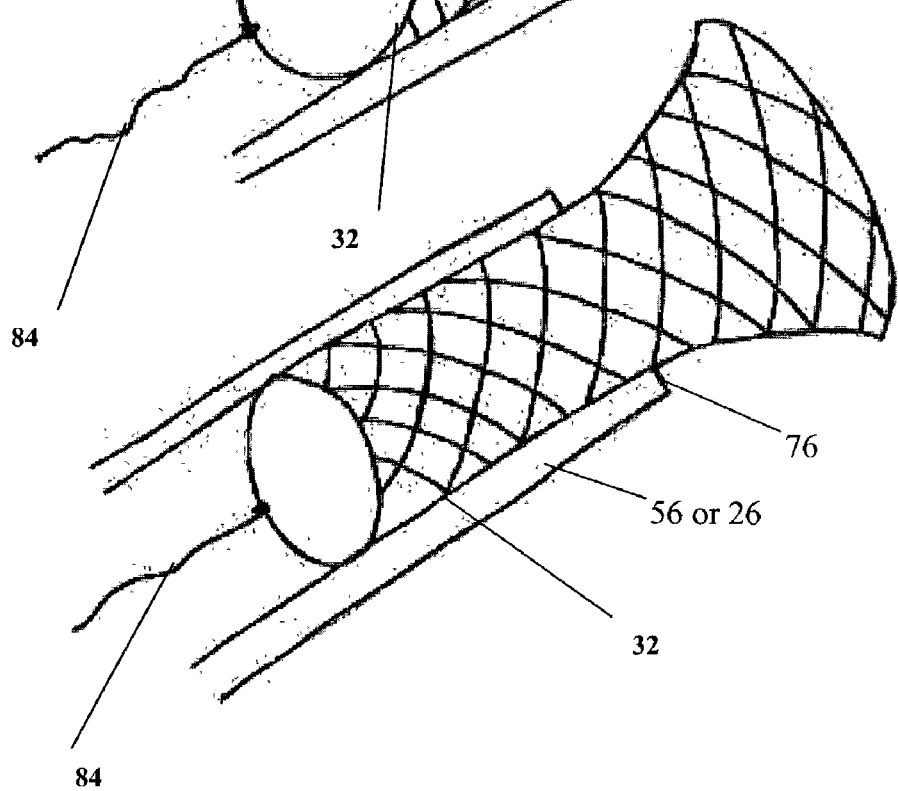
Figure 32C

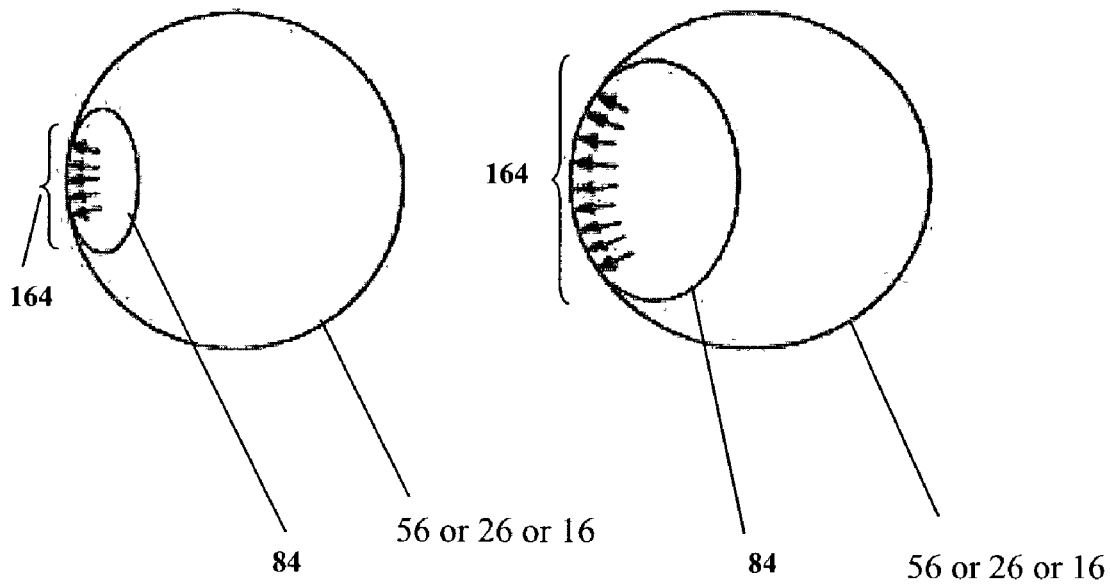
Figure 33A
Figure 33B
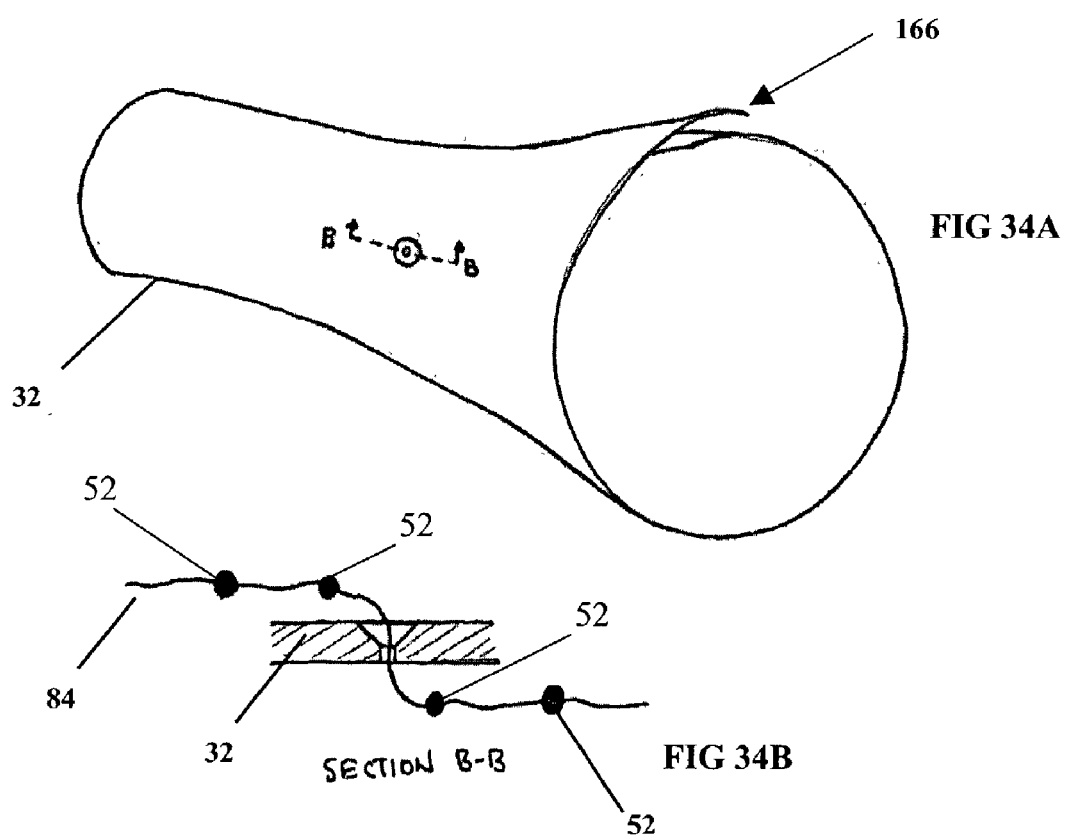
FIG 34A
FIG 34B

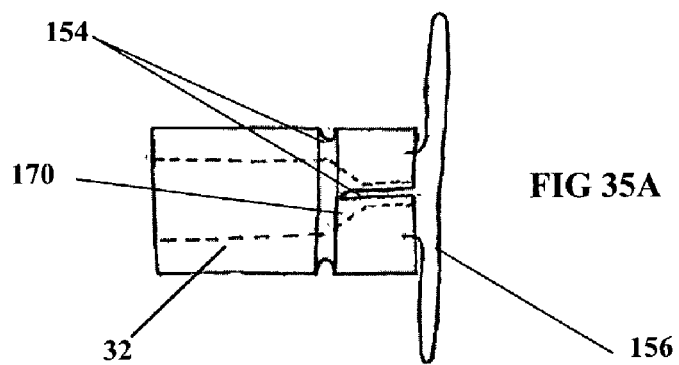
FIG 35A
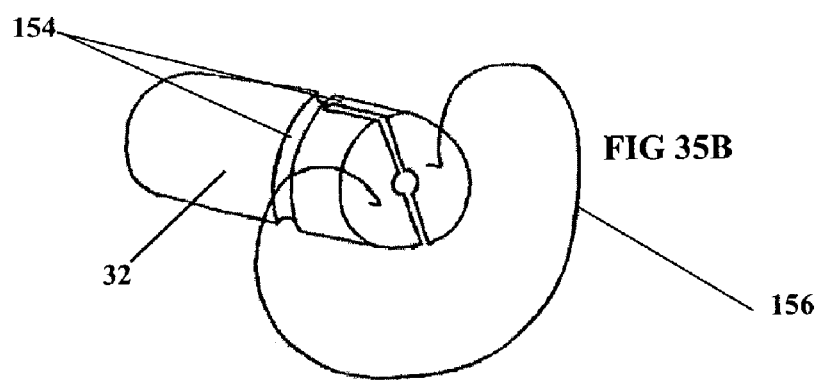
FIG 35B
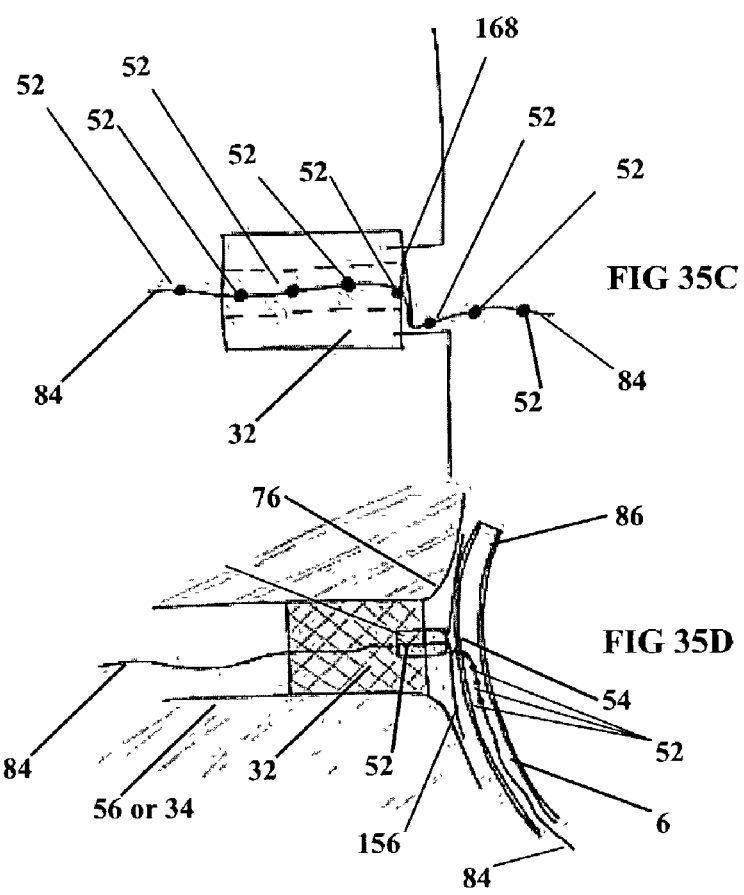
FIG 35C
FIG 35D

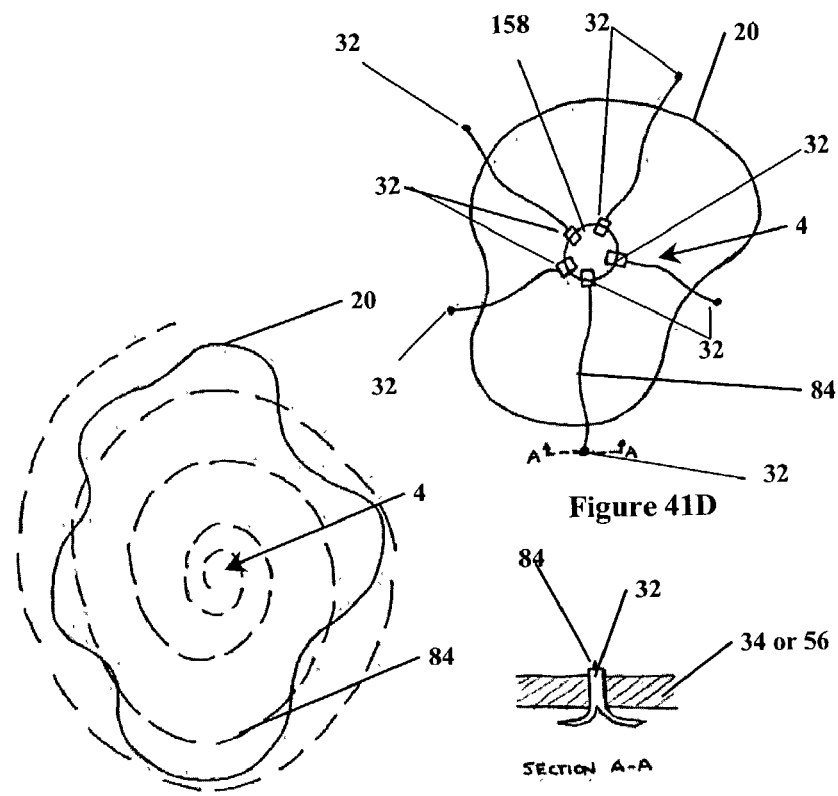
Figure 41D
Figure 41E
Figure 41C
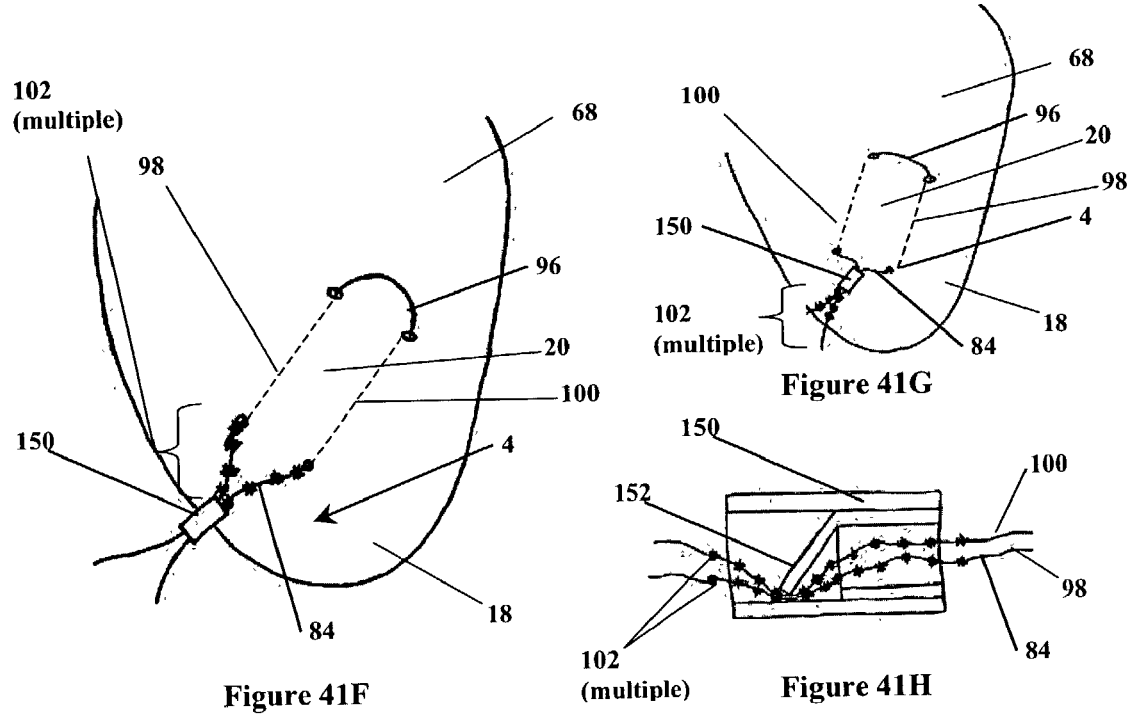
Figure 41F
Figure 41G
Figure 41H

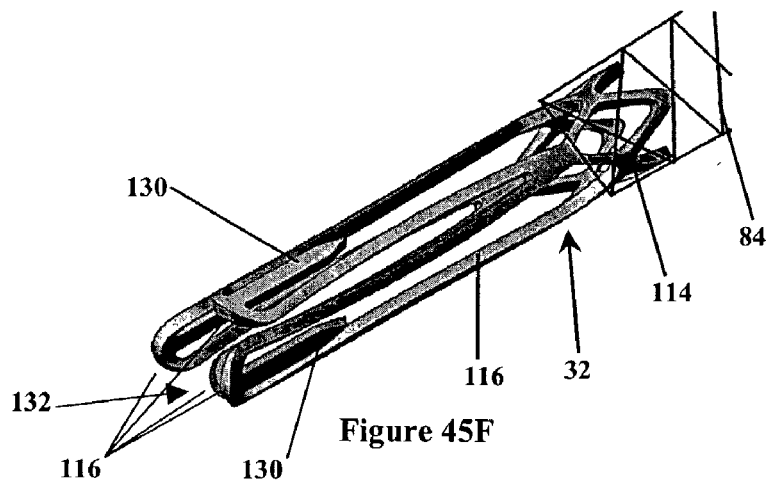
Figure 45F
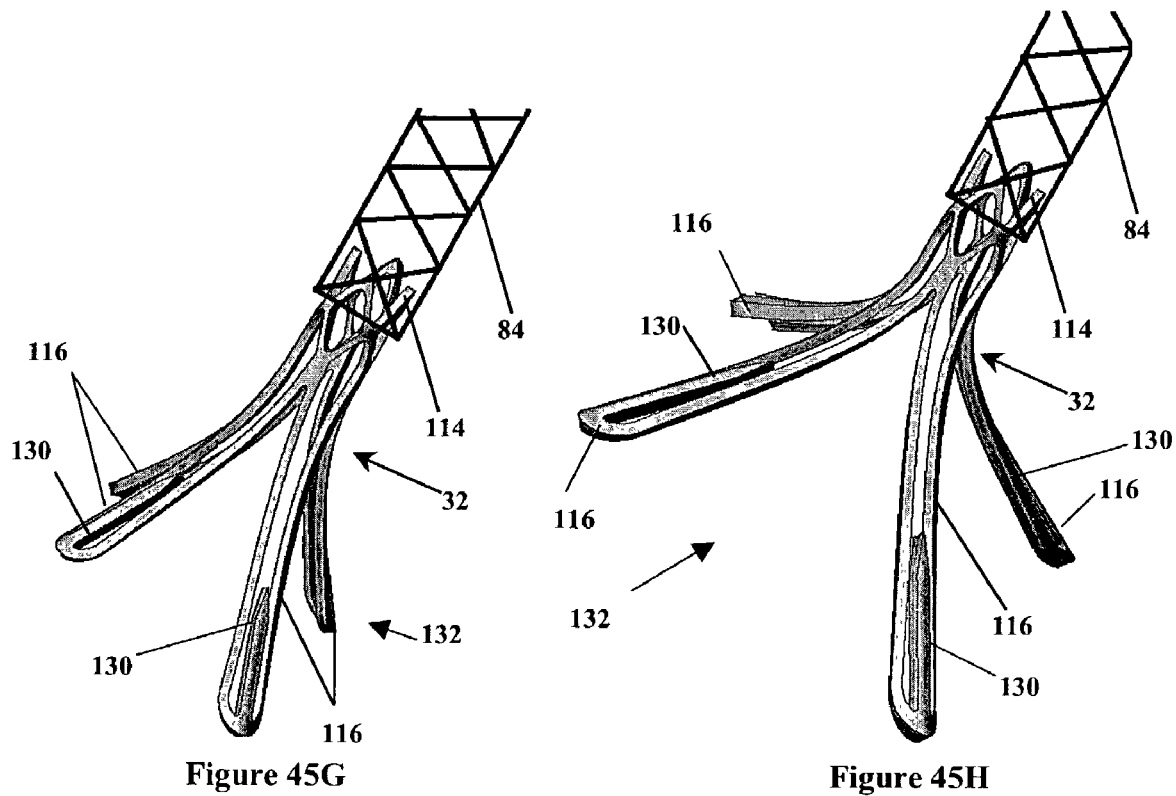
Figure 45G
Figure 45H

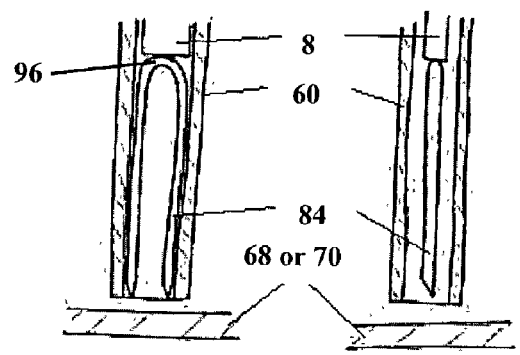
FIG 46A  FIG 46B
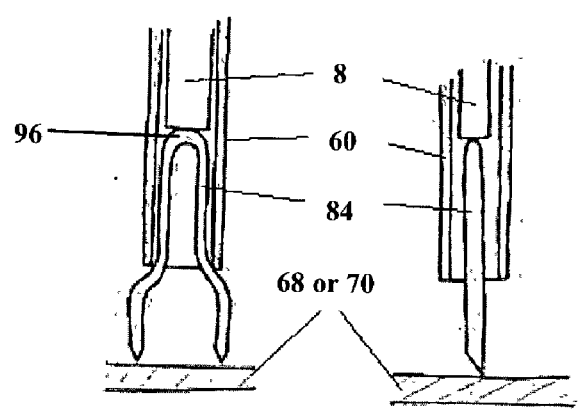
FIG 46C  FIG 46D
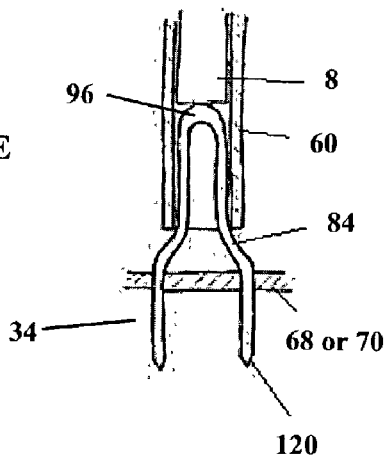
FIG 46E
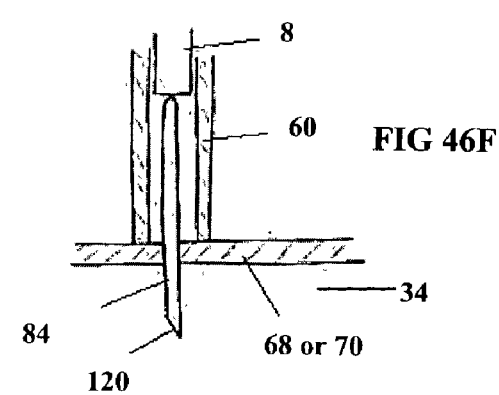
FIG 46F
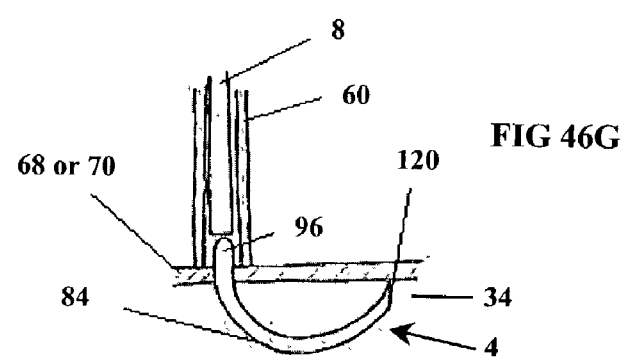
FIG 46G

FIG 46L
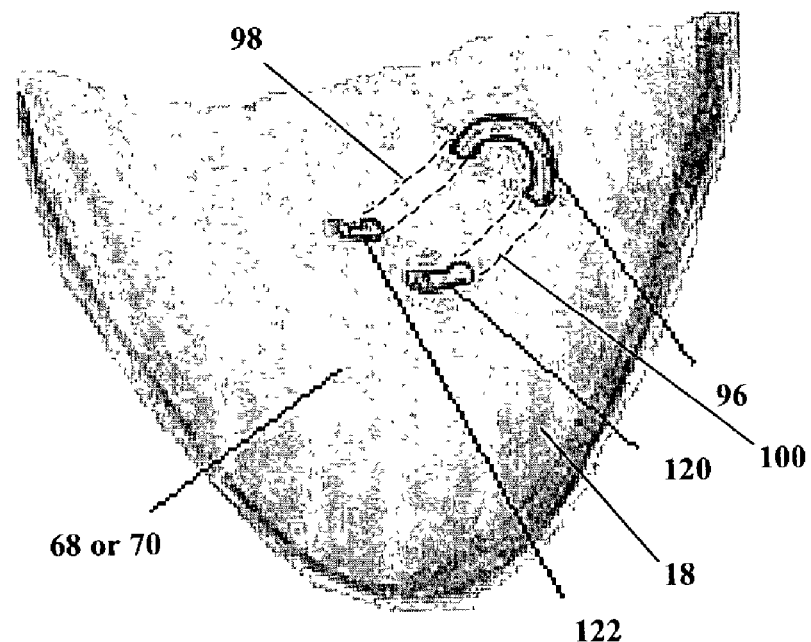
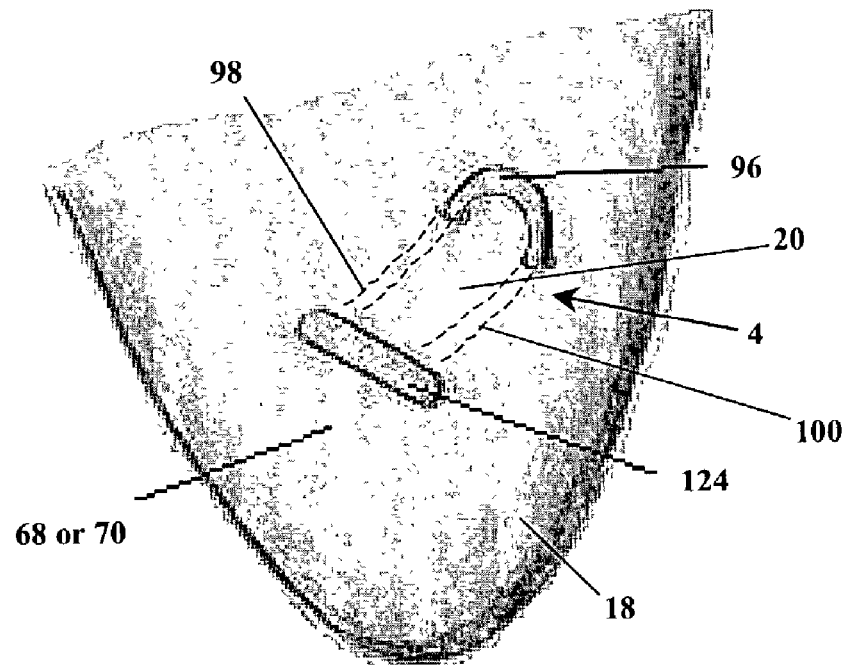
FIG 46M

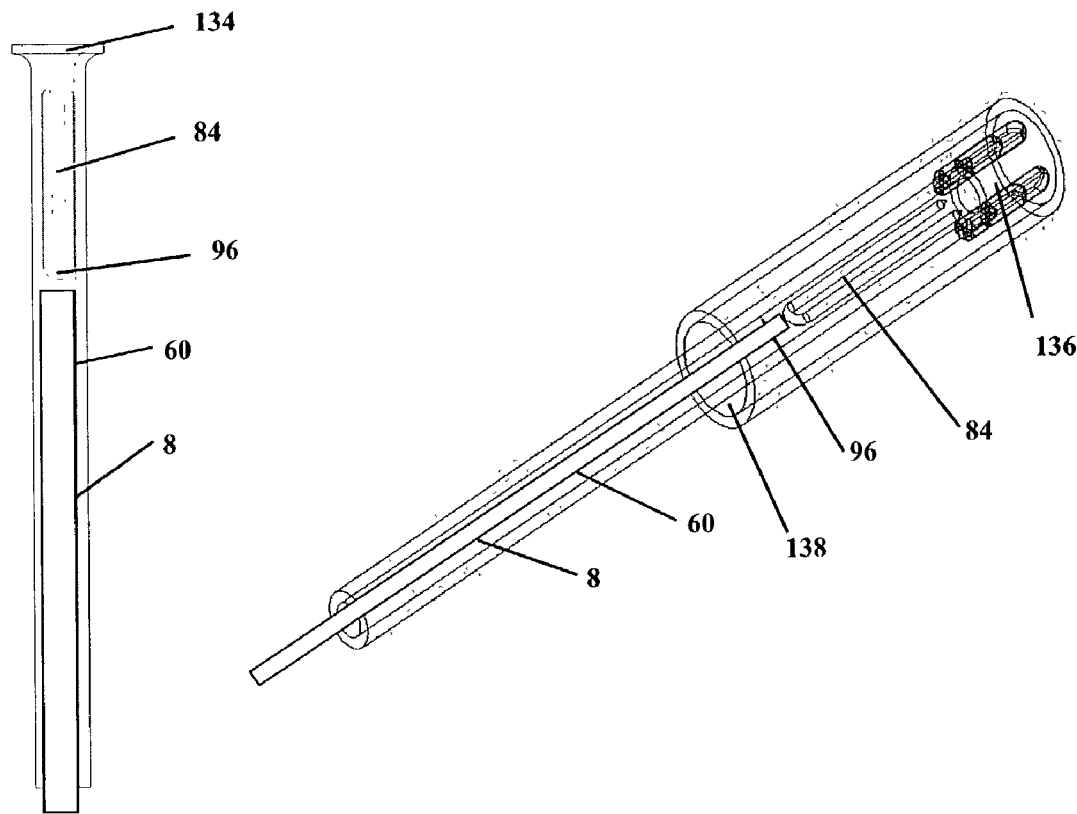
Figure 46N
Figure 46O
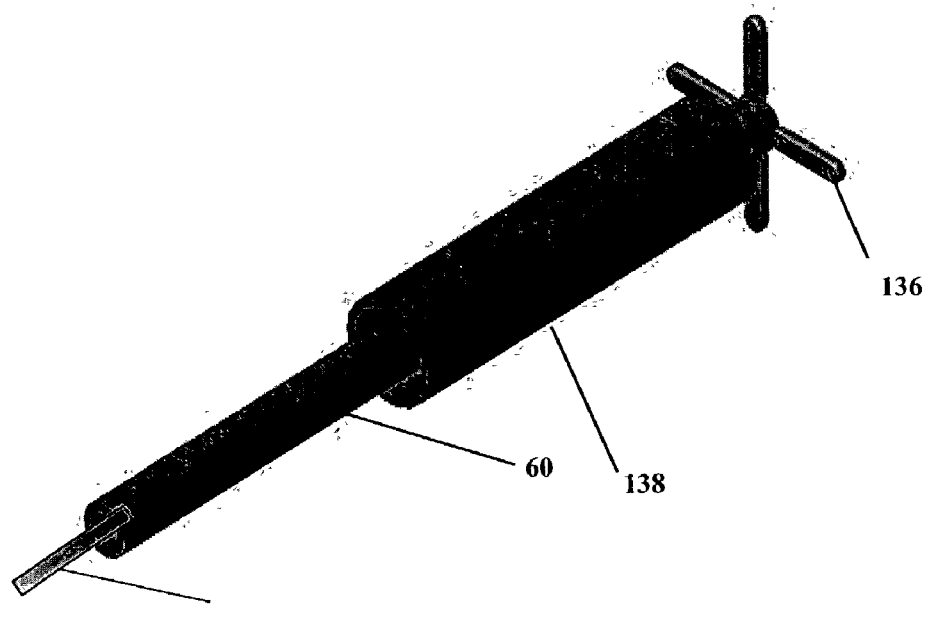
Figure 46P

SYSTEMS FOR HEART TREATMENT

CROSS-REFERENCE TO RELATED APPLICATIONS

This application claims the benefit of Provisional Application Ser. No. 60/329,694 entitled "Percutaneous Cardiac Support Structures and Deployment Means" filed Oct. 16, 2001 and Provisional Application Ser. No. 60/368,918 entitled "Percutaneous Vascular Tensioning Devices and Methods" filed Mar. 29, 2002, each of which is incorporated herein by reference.

FIELD OF THE INVENTION

The present invention relates generally to minimally invasive medical devices for treating or preventing congestive heart failure and related or concomitant valvular dysfunction. More specifically, the invention relates to tensioning structures and related deployment devices to mitigate changes in the ventricular structure and geometry and deterioration of global left and right ventricular performance related to tissue damage from myocardial ischemia, acute myocardial infarction (AMI), valve related disease or dysfunction, or other instigators of deterioration of cardiac function.

BACKGROUND

Congestive heart failure (CHF) is a progressive and lethal disease if left untreated. CHF syndrome often evolves as a continuum of clinical adaptations, from the subtle loss of normal function to the presence of symptoms refractory to medical therapy. While the exact etiology of the syndrome that causes heart failure is not fully understood, the primary cause of CHF is left ventricular dysfunction (i.e., the inability of the heart to properly and adequately fill or empty blood from the left ventricle with adequate efficiency to meet the metabolic needs of the body).

In addition, non-cardiac factors can also be activated due the overall degenerative cycle that ensues. These include neuro-hormonal stimulation, endothelial dysfunction, vasoconstriction, and renal sodium retention all of which can cause dyspnea, fatigue and edema rendering patients unable to perform the simplest everyday tasks. These types of non-cardiac factors are secondary to the negative, functional adaptations of the ventricles, cardiac valves and/or load conditions applied to or resisted by these structures. With existing pharmacological, surgical and device-based therapies symptoms can be alleviated, but the quality of a patient's life remains significantly impaired. Further morbidity and mortality associated with the disease is exceptionally high.

Ischemic heart disease is currently the leading cause of CHF in the western world, accounting for greater than 70% of cases worldwide. In these cases, CHF can precipitate from ischemic conditions or from muscle damage (i.e., due to obstruction of a coronary artery) which can weaken the heart muscle, thereby initiating a process known as remodeling in which changes in cardiac anatomy and physiology include ventricular dilatation, regional wall motion abnormalities, decreases in the left ventricular ejection fraction and impairment of other critical parameters of ventricular function. Such left ventricular dysfunction may be further aggravated by hypertension and valvular disease in which a chronic volume or pressure overload can alter the structure and function of the ventricle. Decreases in systolic contraction can lead to cardiomyopathy, which further exacerbates the localized, ischemia damaged tissue or AMI insult into a global impairment, thereby leading to episodes of arrhythmia, progressive pump failure and death.

Ischemia-damaged and/or infarct damaged heart muscle tissue results in progressive softening or degeneration of cardiac tissue. These ischemic and infarcted zones of the heart muscle wall have limited, if not complete loss of tissue contractile functionality and overall physical integrity and present an analogous situation to those presented by vascular aneurysms.

CHF is usually associated with a progressive enlargement of the heart as it increases contractility and heart rate in a compensatory response to the decreasing cardiac output. With this enlargement, the heart's burden is increased to pump more blood with each pump cycle. A phenomenon known as myocardial stretch is implicated in a degenerative cycle/ feedback loop that causes areas of compromised heart muscle tissue to bulge further outward. When the bulging is related to AMI, this behavior is characterized as infarct expansion. With this bulging, the heart's natural contraction mechanism is dissipated and attenuated, resulting in a marked and progressing decrease in cardiac output.

Normal cardiac valve closure (especially that of the mitral valve) is dependent upon the integrity of the myocardium, as well as that of the valve apparatus itself. The normal mitral valve is a complex structure consisting of leaflets, an annulus, chordae tendineae, and papillary muscles. Any damage or impairment in function of any of these key components can render the valve structure incompetent. Impairment of valve function, due to independent factors (i.e., a concomitant valve pathology) or dependent factors (i.e., valve dilation related to dilated cardiomyopathy), can result in valvular insufficiency further exacerbating the degenerative CHF cycle.

The major objectives of heart failure therapy are to decrease symptoms and prolong life. The American Heart Association guidelines suggest that optimal treatment objectives include means to increase survival and exercise capacity, and to improve quality of life, while decreasing symptoms, morbidity and the continued progression of the cardiac degeneration. Various pharmacological and surgical methods have been applied both with palliative and therapeutic outcome goals. However, there still remains no definitive cure for CHF.

Modem pharmacological approaches such as diuretics, vasodilators, and digoxin dramatically lessen CHF symptoms and prolong life by mitigating the non-cardiac factors implicated in the syndrome. Furosemide (more commonly known as Lasix™) is also a valuable diuretic drug which eliminates excess water and salt from the body by altering kidney function and thereby increasing urine output, thus relieving circulatory congestion and the accompanying pulmonary and peripheral edema.

Vasodilators, like angiotensin-converting-enzyme (ACE) inhibitors have become cornerstones in treatment of heart failure. These kinds of vasodilators relax both arterial and venous smooth muscle, thereby reducing the resistance to left ventricular ejection. In patients with enlarged ventricles, the drug increases stroke volume with a reduction in ventricular filling pressure. Administering digoxin has also been found to be positively inotropic (i.e., strengthening to the heart's contractile capability).

On the surgical front, cardiomyoplasty is a recently developed treatment of CHF. In such a procedure, the latissimus dorsi muscle is removed from the patient's shoulder, wrapped around the heart and chronically paced in synchrony with ventricular systole in an effort to assist the heart to pump during systole. The procedure is known to provide some symptomatic improvement, but is controversial with regard to its ability to enable active improvement of cardiac performance. It is hypothesized that the symptomatic improvement is primarily generated by passive constraint and mitigation of the degenerative, remodeling process. In spite of the positive outcome on relieving some of the symptoms, the procedure is highly invasive, requiring access to the heart via a sternotomy, expensive, complex and of unknown durability (due to the muscle wrap blood flow requirements and fibrosis issues).

Another surgical procedure of interest has been developed by R. Bautista, MD. In this procedure, the overall mass, volume and diameter of the heart are physically reduced by dissection and removal of left ventricular tissue. While innovative, the procedure is highly invasive, traumatic and costly. Further, the actual volume reduction results in a reduction in valve competence and elicits the associated regurgitation.

Surgical treatment of valvular dysfunction includes a wide range of open procedure options ranging from mitral ring annuloplasty to complete valve replacement using mechanical or tissue-based valve prosthesis. While being generally successful and routine in surgical practice today, these procedures are also costly, highly invasive and are still have significant associated morbidity and mortality.

More recently, mechanical assist devices which act as a bridge to transplant such as the left ventricular assist device (LVAD) or the total artificial heart (TAH) implant have become available. LVAD's are implantable, mechanical pumps that facilitate the flow of blood from the left ventricle into the aorta. The latest TAH technologies feature many improved design and material enhancements that increase their durability and reliability. Still, the use of such devices is limited by high costs and a lack of substantial, clinical evidence warranting their use.

Other device-based options for CHF patients include approaches for reshaping, reinforcement and/or reduction of the heart's anatomical structure using polymeric and metallic bands, cuffs, jackets, balloon/balloon-like structures or socks to provide external stress relief to the heart and to reduce the . propensity/capability of the cardiac tissue to distend or become continually stretched and progressively damaged with pump cycles. Examples of such devices are U.S. Pat. No. 2002/0045799 and U.S. Pat. No. 5,702,343. In addition, devices are being studied that attempt to prevent the tissue remodeling using tethers and growth limiting struts or structures described in various patents (i.e., U.S. Pat. No. 6,406,420).

Generally, all of these concepts support the cardiac muscle and restrict growth externally and globally via surgical placement about the epicardium and in some instances are positioned across the cardiac muscle tissue. As a result, these types of approaches require unnecessary positioning of the devices over healthy (non local, undamaged) areas or zones of the heart affecting the entire organ when the primary treatment is usually focused is on the left ventricle or the mitral valve annulus. Such non-localized treatment can elicit iatrogenic conditions such as undesired valvular dysfunction and/or constrictive physiology due to over restriction of the heart by such restraints.

Recently, several-device based options have been introduced where implants are positioned by minimally invasive means in the coronary sinus in one configuration and then assume a post deployment configuration that constricts around the heart annulus to improve valve competence in dilated cardiomyopathy (see, U.S. patent application Publication No. 2002/016628.) While appealing, the clinical efficacy of this approach is unknown at this time.

The ultimate treatment for people suffering end stage CHF is a heart transplant. Transplants represent a massive challenge with donor hearts generally in short supply and with the transplant surgery itself presenting a high risk, traumatic and costly procedure. In spite of this, transplants present a valuable, albeit limited, upside, increasing life expectancy of end stage congestive heart failure patient from less than one year up to a potential five years.

In view of the above, it should be evident that there is currently no ideal treatment among the various surgical, pharmacological, and device-based approaches to treat the multiple cardiac and non-cardiac factors implicated with the syndrome of CHF. Accordingly, there is a clear, unmet clinical need for technology that is minimally invasive (especially, percutaneous) that can prevent, treat or reduce the structural remodeling to the heart and its sub-structures across the continuum of the CHF syndrome beginning acutely with the ischemia or ischemic infarct through the end stages where there is often left ventricular and valvular dysfunction refractory to conventional treatments.

Still, patients suffering from CHF, who are unresponsive to medication, generally precluded to open surgical approaches and potentially awaiting transplant could derive massive and direct benefit from a minimally invasive device as provided by the present invention to limit further degeneration of their condition. In addition, implant embodiments of the present invention can also facilitate positive or reverse remodeling (i.e., provide a mild compressive force both during systole and diastole to improve cardiac output and efficiency).

SUMMARY OF THE INVENTION

The present invention meets these needs with tensioning structures that can be utilized locally (e.g., left ventricular anterior wall only versus about the entire heart) to reduce wall stresses, reinforce the walls, and reduce/limit volume of the heart muscle as required using percutaneous, minimally invasive surgical (MIS), and open surgical means or a combination thereof. Devices according to the present invention may be used to facilitate operator controlled "tailoring" of localized treatment using various embodiments of the invention at various chosen target zones (i.e., left ventricle, mitral valve annulus, or sub-valvular apparati). Custom tailoring of each tensioning structure enables application of compression against specific regions of tissue in one, two or three dimensions relative to the heart's surface and patient specific adjustability of the amount of compression applied to the tissue to optimize the heart's overall hemodynamic performance.

Tensioning structures according to the invention can be individually placed within or about the heart (intravascularly or extravascularly) working in concert to provide reinforcement against myocardial stretch (or infarct expansion) and additionally to facilitate contraction of tissue previously subject to such myocardial degeneration. In doing so, the contractile and expansion energies of the heart can be transferred to and across the weakened sections of the heart from the more viable sections of the heart muscle. Such devices provide localized dynamic support or reinforcement and are active throughout the cardiac cycle unlike previous device approaches that generally only reduce the stress in the heart wall during diastole. Diastolic compliance can also be regulated or controlled with structures according to the invention. Also, the tensioning structures facilitate and maintain a more efficient and perhaps optimal wall motion through the cardiac cycle thereby aiding in diastolic filling and systolic contraction at the tissue area that has been compromised by ischemia, infarct or other abnormalities. The tensioning structures are implanted in target heart regions using standard cardiovascular, interventional techniques using guiding catheters and introducing sheaths or less invasive surgical techniques involving port access or small incisions into the thoracic cavity to eliminate the need for more radical surgery (e.g., median sternotomy) to provide a potential, palliative or therapeutic response to the disease.

Furthermore, the tensioning structures of the invention may provide a complete, comprehensive solution for treatment of congestive heart failure addressing deficiencies to the wall motion of the heart (e.g. akinesis, hypokinesis or dyskinesis), and/or valve insufficiencies. The present invention comprises such device-based technology as summarized above, that is further described below with associated methodology, including deployment, production, development and use of the same. Still further, as part of a system, kit or otherwise, the, invention shown herein may be provided or used in connection with the invention, described in U.S. Provisional Patent Application Ser. No. 60/418,018, entitled "Minimally Invasive Cardiac Force Transfer Structures," to the inventors hereof and filed on even date herewith, the same being incorporated by. reference in its entirely as part of the present invention.

BRIEF DESCRIPTION OF THE DRAWINGS

FIGS. 1A and 1B show perspective views of a healthy heart in systole and diastole, respectively.

FIGS. 2A and 2B show perspective views of a diseased (enlarged) heart in systole and diastole, respectively.

FIGS. 3A and 3B show perspective views of a diseased heart reinforced with an intravascular, tensioning structure of the invention in systole and diastole respectively.

FIGS. 5A and 5B show anterior views of a heart with intravascular, tensioning structures of the invention being percutaneously deployed into various target vessels.

FIGS. 6A and 6B show posterior views of a heart with intravascular, tensioning structures of the invention being percutaneously deployed into various target vessels.

FIGS. 8A to 8F show various tensioning structures of the invention.

FIG. 11 shows a side view of a tensioning structure embodiment incorporating independent wire components interlaced with one another.

FIG. 12 shows a side view of a tensioning structure embodiment incorporating a tubular body with radial anchor members.

FIGS. 13A to 13C show adjustable cardiac support structure embodiments that enable modification of force outputs: FIGS. 13B and 13C show ratcheting mechanisms of adjustable tensioning structures.

FIGS. 14A to 14D show side-sectional views highlighting the process of positioning a tensioning structure in a delivery catheter.

FIGS. 15A to 15D, 16A, 16B, 17A to 17E, 18A to 18D show side views of various tensioning structure anchor members in compressed and expanded orientations, variously.

FIGS. 27A to 27C show close-up views of various anchor structures in connection with various tensile member attachment points.

FIGS. 28A to 28M show side views of various anchor structures and attached tensile member configurations for tensioning structures according to the invention.

FIG. 29 shows a side-sectional view of a ratcheting mechanism of an adjustable tensioning structure.

FIG. 30 shows a cross-sectional view of the distal tip of a delivery catheter system used to place tensioning structures.

FIGS. 32A to 32C show side-sectional views of an ostium to a vessel highlighting the process of deploying a self-expanding anchor member of a tensioning structure using a retractable sheath delivery system.

FIGS. 33A and 33B show cross-sectional views of tensile, members in a vessel illustrating variance in force distributions.

FIGS. 34A and 34B, respectively, show a perspective view and a close-up view along line B—B of a tensioning structure anchor with a locking mechanism adapted for manually tightening the tensile member.

FIGS. 35A to 35D show a side, perspective, and two-sided sectional views, respectively, of another anchor structure adapted for manual adjustment and locking of the tensile member.

FIGS. 41A to 41D show a cross-sectional view of the heart, a perspective view and two top views, respectively, illustrating alternative tensioning structure, approaches; FIGS. 41E shows a side-sectional view taken along A—A of the anchor of the tensioning structure embodiment in FIG. 41D; FIGS. 41F and 41G show a myocardial tensioning structure with an anchor that is adapted for manual adjustment and locking of the tensile member; FIG. 41H show a close-up view of the anchor formations shown in FIGS. 41F and 41G.

FIGS. 45F to 45H show perspective views of an anchor member for a tensioning structure highlighting the expansion (e.g., plastic deformation via balloon expansion or self-expansion upon release from an external compression force) for the variation of the invention in FIGS. 45C to 45E.

FIGS. 46A to 46K show side-sectional views of an integrated tensioning structure that functions as a puncturing device for a deployment system, an anchor member, and the tensile member; FIGS. 46L to 46M show a perspective view of the heart with a deployed and secured integrated tensioning structure shown as in FIGS. 46A to 46K; FIGS. 46N to 46P show a side view and two perspective views, respectively, of alternative delivery systems used to deploy integrated tensioning structures into or/through the myocardium.

DETAILED DESCRIPTION

Figure 4A:
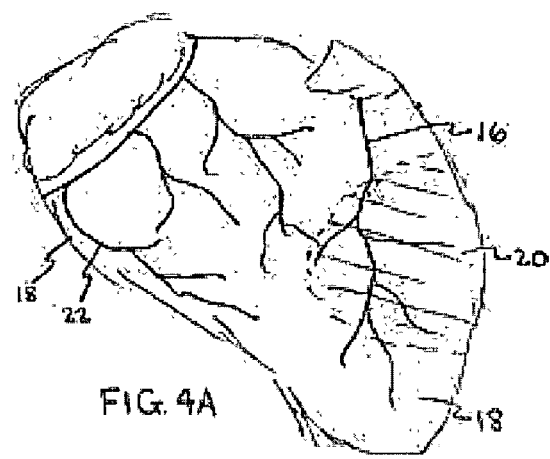
FIGS. 4A and 4B show perspective views dramatizing the progression of myocardial stretch (or infarct expansion) in a diseased, enlarged heart with the infarcted/ischemic zone shown as highlighted.

Having described the characteristics and problems of congestive heart failure in the background and summarized hereto, the treatment method and apparatus of the present invention will now be described in detail below. The variations of the invention described below may be used to provide a complete, comprehensive solution to treating congestive heart disease, and the contributing or associated co-morbid, anatomical, and physiological deficiencies. Addressing the multiple factors that affect or cause congestive heart disease can retard or reverse the implicated remodeling thereby treating or mitigating the congestive heart disease and associated symptoms.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

With initial reference to FIGS. 1A and 1B, an anterior view of a healthy heart in systole and diastole, respectively, is shown with directional arrows indicating motion of the heart in each phase. The great cardiac vein 16 is shown on the surface of the ventricle 18 of the heart. The great cardiac vein 16 resides adjacent to the left anterior descending artery (not shown).

In FIGS. 2A and 2B, perspective views are shown of a diseased (enlarged) heart in systole and diastole, respectively. An infarcted or ischemic region 20 is shown to stretch from systole to diastole consistent with the progressive remodeling that occurs due to increased diastolic filling pressures exerted on the diseased tissue. A radial and axial expansion that is experienced by the heart leads to stretching or degenerative remodeling and concomitant organ enlargement. This enlargement can be localized along the anterior wall of the left ventricle, can be located or extend septally, can include the right ventricle, and/or can involve the mitral valve annulus.

Fundamentally, all tensioning structure aspects of the present invention comprise individually or in combination of several, components or devices including tensile member(s), anchor member(s) and deployment device(s). These components or devices are designed to be able to work in concert in order to facilitate and provide palliative or therapeutic cardiac reinforcement in the following critical target areas of the heart: 1) intravascular conduits, 2) cardiac valve annulus, 3) myocardium, 4) chordae tendineae and valve leaflets. The subsections broken-out below will further describe these specific aspects of the invention.

Intravascular Conduit Tensioning Structures

A number of embodiments of the present invention are provided mainly in the context of tensioning structures positioned and anchored within intravascular conduits to provide cardiac muscle support and reinforcement. Such intravascular conduit tensioning structures can be designed to be interchangeably deployed within various vascular conduits (arteries, veins, and branching vessels associated with these structures); or through these conduit walls directly into or through myocardium tissue, as described below. The primary vascular targets for intravascular conduit tensioning structure embodiments of the invention are in the venous tree (i.e., great cardiac vein, middle cardiac vein, small cardiac vein, anterior cardiac veins, oblique veins, and the coronary sinus). These venous structures generally run in symmetric apposition to their arterial equivalents, albeit at spaced intervals, where most myocardial infarcts originate. As such, in anatomical areas clinically known to have a significant prevalence of coronary artery disease, such as the left anterior descending, right coronary and circumflex arteries, the associated venous structures provide ideal target locations for catheter-based, percutaneous implantation of intravascular conduit tensioning structures to provide palliation and/or therapy.

FIGS. 3A and 3B show perspective views of a diseased heart reinforced with intravascular conduit tensioning structure 4 of the invention. Tensioning structure 4 limits myocardial stretch or infarct expansion by locally reinforcing the infarcted/ischemic regions 20 or other diseased sections of tissue, and limiting the tension applied to the tissue regions 20 in conjunction with diastolic filling pressure exerted directly against this diseased section. In this example, an intravascular conduit tensioning structure 4 is shown deployed in the great cardiac vein 16 such that it targets ischemic or infarcted tissue 20 associated with an occluded or stenosed left anterior descending artery or its emanating branches. Tensioning structure 4 can also be placed directly into the artery; however, it is preferred to anchor the structure in immediately apposed veins to eliminate concerns of thrombogenicity and adverse sequelae associated with placing foreign objects into arterial structures. Alternatively, the tensioning structures can also be positioned intravascularly, but anchored to the heart by extension into or through the myocardium.

All of the intravascular conduit tensioning structure embodiments are preferably positioned and deployed such that they extend from within the infarcted/ischemic region to tissue residing within or beyond the border region of this zone, or between spaced apart, border zone regions extending through, over, or under the infarct/ischemic zones. Tensioning structure 4 are capable of applying a continuous or strain limiting tensile force to resist diastolic filling pressure while simultaneously providing a commensurate compressive force to the muscle wall to additionally or alternatively limit, compensate or provide therapeutic treatment for congestive heart failure and/or to reverse the remodeling that produces an enlarged heart.

Figure 4B:
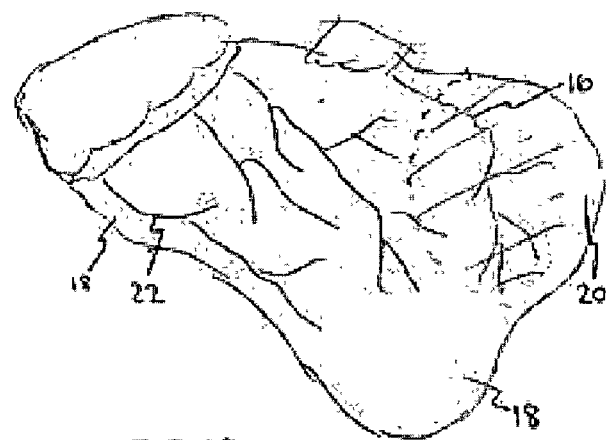

FIGS. 4A and 4B show perspective views of hearts highlighting the remodeling that occurs over time due to the inability of the ischemic/infarcted area 20 to withstand pumping pressures. FIG. 4A shows the heart with diseased tissue 20 at the onset of remodeling. Further FIG. 4B also shows the result of remodeling with an aneurysmal-like bulging of tissue outward from the ischemic/infarcted area 20. This remodeling disrupts cardiac output by producing zones of hypokinesis, dyskinesis and/or akinesis, which further exacer bates the burden on the heart. The heart tries to compensate for this remodeling to maintain cardiac output by altering the compliance, contractility, and/or heart rate; in doing so the response only accelerates or perpetuates the degeneration.

Figure 4C:
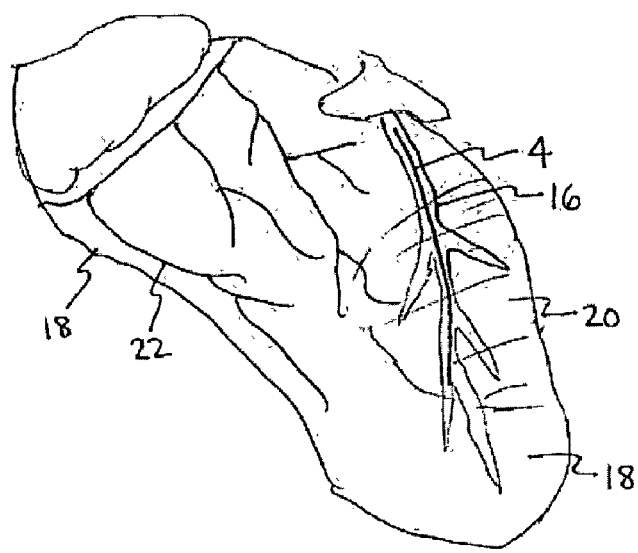
FIG. 4C shows a perspective view of the heart of FIG. 4B reinforced with an intravascular, tensioning structure of the invention.

As shown in FIG. 4C, intravascular conduit tensioning structures 4 can be secured such that they effectively cover the ischemic/infarcted area 20 and also extend across the diseased section 20 at both ends where they are anchored.

Accordingly, the tensioning structure in FIG. 4C is shown anchored in the great cardiac vein 16 providing reinforcement and treatment to the weakened region 20.

This provides sufficient reinforcement of the heart to regulate and withstand the internal forces that would otherwise perpetuate the remodeling process. In doing so, the tensioning structures 4 facilitate and maintain a more efficient and perhaps optimal, or at least more optimal, wall motion throughout the cardiac cycle, thereby aiding in diastolic filling and systolic contraction at the diseased sections of the heart 20. As such, the precursors to remodeling (such as excess strain in the weakened, diseased sections of the heart 20 during systolic and diastolic cycles) are reduced, removed and even reversed.

FIGS. 5A and 5B show an anterior view of a heart with tensioning structure 4 of the invention being percutaneously deployed from a catheter delivery system 6 into the great cardiac vein 16 and the small cardiac vein 22.

FIG. 5A also shows tensioning structure 4 being deployed within the great cardiac vein 16 and in 5B in the small cardiac vein 22. These figures again illustrate the use of the tensioning structures to provide local reinforcement to the cardiac muscle.

The tensioning structures according to the present invention can be deployed within these venous structures as a stand-alone therapy for congestive heart disease or in combination with adjunctive treatment of the valve annulus As such, it is noted that a multitude of such tensioning structures can be deployed about the heart in various, venous conduit structures, and as required anchored at various myocardial tissue positions to provide the reinforcement required to regulate and withstand the stresses and strains that would otherwise perpetuate the remodeling process. More than one tensioning structure 4 can be deployed into a single coronary vein (or other vascular conduit), into or through the myocardium associated with or adjacent to the infarcted/ischemic zone(s) of the heart, or a combination of vascular and direct myocardial approaches (described below) to vary the reinforcement pattern and effect throughout the coronary bed.

FIGS. 6A and 6B show a posterior view of the heart depicting deployment of an intravascular conduit tensioning structure 4 into the middle cardiac vein 28 and into the coronary sinus 26 to provide additional reinforcement. In FIGS. 5B, 6A and 6B, the tensioning structures 4 are shown deployed in the great cardiac vein 16, middle cardiac vein 28 and branches 30 and 38 emanating from such veins. Preferably, the tensioning structures are positioned and anchored distally prior to securing tensioning structures directly in the coronary sinus 26 because the distal most target vessel should be accessed first. However, anchoring in the coronary sinus could be deployed first if desired or required by the operator. FIGS. 6A and 6B illustrate various proximal and distal anchor configurations that are preferred for the invention. FIG. 6A depicts the distal deployment of an intravascular conduit tensioning structure 4 into the middle cardiac vein 28 and FIG. 6B illustrates deployment of the tensioning structure and proximal anchoring in the coronary sinus 26 with the distal anchoring in the left marginal vein 30.

Figure 7A:
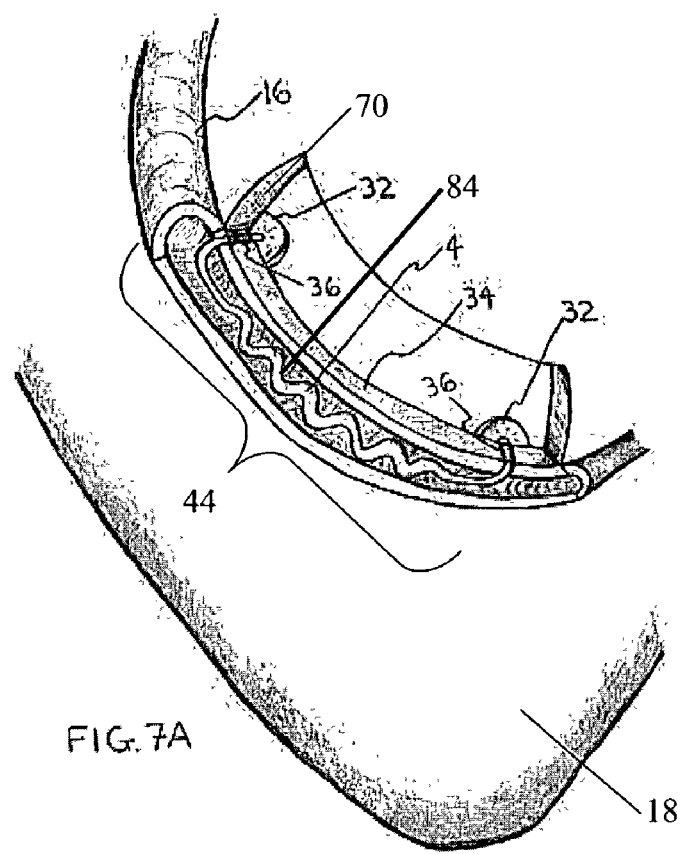
FIGS. 7A and 7B show exploded cut-away views of vessels in which a tensioning structure is placed, with each of the structures anchored transmyocardially.
Figure 7B:
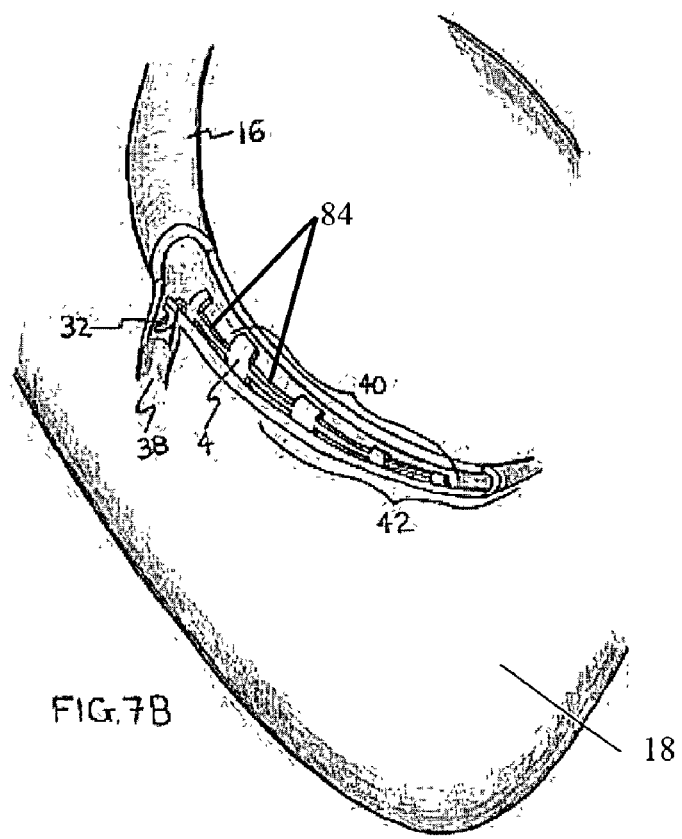

The tensioning structures can also be positioned intravascularly, but anchored to the heart into or through the myocardium. As an example, FIGS. 7A and 7B show a detailed, cut away anterior view of two tensioning structures 4 anchored to the great cardiac vein 16 at the ventricle 24. Tensioning structure 4 in FIG. 7A is shown deployed within the vein with both ends/termination secured to the vessel using anchors 32 placed transmyocardially (into or through the myocardial wall 34). The tensioning structure shown in FIG. 7A incorporates a tensile member 84 featuring an undulating sine wave section 44, which provides an elastic or spring like loading to regulate or moderate expansion of the heart during diastole. In addition, this tensioning structure 4 incorporates radiopaque marker bands 36 which facilitate evaluation of cardiac performance by allowing measurement of the distance between marker bands 36 during the cardiac cycle under fluoroscopic guidance. Alternatively, the marker bands 36 could be fashioned from an echogenic material that can be located and visualized with ultrasonic imaging guidance, or otherwise similar means.

Tensioning structure 4 in FIG. 7B is shown deployed within the great cardiac vein 16. In this illustration, anchoring is achieved by positioning within a branch vessel 38 emanating from the great cardiac vein 16 by locating anchor 32 in the said branch vessel 38. This tensioning structure also features a tapered section 40 to properly engage and deploy within a tapering vein section 42. The tensioning structure design shown in FIG. 7 radially supports a portion of the vein vessel at spaced apart intervals. This embodiment incorporates reduced diameter sections defining flexible tensile members 84 associated with radially, curved extensions designed to lock the tensioning structure to the vasculature. In an alternate embodiment (not shown) the tensioning structure could fully support the lumen of the vein, especially at spaced apart intervals. Either sort of design could be fashioned from materials or processed by various means to have sections or regions of varying stiffness customized or tailored to provide optimal performance characteristics.

FIGS. 8A to 8E show a variety of alternate tensioning structures that can limit ischemia related myocardial stretch and infarct expansion. FIG. 8A shows an embodiment where the body of the tensioning structure 4 is a tensile member body 84 (e.g., tube, ribbon, strand, or wire, which can limit elongation with satisfactory elasticity based upon the selection of material properties and cross sectional area) incorporating at least one stress distribution feature such that the tensioning structure can apply tension against tissue without damaging the contacted tissue regions. A variety of materials can be used as the tensile member 84 of the tensioning structure, including PTFE, expanded PTFE, nylon, silicone, urethane derivatives, polyurethane, polypropylene, PET, polyester, superelastic materials (e.g., nickel titanium alloy), other alloys (e.g., stainless steel, titanium alloy etc.), metal (e.g., titanium), biological materials (e.g., strips of pericardium, collagen, elastin, vascular tissue such as a saphenous vein or radial artery, tendons, ligaments, skeletal muscle, submucosal tissue etc.) other alternate materials having the desired properties, or a combination of these and other materials.

The performance of the tensioning structure depends upon and can be tailored to the desired features. For example, when column strength is required, superelastic materials or other alloys or metals are preferred tensile member bodies 84 of the tensioning structure. When pure tension is required and the tensioning structure is to be deployed through tortuous access points, more flexible materials such as expanded PTFE, polyester, or other suture type materials may be preferred as tensile members. When absorption or biological integration is desired over a period of time, biological materials such as strips of pericardium or collagen, or absorbable materials are preferred.

FIGS. 8A to 8F show a variety of alternative tensioning structures of the invention. FIG. 8A also shows anchor members 32 secured to a tensile member 84 at both ends of tensioning structure 4 to anchor the device to and within a conduit vessel. These anchor formations 32 can alternatively be used to anchor the device directly into or through myocardial tissue for embodiments where the tensioning structures are placed or deployed extravascularly using surgical access to the epicardium, or using a catheter-based approach into the left ventricular cavity to target the endocardium. Anchors 32 are preferably fabricated from biocompatible materials commonly used in medical implants including nickel titanium (especially, for self-expanding or thermally-actuated anchors), deformable stainless steel (especially for balloon-expanded anchors), spring stainless steel, or other metals and alloys capable of being deformed using balloon catheters or other expansive means, or self-expanded to secure the tensioning structure to the vasculature, myocardium, or other tissue. Alternatively, the anchors 32 can be fabricated from superelastic polymers, flexible or deformable polymers such as urethane, expanded PTFE, or stiff materials such as FEP, polycarbonate, etc.

FIG. 8B illustrates a tensioning structure 4 that can at least impart partial radial support and be anchored to a vessel with anchors 32. In this variation of the invention, spaced apart anchor members are shown interconnected by tensile members 84. The multiple anchor members aid with cinching/compression of the local tissue region(s) to reduce wall stress while mitigating over-expansion of the tissue. Also, the multiple anchors can import or help to exert an elastic recoil effect during wall motion of the heart. That is, the tensioning structure would be fixed within the vascular conduit by frictional forces imposed upon the wall to maintain position of the structure in spite of cardiac wall motion. Therefore, the frictional fit provided by the multiple anchors along with the tensile member 84 mitigates over expansion of the heart.

FIG. 8C shows a three-dimensional view of another embodiment of a tensioning structure 4 deployed in a vessel where the tensile member 84 geometry features an undulating pattern (e.g., a sine wave pattern). Such a pattern may be provided in order to offer partial radial support to a vessel by conforming to and following the shape of the vessel lumen. FIG. 8D shows another tensioning structure 4 that incorporates a tensile member 84 featuring a three-dimensional undulation or switchback (e.g., a sinusoidal pattern) that fully supports the vessel lumen. FIG. 8E shows a variation of FIG. 8C embodiment with the addition of anchor formations 32.

FIG. 8F shows an embodiment of the tensioning structure 4 configured in a specific geometry suitable for use in or about the valve annulus 108. The design in FIG. 8F features switchbacks or a waveform at its center which when deployed about a valve annulus 108 can provide additional compressive radial force to the area opposite of anchors 32.

Figure 9A:
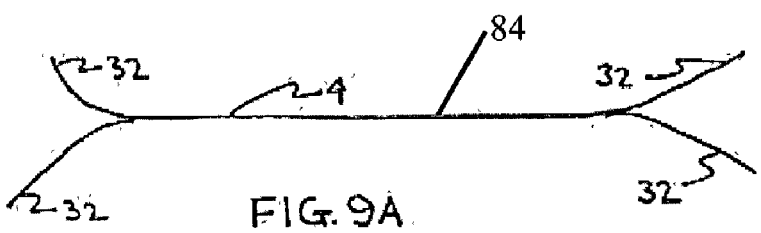
FIGS. 9A and 9B show side views of various tensioning structures adapted for anchoring in branch vessels.
Figure 9B:
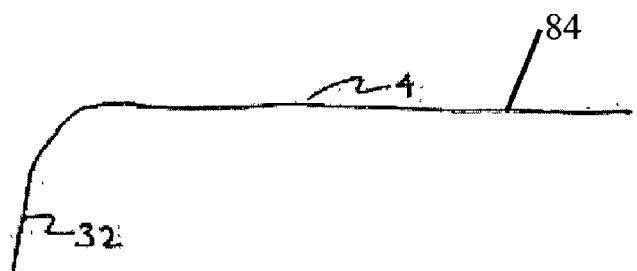

FIGS. 9A and 9B show various tensioning structures 4, adapted for anchoring in branch vessels 30. Anchor members 32 provided therewith can be of various geometric configurations to enable stabilization of the support structure 4 within the vessel to provide reinforcement to the heart, especially by leveraging the complex three-dimensional tortuosity of the vessel anatomy to facilitate or achieve fixation or anchoring.

Figure 10A:
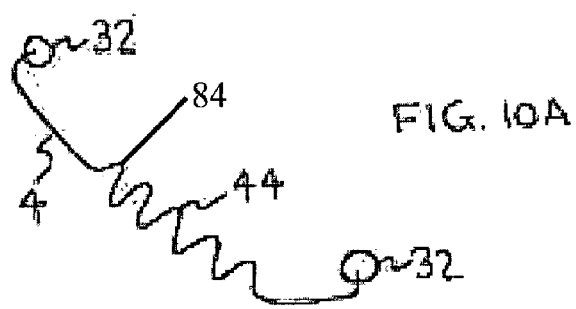
FIGS. 10A to 10C show side views of various tensioning structures that incorporate tensioning springs.
Figure 10B:
Figure 10C:

The tensioning structure embodiments shown in FIGS. 10A to 10C feature a sine wave spring section 44 within the tensile member 84 of the structure. Thereby, the tensile member embodiments in FIGS. 10A to 10C provide an additional elastic section over straight members and provide another method to optimize cardiac wall motion to improve cardiac output. In FIG. 10A, the tensile member 84 spring 44 is an undulating spiral-shape, (e.g., in the form of a sine wave). In FIG. 10B, the tensile member 84 spring 44 is a helix.

In FIG. 10C, tensile member 84 spring 44 features a geometric pattern, which enables a lower profile compression/confinement to enabling enable more efficient delivery via percutaneous or MIS means.

In FIG. 11, an embodiment of the tensioning structure variation 4 is shown, wherein the tensile member 84 incorporates individual wire, ribbon, suture, tube, or other raw material segments 48 formed so as to interlace to and with each other. The segment terminations 46 are formed about the adjacent segment members creating overlap and are curled to interfere with the curled termination of the adjacent members. At the same time, the interlaced segments 48 can expand and contract with the cardiac cycle, with the interfering terminations 46 placing a limit on the overall elongation.

FIG. 12 illustrates an embodiment of the tensioning structure variation 4 featuring a tensile member 84 with an undulating sine wave pattern (e.g., a sine wave pattern) formed along a cylindrical body. The cylindrical body shown in FIG. 12 provides complete radial support within the vessel where it is implanted. The shape also facilitates flexibility to for deployment in complex three-dimensional tortuous anatomies. Anchor formations 32 on both ends of tensile member 84 may be provided, in which case they will be oriented in a direction so as to resist the expansion of the heart when deployed within the vessel lumen.

FIGS. 13A to 13C show various, adjustable, tensioning structures 4 to provide modification or adjustability of stiffness/resistance or force outputs by incorporating means to increase or decrease flexibility of the structure. The device of FIG. 13A achieves the such adjustability utilizing removable loop structures 50 strategically positioned along the tensile member 84 that can communicate with the hub of the deployment system 6 enabling a physician operator to selectively disengage or remove the same to increase the flexibility of the structure. The device of FIG. 13B employs a ratchet mechanism 176 with spring loaded ball detents 52 along the tensile member 84 to achieve the same effect as described in 13A. The (ball) detents 52 are either resilient or spring loaded so as to selectively lock within a cut out section 54 at the distal end of the catheter deployment system 6 by engaging a push/pull mechanism moving the ball detents in a relative motion to a stationary deployment system 6 sheath. FIG. 13C, shows an embodiment similar to that in 13B, wherein the a ratchet mechanism 176 is provided that employs a sine wave-like structure instead of spring loaded ball detents to similarly facilitate adjustability.

FIGS. 14A to 14D illustrate the process of constraining a tensioning structure 4 into a deployment catheter system 6 sheath. FIG. 14A illustrates a generic embodiment of a tensioning structure 4 containing self-expanding (e.g., superelastic) components (anchor 32 and/or tensile member 84) in an unconstrained, resting geometry. FIG. 14B illustrates the initial loading of the tensioning structure 4 within or into the inner lumen of the deployment system 6 sheath using a hooked wire or: stylet 8 to pull the structure within the lumen space. FIG. 14C continues the depiction of the loading of tensioning structure 4 into the deployment system 6 sheath. Finally, FIG. 14D shows the deployment system 6 sheath with the tensioning structure fully constrained therein. For deployment within a target vessel, the process shown in FIGS. 14B to 14D can generally be followed in reverse order with the exception that the stylet 8 pushes the tensioning structure out of the sheath once it is advanced to the desired location. Alternatively, the stylet 8 can maintain the position of the tensioning structure as the deployment system 6 sheath is retracted. It should be noted that deployment of tensioning structures incorporating deformable components will be modified in that a balloon or other expandable mechanism can be used to deform pertinent components after placing at the desired implantable location. Details of deployment of at least some of the tensioning members, given the particulars of the device, may be apparent at least to skilled surgeons, interventionalists and technicians.

Deployment of these and other tensioning structures described below can be achieved 1) using a catheter-based approach to access the endocardium, vasculature, or epicardium; 2) surgically accessing the target site along the epicardium to insert and secure the tensioning structures, as described in later sections; or 3) using a combined surgical and catheter-based approach. Described below is the method and process of deploying tensioning structures into, within, or through the vasculature to reinforce the left ventricle about an infarcted/ischemic region, the mitral valve annulus to address mitral regurgitation or other insufficiencies, or other anatomy. It should be noted that this deployment process can be modified to enable positioning these tensioning structures intravascularly and then anchoring directly into or through the myocardium (or other tissue) to reinforce the anatomy without being confined to the vasculature. In addition, the deployment process can also be modified to enable positioning of . these tensioning structures extravascularly with anchoring directly into or through. myocardium (or other tissue) to reinforce the anatomy without being confined to the vasculature.

The percutaneous approach to deliver and deploy a tensioning structure is illustrated in FIGS. 6A and 6B. In these figures, an introducing sheath or guiding catheter 5, as described above, is percutaneously inserted into the right atrium 58 such that the distal end of the delivery device enters the coronary sinus 26. The delivery system catheter 6 can then be inserted through this introducing sheath such that it enters the venous system of the heart, and facilitates access to the target vessel at which tensioning/support structure 4 selected is to be deployed. The tensioning structure can take various forms such as shown in FIGS. 8A to 8E, 9A, 9B, 10A to 10C, 11, and 12 all of which can be preloaded in the deployment catheter 6 prior to insertion into the vasculature. Once the delivery system catheter 6 is positioned, the stylet 8 is held in position while the catheter is retracted. As shown in FIGS. 14A, 14B and 14D (viewed in reverse order), retraction of the catheter 6 relative to the stylet 8 causes the tensioning structure 4 to extend beyond the end of the deployment catheter 6 deploying in the target vessel as shown in FIGS. 5A, 5B, 6A and 6B. FIGS. 7A and 7B show proper securing of a tensioning structure according to the invention into a coronary vein after withdrawal of the delivery system catheter.

Various visualization features can be used to aid in proper deployment of a tensioning structure within the vasculature. A fluoroscopic marker and/or ultrasonic markers can be used to designate the side of the delivery system catheter in which the inner surface of the tensioning structure resides, thereby demarking the surface in which the tensioning structure curves.

Additional Tensioning Structure Anchor Formations

FIGS. 15A, 15B, 16A, 16B, 17A, 17B, 17C, 18A and 18B provide alternative anchor types that can be deployed into the myocardium 34 itself, or. though the myocardium and against the endocardium or epicardium of the proximate ventricle or atrium to provide interference with surrounding tissues to achieve the desired attachment. FIGS. 15C, 15D, 17D, 17E, 18C, and 18D provide additional anchor designs that can be deployed within the vessel lumen, through the vessel wall, into the myocardium, or through the myocardium and against the endocardium or epicardium or combinations thereof. In circumstances where anchor formation 32 penetrates the vessel wall in venous structures, it is anticipated that slow flow hemodynamics will cause expedient closure and clotting of the pierced area. For myocardial placements, hemostasis is maintained by the musculature tending to close around the implant anchor preventing backbleed. Common to each type of anchor is that their effect is achieved through interference with or engagement to surrounding tissues, though use of other anchoring approaches such as adhesive joints, tissue welding, and the like are within the scope of the present invention.

FIGS. 15A to 15D, 16A, 16B, 17A to 17E, and 18A to 18D show various embodiments of anchors in constrained and expanded forms or states. FIGS. 15A and 15C show a constrained anchor 32 which when expanded takes the form of a helix spiral or screw as shown in FIGS. 15B and 15D respectively. FIGS. 16A and 16B show an anchor formation 32 that features an expandable disc configuration. FIG. 16A shows a view of the disc in a constrained configuration and 16B show the expanded form of the same. The disc structure of the anchor formation in this embodiment may employ polymeric or metallic coverings attached to the anchor formation 32. FIG. 17A shows a collapsed/constrained view of a hook like wire structure that can engage tissue. Upon expansion, the anchor can take the form in FIG. 17B or 17C, the difference between the configurations of FIGS. 17B and 17C being the anchor formation 32 angle. FIG. 17D shows a hook-like structure similar to that in 17A in a constrained state with an expanded state subsequently shown in FIG. 17E. In FIGS. 18A to 18D, yet another variation of a hook-like anchor 32 is shown, in which a plurality of hooks is employment to increase the anchoring strength by distributing load among the hooks. As above these, anchor formations can be fabricated from superelastic materials to self-expand into contact with tissue structures or otherwise such as with deformable materials that require a balloon or other expanding device to deform the anchor formations into an enlarged, deployed state causing the anchor features of the anchor formations to expand into engagement with tissue structures capable of securing the tensioning structure at each end. Alternatively, the anchors 32 can be fabricated from superelastic polymers, deformable polymers, or rigid materials, depending on the anchor design and required dimensions.

Cardiac Valve Annulus Tensioning Structures

An enlarged heart can also be associated with valvular dysfunction and disorders. As myocardial hypertrophy progresses and the circumference of the heart increases, valvular leaflets can begin to separate and result in incomplete closure, incompetence and blood regurgitation further exacerbating the degenerative cycle of failure of the heart. The present invention offers a solution for this disorder by the use of the tensioning structures in vascular conduits about the annulus of the valve to apply radial, tightening forces to restore valvular function by decreasing the annulus diameter and the related stress.

Figure 22A:
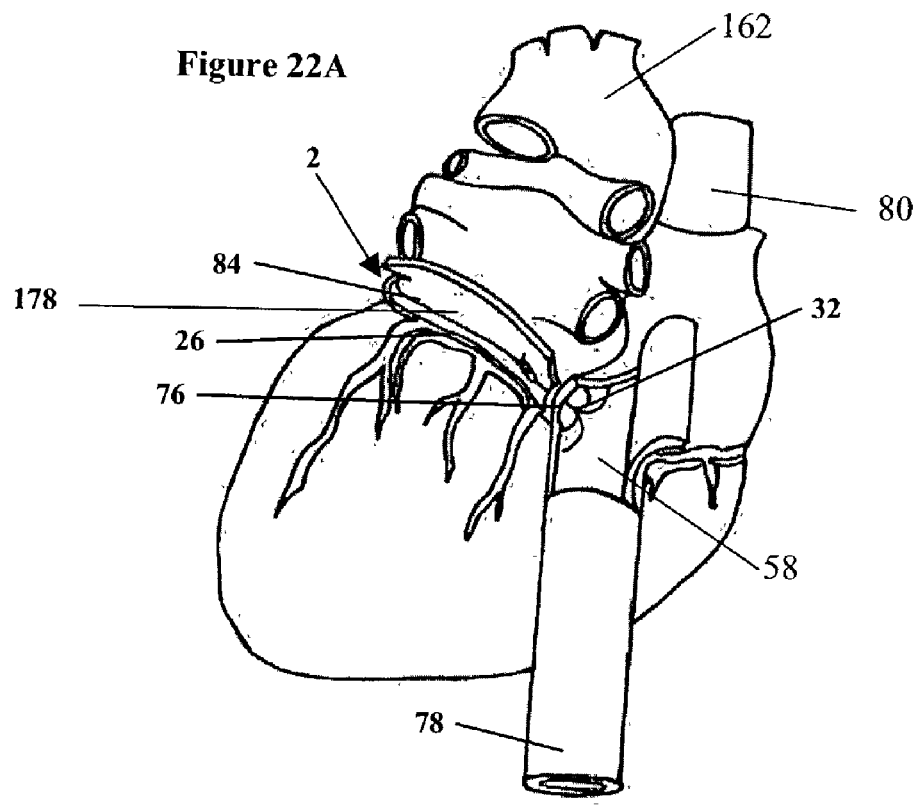
FIG. 22A shows a perspective-sectional view of a heart incorporating an intravascular, tensioning structure secured inside the coronary sinus and at the ostium of the coronary sinus in the right atrium.
Figure 22B:
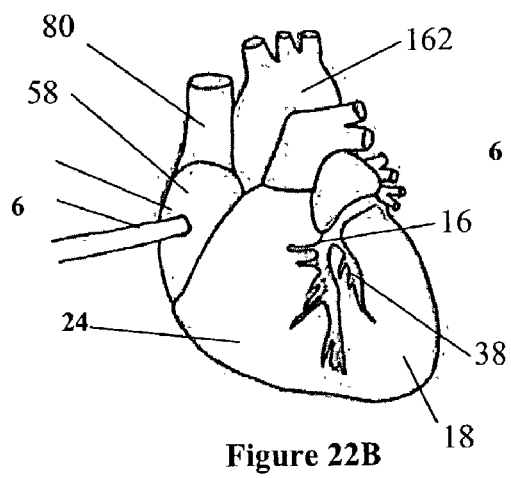
FIGS. 22B to 22F show perspective views of a heart dramatizing highlighting the process of inserting and anchoring the distal end of a tensioning structure into the coronary sinus and anchoring the proximal end along the epicardial surface of the heart.
Figure 22C:
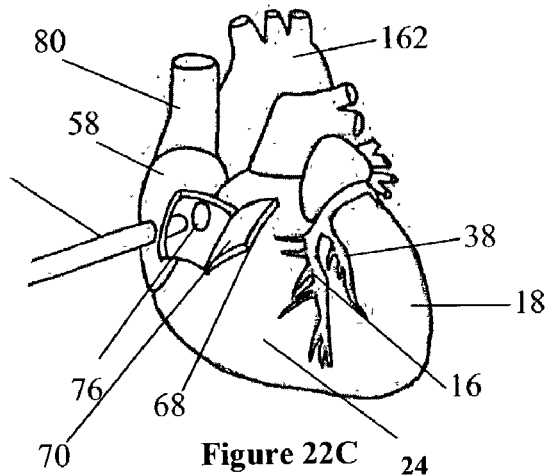
Figure 22D:
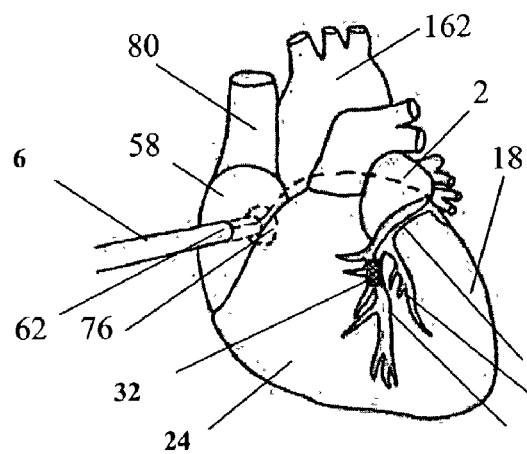
Figure 22E:
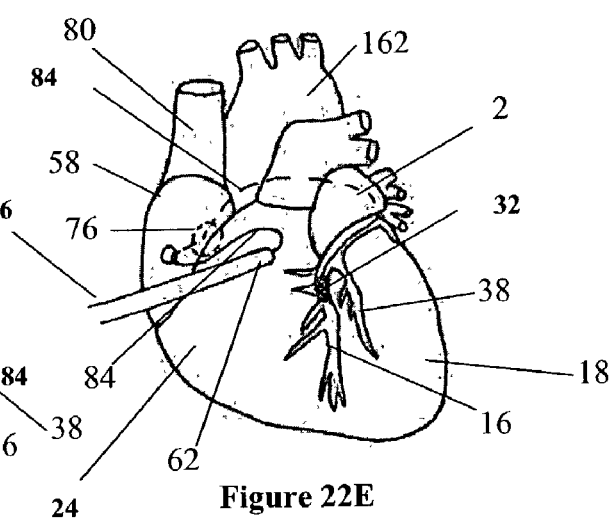

The variations of the invention described in the section are well suited for use in annulus reinforcement at the primary vascular targets in the venous tree (i.e., coronary sinus 26, great cardiac vein 16, and middle cardiac vein 28) especially since the coronary sinus anatomically navigates the atrioventricular groove 178 defining the mitral valve annulus 108 as seen in FIG. 22A. This particular target location provides an ideal location for implantation of tensioning structures to provide palliation and/or therapy. The tensioning structures described in this section are capable of applying continuous or strain limiting tensile force to resist diastolic filling pressure at the cardiac valve annulus to provide therapeutic treatment for valve incompetency, its associated detrimental role in the congestive heart failure syndrome and/or to reduce the rate of or . reverse the remodeling that produces an enlarged annulus or heart chamber.

Figure 19:
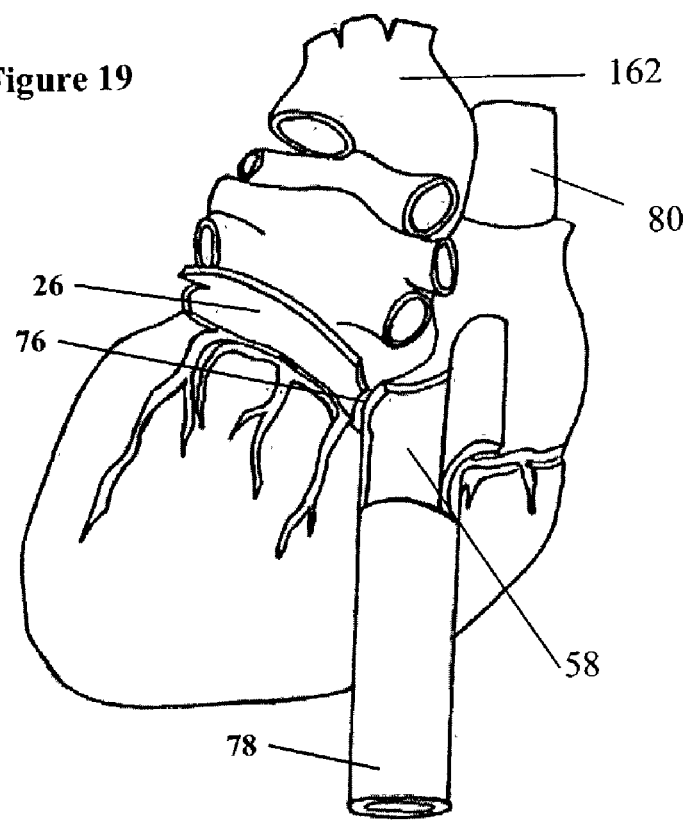
FIG. 19 shows a perspective view of a heart with sectional view of the coronary sinus and right atrium.

With initial reference to FIG. 19, a perspective view of a heart is shown with the coronary sinus 26 and right atrium 58, adjacent the inferior vena cava 78, broken in sections. The coronary sinus 26 is shown along the atrioventricular groove 178 of the heart. The coronary sinus 26 partially negotiates the mitral valve and enters the right atrium at an ostium 76 located between the inferior vena cava 78 and the tricuspid valve 180. Access to the coronary sinus 26 during percutaneous catheterization involves inserting an introducer sheath into a vein (e.g., femoral vein, subclavian, etc.) and feeding a catheter, under fluoroscopy or other imaging means, into the right atrium. An abrupt curve in the catheter, or steerability incorporated in the catheter or other separate guiding device, allows for feeding the end of the catheter through the ostium 76 and into the coronary sinus 26. From here, the tensioning structure 4 is advanced through the catheter or another guiding device, or positioned into the coronary sinus over the catheter (e.g., balloon catheter) into the desired positions within the coronary sinus (or other target vessel), and secured.

Figure 20:
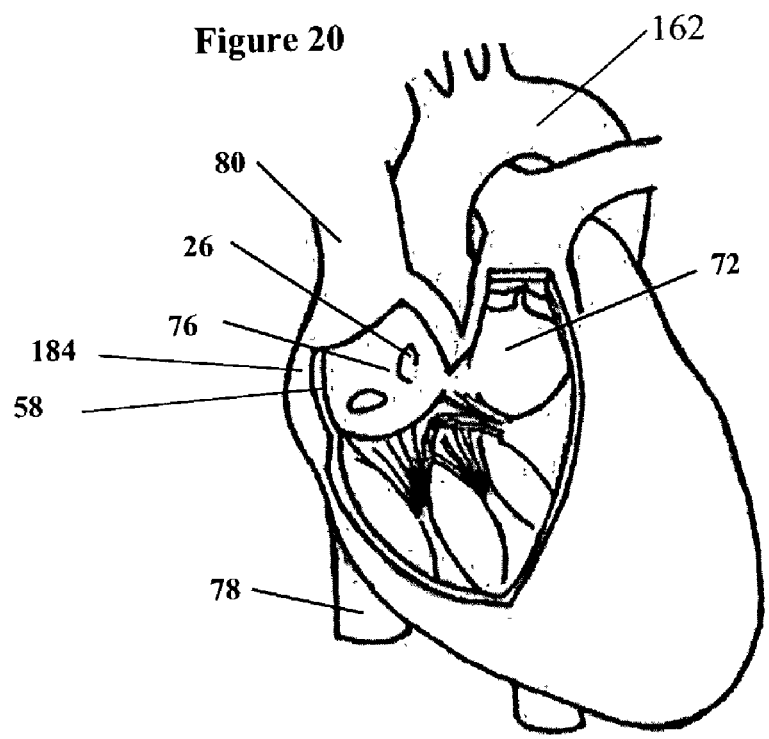
FIG. 20 shows a perspective view of a heart with sectional view of the right atrium and right ventricle.

In FIG. 20, a perspective view is shown of a heart with the right atrium 58 and right ventricle 58 shown broken in sections exposed. The right ventricular outflow tract 72 (RVOT) is shown as a potential securing location for the a tensioning structure 4. Other proximal anchoring locations include the fossa ovalis 182, the ostium 76 of the coronary sinus 26, the inferior vena cava 78, the superior vena cava 80, the right atrial appendage (not shown), the left atrial appendage (not shown), and the trabeculated tissue of the right ventricle 58. Alternatively, the tensioning structure 4 can be anchored into or through the right atrial free wall 184 or the right ventricle 24 by attaching the proximal end of the tensioning structure to the myocardium or along the epicardial surface.

Alternatively; the tensioning structure 4 can be passed through the right atrium or right ventricle, and anchored to the left ventricle or left atrium to provide further, more complete coverage of the tensioning structure around or about the mitral valve annulus. Of course, a similar approach can be used to cinch, reinforce, or repair the tricuspid valve annulus 108.

Figure 21:
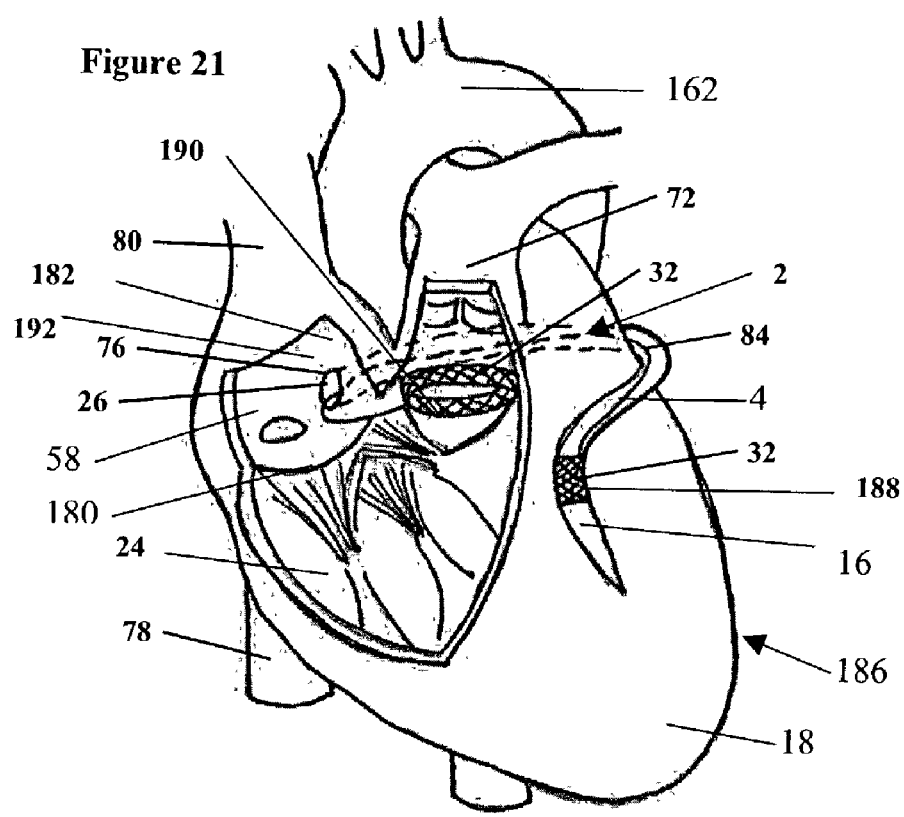
FIG. 21 shows a perspective-sectional view of a heart incorporating an intravascular, tensioning structure secured by anchor members at the coronary sinus and the right ventricular outflow tract.

FIG. 21 shows a perspective view of a heart 186 whose mitral valve annulus 108 is reinforced with a tensioning structure 4 embodiment of the invention, with the device positioned and anchored to limit expansion of the mitral valve and also to tighten the mitral valve. The tensioning structures 4 reduce radially, stiffen, and/or support the mitral valve by cinching the annulus similar to tightening as a purse-string; the tensioning structures also limit the localized forces exerted directly against the valve annulus.

In this example, the tensioning structure 4 is again shown deployed in the coronary sinus 26 such that it navigates the mitral valve annulus. The distal end 188 of the tensioning structure 4 is secured in the coronary sinus, great cardiac vein, or other branching vessel by an anchor 32, adapted for engagement to or through venous tissue, to which the tensile member 84 is secured (or integrated). The proximal end 190 of tensioning structure 4 is secured at the right ventricular outflow tract 72 (RVOT) with another anchor 32 adapted for attachment to this specific attachment site. For example, a stent anchor having a significantly larger expanded diameter can be inserted into the RVOT and expanded (using a balloon or via self-expansion) to lock the proximal end 190 of the tensile member 84.

In contrast, other annulus supports that do not extend the reinforcement device into engagement with or beyond the ostium may provide insufficient coverage around the mitral valve annulus because the attachment position and the length of the anchoring modality within the coronary sinus dramatically reduces the angular coverage around the mitral valve annulus. Instead, securing the proximal end of tensioning structure 4 to the RVOT 72 allows for reinforcing a larger amount of the mitral valve annulus since the tensioning structure is able to reinforce the valve annulus 108 from the great cardiac vein 16, along the coronary sinus 26, past the ostium 76 into the right atrium 58, along the interatrial septum 192, past the tricuspid valve 180, into the right ventricle 24, and terminating at the RVOT 72, as illustrated in solid and broken line When securing a tensioning structure to the right atrial free wall, the right ventricle, the left atrium, or the left ventricle, the guiding catheter or introducing sheath used to position the tensioning structure into the coronary sinus can be placed through the right atrium or right ventricle during surgical access to the interior of the right atrium. Alternatively, the catheter can be percutaneously placed and be advanced through the right atrial appendage (not shown) or right ventricle 24 from the inside of the chest cavity. Once the distal end of the tensioning structure is positioned and the corresponding anchoring mechanism secured, the introducing sheath can be retracted, thereby allowing the proximal end of the tensioning structure to expand into the myocardium or against the epicardium of the right atrium or right ventricle. Alternatively the proximal anchor mechanism can be manually set by deforming the same using a balloon or other expansion mechanism, as described below. Still further, the proximal anchoring mechanism can be manipulated into contact with the left atrium or left ventricle and secured, also to provide increased coverage of the tensioning structure around the annulus. Similarly, the guiding catheter or introducing sheath used to position the tensioning structure into the coronary sinus can be used to position the proximal anchoring mechanism into or through the myocardium of the right atrium or right ventricle. Additional features can be required for this approach including a puncturing mechanism to penetrate into or through the myocardium, as will be described below.

FIG. 22A shows a side view of the heart open in sections, with a tensioning structure 4 secured within the coronary sinus 26 with a distal anchor (not shown) and a proximal anchor 32 attached at the ostium 76 into the coronary sinus 26. The distal anchor can comprise one of the various anchor formations described in the preceding sections of the detailed description. As shown in FIGS. 21, 22A to, 22F, 24, and 25, the tensioning structures 4 of the invention generally extend into engagement with or beyond the ostium 76 of the coronary sinus, thereby covering the mitral valve annulus from the great cardiac vein 16 past the coronary sinus ostium 76. This significant amount of coverage provides sufficient reinforcement to the annulus to regulate and withstand the internal forces that would otherwise perpetuate the remodeling process and/or adversely affect valve competency.

Securing the tensioning structure 4 proximal end at the ostium of the coronary sinus is facilitated by a device design including a stop feature integrated with the proximal anchor 32 to prevent migration of the tensile member 84 back into the coronary sinus. This can be accomplished by a myriad of anchor member embodiments described below. These proximal anchors 32 can be, for example, plastically deformable from a small diameter to an enlarged profile (using a balloon expandable catheter) to allow positioning part of the anchor in the right atrium outside the periphery of the orifice 76 thereby acting as a stop which interferes with the atrial wall to prevent the anchor from dislodging into the lumen of the coronary sinus. Alternatively, the proximal anchors 32 can be fabricated from superelastic material capable of elastically deflecting into a low profile for deployment and returning towards a preformed shape once external compressive force is removed. This preformed shape could provide the required interference at the ostium as well.

Figure 22F:
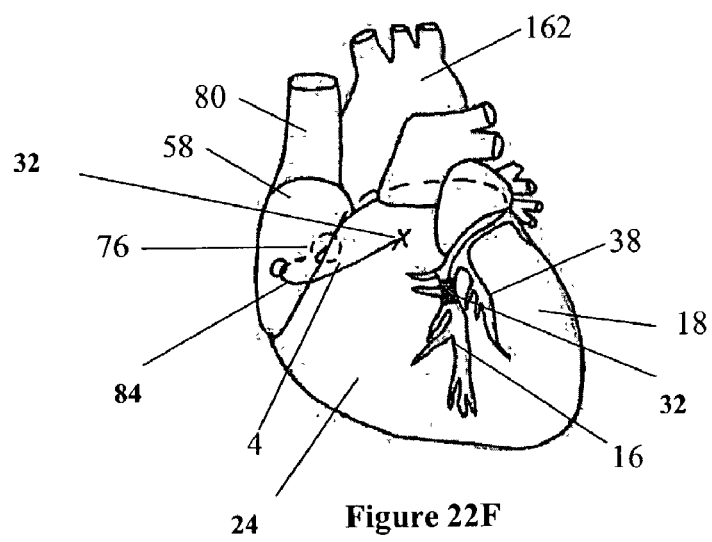

A minimally invasive surgical approach for deployment of the present embodiment is provided in FIGS. 22B to 22F. These figures show a tensioning structure 4 that has its proximal end 190 secured through the right atrium and against the right ventricular epicardium. The tensioning structure can be deployed using a catheter delivery system capable of puncturing through the right atrium 58 from inside the heart to deploy and secure the proximal anchor after positioning the distal anchor. Alternatively, as shown in FIGS. 22B to 22F, a surgical approach may be to puncture the right atrium from the epicardial surface and then place a delivery system catheter 6 into the coronary sinus. After deploying and securing the distal anchor 32, the delivery system catheter is retracted past the insertion site leaving the tensioning member 84 behind in the coronary sinus 16 and right atrium 58. A purse-string can be used to ensure hemostasis at the insertion site, around the delivery catheter during deployment of the distal anchor or around the tensile member 84 after removing the delivery catheter. The proximal anchor 32 is then engaged and secured against the insertion site 194, the right atrium 58, the right ventricle 24 (as shown in FIG. 22F), the left atrium 74, the left ventricle 18, or other anatomic structure capable of maintaining tension to the tensioning member 84. It should be noted that the same approach can be used to deploy the tensioning structure through the right ventricle 24, the inferior vena cava 78, the superior vena cava 80, or other anatomy.

Figure 23:
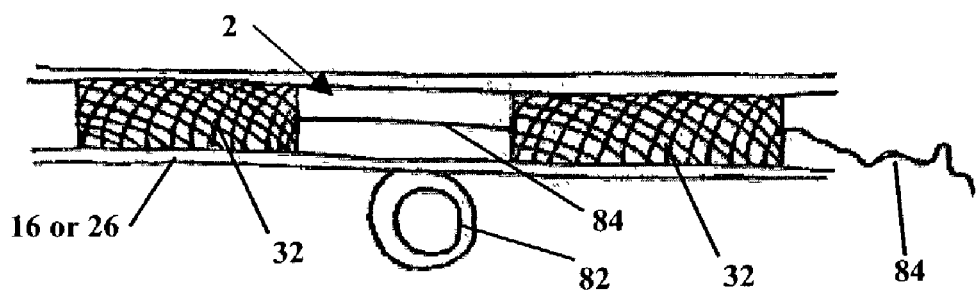
FIG. 23 shows a side-sectional view of an intravascular, tensioning structure secured within a vessel in which another vessel is located below or underneath the target/treated vessel.

FIG. 23 shows a side-sectional view of a coronary sinus 26 (or other vessel) that overlays or is otherwise in close proximity to a coronary artery (or other vessel) with a tensioning structure 4 positioned and secured within the coronary sinus. As shown in FIG. 23, the spaced apart distal anchors 32 of the tensioning structure are short relative to the length of the coronary sinus (or other target vessel) and are interconnected by the more flexible tensile member 84, so they can be positioned and secured away from the overlaying vessel 82. That way, the tensioning structure does not occlude the overlaying vessel. More than two anchors 32 can be used to further distribute the forces along the coronary sinus (or other vessel) and ensure overlaying vessels are not compromised once the tensioning structure is secured. By placing anchors on each side of the overlaying vessel 82, the coronary sinus is supported throughout this region to ensure the tightening, or compressive forces exerted by the tensile member 84 do not constrict the overlaying vessel 82.

Figure 24:
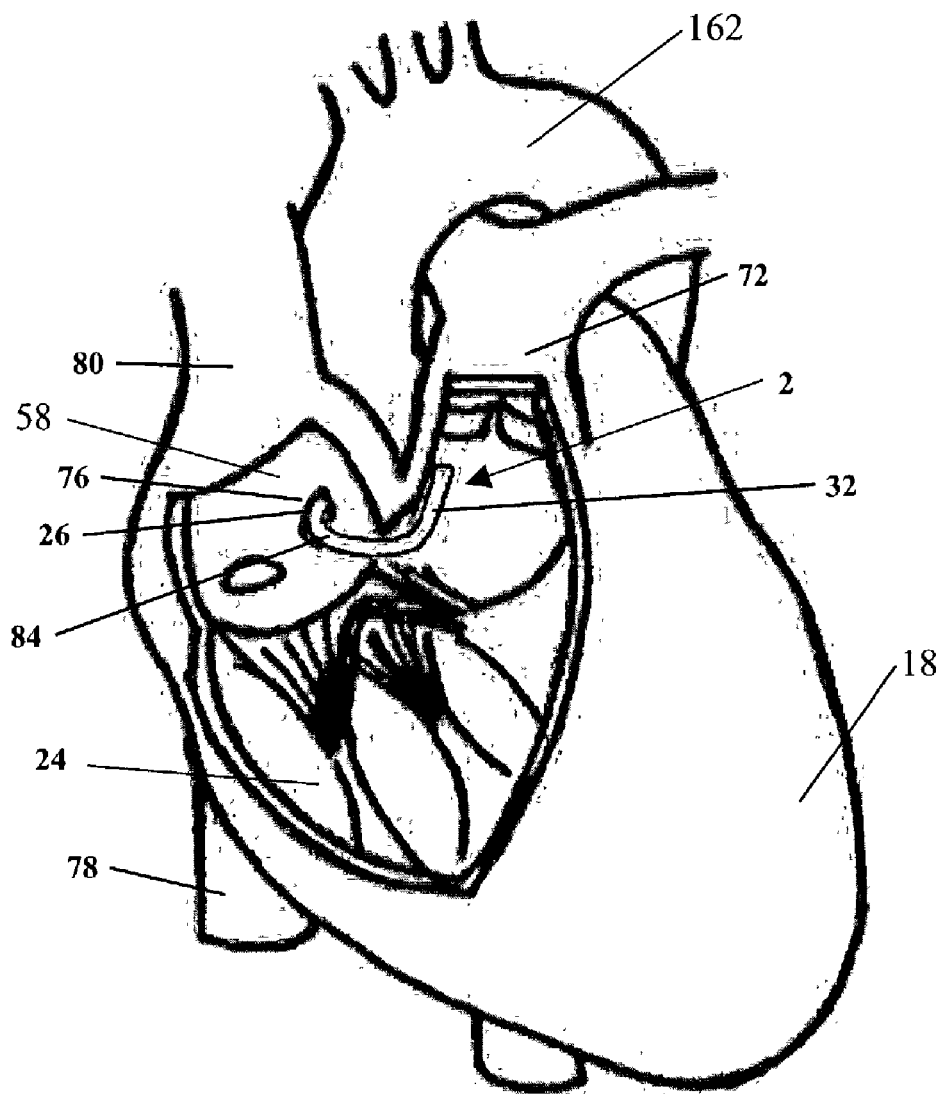
FIG. 24 shows a perspective view of a heart with sectional view of the right ventricle and right atrium showing an intravascular, tensioning structure deployed in the coronary sinus and secured on one end to the right ventricular outflow tract.

FIG. 24 shows a perspective view of a heart 2 cut away broken along the right atrium 58 and right ventricle 24 with another tensioning structure embodiment 4 deployed within the coronary sinus 26 and having the proximal anchor 32 secured to the RVOT 72. As opposed to the embodiment in FIG. 21, in which the proximal anchor 32 is fabricated as a tubular member or spiral component configured to contact the RVOT 72 throughout a cross-sectional region of tissue, the embodiment in FIG. 24 shows a proximal anchor 32 defining a hook or pigtail capable of taking advantage of the tortuosity of the RVOT 72 relative to the coronary sinus which grapples or engages onto or within the RVOT 72.

Figure 25:
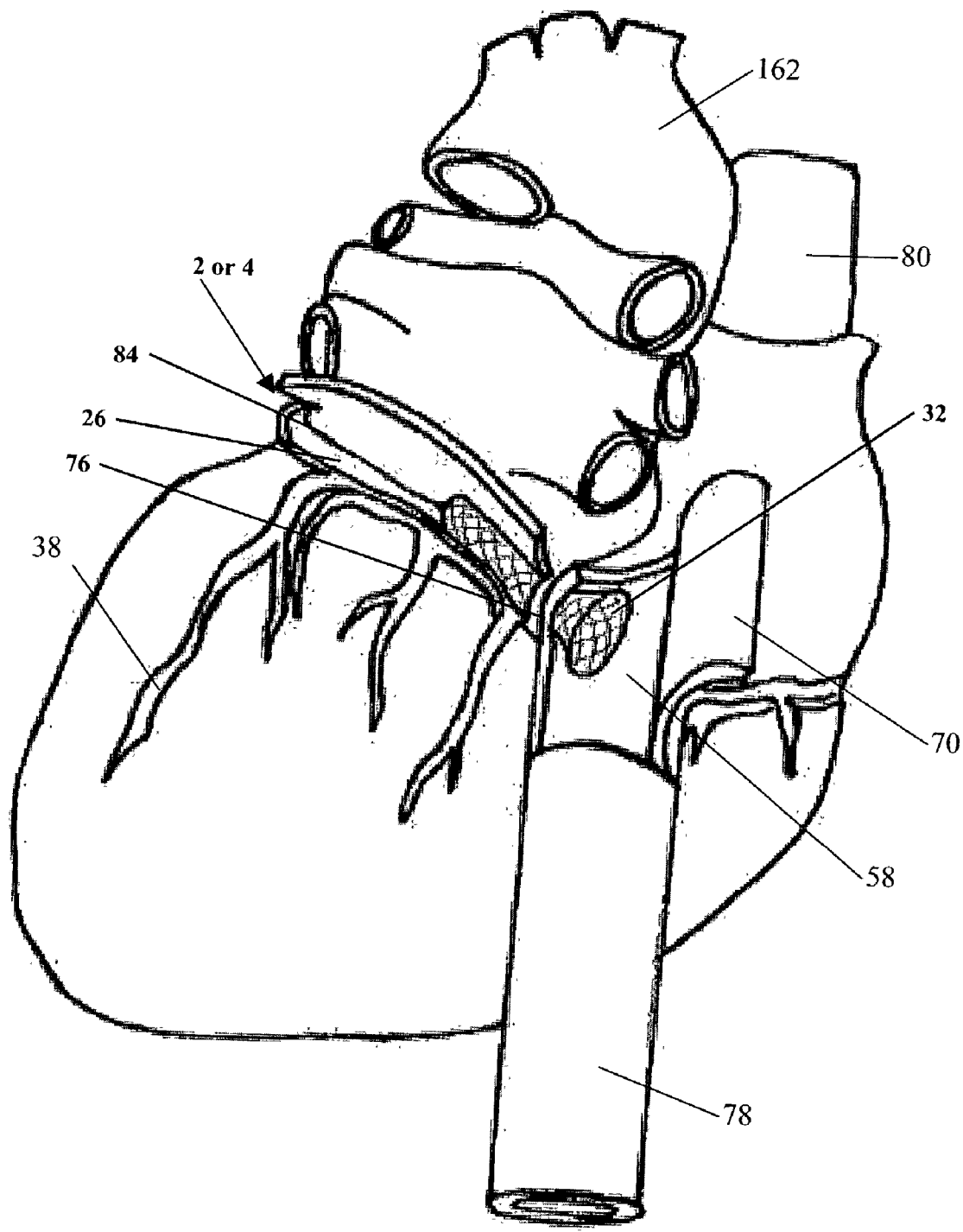
FIG. 25 shows a perspective view of a heart with sectional views of the coronary sinus and right atrium broken showing an intravascular, tensioning structure deployed in the coronary sinus and anchored on one end to the ostium of the coronary sinus in the right atrium.

FIG. 25 shows a perspective view of a cut-away heart with a tensioning structure positioned within the coronary sinus 26 and secured to the ostium 76 with the use of a balloon expandable stent (or self-expanding stent) as the proximal anchor 32. The fully expanded diameter of the stent (anchor 32) is larger than the inner diameter of the coronary sinus 26 to ensure that the stent does not migrate back into the coronary sinus 26 upon deployment. This ensures that the forces, which are applied when deploying the tensioning structure, are maintained continuously.

Such proximal anchor configurations are easy to deploy since, after securing the distal anchor, tension is applied to the tensile member 84 by retracting the proximal anchor until the appropriate tightening or cinching of the valve annulus is achieved; at this position, a balloon can be used (for balloon expandable proximal anchors) to over-expand the proximal anchor such that the region outside the coronary sinus orifice has a substantially larger outer diameter than the inner diameter at the orifice. This configuration permanently locks the tensioning structure in the plastically-deformed position. Self-expanding proximal anchors can be released from an external, compressive sheath that maintains the anchors in a compressed, low profile state during positioning predeployment. It should be noted that such proximal anchors can be configured to be used at any vessel ostium that is to be reinforced. It should also be noted that other expandable (balloon deformable or self expanding) anchor configurations can be used at the orifice with or without barbs that actively engage the interior surface of the tissue (i.e.. right atrial wall).

Figure 26A:
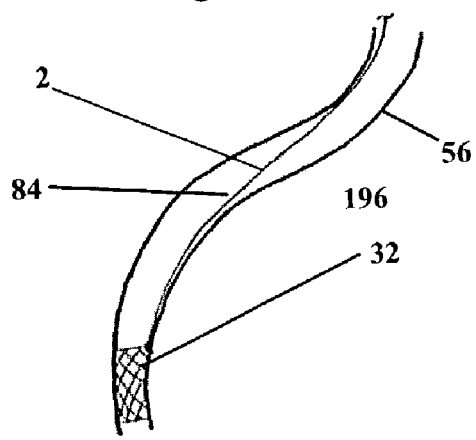
FIGS. 26A to 26D show side-sectional views of intravascularly deployed tensioning structures indicating various attachment points between tensile member and anchor components of the tensioning structure.
Figure 26B:
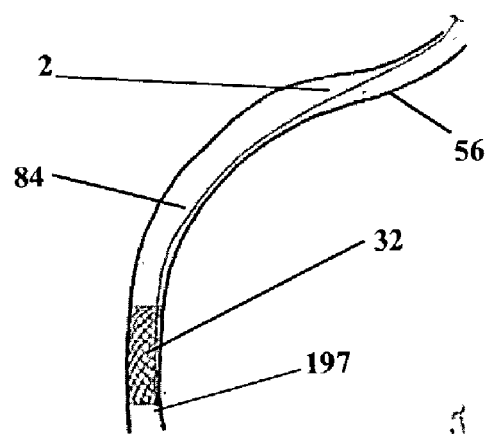
Figure 26C:
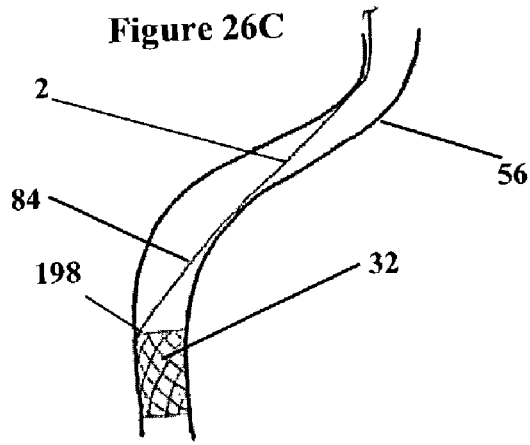
Figure 26D:
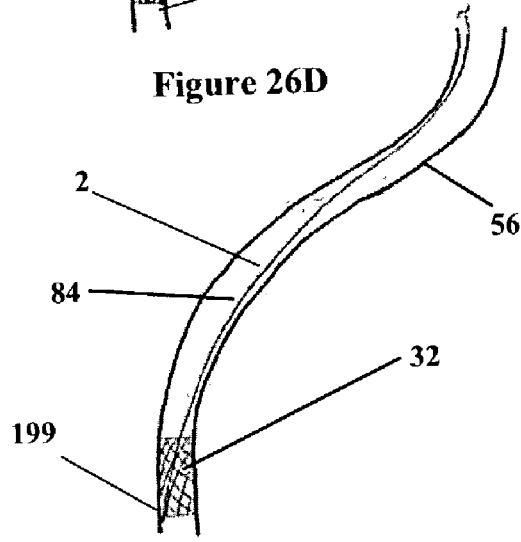

FIGS. 26A to 26D show side-sectional views of vessels 56 containing the distal anchor region of a tensioning structure illustrating various attachment points between the tensile member 84 and anchor 32. FIG. 26A shows an embodiment where the tensile member 84 is bonded to the near, inside edge 196 of the anchor 32. FIG. 26B shows an embodiment where the tensile member 84 is bonded to the far, inside edge 197 of the anchor 32. FIG. 26C shows an embodiment where the tensile member 84 is bonded to the near, outside edge 198 of the anchor 32. Finally, FIG. 26D shows an embodiment where the tensile member 84 is bonded to the far, outside edge 199 of the anchor 32. Indeed, the tensile member can be bonded to any region of the anchor 32 as required or desired. Suitable fixation methods to join the tensile member 84 to the anchor 32 include chemical bonding, tying, welding, adhesive bonding, mechanical crimping, combinations thereof or any other suitable fixation means.

When the anchor provided used is a stent like anchor formation (balloon expandable or self-expanding), as shown in FIGS. 26A to 26D, the anchor preferably has a length that is preferably more than 1.5 times the inner diameter of the target vessel (e.g., coronary sinus). Stent-like anchors are most suitable for small and medium diameter vessels, such as the coronary sinus; other anchors may be better suited for other attachment points, such as the RVOT 72. The location of the bond/attachment between tensile member 84 and anchor 32, as shown in FIGS. 26A to 26D, ensures stability of the anchor as tension is applied because tension causes the anchor to slightly rotate in the target vessel increasing the engagement of the anchor to the target vessel and preventing axial dislodgement. If the tensile forces are applied in a purely axial manner, instead of providing some torque, then the risk of dislodgment increases, but since a slight rotation is caused by tension and the length of the anchor is greater than the inner diameter, the anchor pull-out forces increases as applied tension to the anchor increases.

It should be noted that the tensile member 84 can be integrated to the anchor as opposed to being bonded or joined as separate components. For the integrated configuration, these anchors can be fabricated from one or more strands of material that form a helix, mesh, open cell, or other anchor geometry and emanate into one or more strands that produce the tensile member. For the nonintegrated condition, any anchor configuration can be bonded/attached to a tensile member to form these two components of the tensioning structure.

It will often be preferred to maximize flexibility of the tensile member 84 to aid in the traversal of tortuous anatomy in order facilitate percutaneous and/or minimally invasive surgical approaches structure of deployment. Accordingly, materials that are most suited to fabricate tensile member 84 will have a high degree of flexibility in the bending direction or, otherwise stated, have zero or minimal buckling resistance. In addition, this preferred material should have resistance to tensile elongation unless elasticity is a desired component for the tensile members, in which case, the tensile member enables temporary elongation with corresponding recoil. Materials that creep are not preferred since they might prompt the need for undesired, post-surgical tensioning structure adjustment.

FIGS. 27A to 27C show close-up views of three anchor configurations 32 and the attachment of non-integrated tensile members 84 to the anchors. FIG. 27A shows an anchor 32 formed from a mesh or braid of raw material strands and a tensile member tied to the intersection of the strands. Alternatively, as alluded to above, tensile member 84 can be glued, ultrasonically welded, spot welded, soldered, or bonded with other means, depending on the types of materials used. It should be noted that the anchor(s) 32 and/or tensile member(s) 84 can be fabricated from metallic materials such as stainless steel, nickel titanium, titanium, or other metal or alloy; superelastic polymers; biological materials such as pericardium, collagen, submucosal tissue, skeletal muscle, and vascular tissue (e.g., saphenous vein, radial artery, or other artery or vein), genetically engineered tissues; or other materials such as nylon, polyester, polypropylene, expanded PTFE, polyimide, silicone, PET, polyurethane, urethane composites, thermoplastic materials, thermoset plastics, composites of such materials, or other biocompatible material. FIG. 27B shows an anchor 32 fabricated from a tube or other raw material geometry laser cut into the desired pattern of cells and other features with a tensile member 84 bonded thereto. It should be noted that laser cutting, chemical etching, water-jet cutting, or other cutting mechanism can be used to create the anchor and the tensile member as an integrated unit from a single piece of raw material (tube stock, sheet stock, or other geometry).

FIGS. 28A to 28M illustrate various anchor 32 embodiments with attached or integrated tensile members 84. FIG. 28A shows an anchor 32 with radial protrusions to further embed the anchor into the target vessel wall and increase the pull-out forces as tension is applied through the tensile member 84. FIGS. 28B to 28F show alternative anchor embodiments with bonded or integrated tensile members 84 that incorporate radially extending elements ideally suited for the proximal anchor configured to be secured to the ostium of the coronary sinus (or other target vessel), the trabeculae of the right ventricle, the interatrial septum, the inferior vena cava, the superior vena cava, or the RVOT 72. The anchor embodiments in FIGS. 28A to 28F can also be used to secure tensioning structures 4 within the myocardium or against the epicardial or endocardial surface during surgical or catheter based reinforcement procedures where the tensioning structures 4 are positioned into or through myocardium.

FIGS. 28G and 28H show alternative anchor embodiments with attached or integrated tensile members ideally suited for attaching to any size vessel (e.g., coronary sinus 26, RVOT 72, inferior vena cava 78, superior vena cava 80, etc.), the ostium to the target vessel, the fossa ovalis, or other anatomic structure. The anchor embodiments in FIGS. 28G and 28H can also be used for tensioning structures 4 that are inserted through myocardial tissue where the anchor members abut the endocardial or epicardial surface, depending on placement location of the tensioning structures, and do not further penetrate into or through the endocardial or epicardial surface engaged to secure the anchor. FIGS. 28I to 28M show additional anchor embodiments with secured or integrated tensile member(s) suited for any size vessel. These embodiments directly engage the vessel and partially or completely penetrate into the vessel wall to secure the tensioning structure. Again, all of these anchor embodiments can be used to secure tensioning structures 4 into or through myocardial tissue for indications where the tensioning structures are used to reinforce an infarcted/ischemic zone by passing tensioning structures along or through the zone from outside the border of the zone into the region of the zone, or from opposing sides of the zone passing through the infarcted/ischemic zone.

Post placement and anchoring of tensioning structures it would be desirable to adjust the tension in the structure intraoperatively and post operatively as needed. For example, FIG. 29 shows an embodiment of the proximal anchor that incorporates a mechanism to variably tighten the tensile member 84 relative to an anchor. A ratcheting mechanism is shown with elastic balls or other teeth-like mechanisms able to retract in one-direction to increase tension applied to the tensile member 84 and prevent release of the tension applied. Such a mechanism enables variably adjustment and tightening of the annulus, or other tissue region, intraoperatively and postoperatively as the tissue heals and recovers.

When deploying tensioning structures to reinforce or tighten a mitral or tricuspid valve annulus via catheter-based approach, an introducing sheath or guiding catheter can be percutaneously inserted into the right atrium 58 such that the distal end enters the coronary sinus 26. Alternatively, the delivery system can be inserted directly through the right atrium (e.g., at the right atrial appendage) or the right Ventricle to access the coronary sinus during surgical procedures. A catheter-based delivery system approach would involve insertion through an introducing sheath positioned in the femoral vein into the venous system of the heart such that it facilitates access to the target vessel into which the tensioning structure 4 is to be deployed. The tensioning structure can take various forms as described above all of which can be preloaded in the deployment catheter prior to insertion into the vasculature.

In the preferred embodiment, the delivery system catheter is a balloon catheter capable of expanding with pressure to an enlarged diameter forcing the tensioning structure anchor (especially those with stent-like characteristics) radially outward into engagement with the interior surface of the vessel or other associated anatomy. After securing the first anchor, other anchors can be sequentially (or simultaneously) deployed with the same or other balloons.

Alternatively, the anchors can be self-expanding and constrained within a guide catheter used for deployment. A stylet or multiple stylets can be used to sequentially or simultaneously deploy the anchors as tension is applied. It should be noted that balloon expandable and self-expanding anchors can be utilized on the same tensioning structure and the deployment catheter can incorporate balloon catheters and guiding catheters collaborating to deploy the anchors at targets. Various visualization features can be used to aid in proper deployment of tensioning structures within the vasculature. For example, a fluoroscopic marker and/or ultrasonic markers can be used to designate the side of the deployment catheter in which the inner surface of the tensioning device resides; this demarks the surface in which the tensioning structure curves.

An important benefit of percutaneous approach to place and anchor tensioning structures is the ease of deployment and the rapid healing post procedure. The endovascular approach to remotely access the target sites, eliminates the need for traumatic or more invasive surgical methods to access the target structures. The incision to facilitate positioning and subsequent delivery and deployment of the support structures is minimal, most likely with only local, anesthesia, and accordingly the procedure can be conducted on an outpatient basis. The technique typically involves navigating the distal end of a catheter along a tortuous path extending along the lumens defined by the patient's vasculature between a point of entry into the patient's body and the remote target site.

It would be advantageous if the cross-sectional dimensions of such catheter or less invasive deployment system, and constrained tensioning structures could be reduced. This would ease the task of navigating such deployment systems along tortuous paths through body lumens, especially lumens having relatively small internal diameters. Minimizing the profile of the tensioning structures and deployment systems also facilitates insertion of tensioning structures described in this specification through heart tissue (myocardium) or other tissue without compromising integrity of the tissue or causing excess bleeding through the tissue.

The delivery system and process for placement of the anchors 32 can also feature means to facilitate adequate fluoroscopic visualization of vessel structures where the structure is to be positioned to ensure optimal performance. The ideal design for such a delivery system (catheter) is to include a lumen at the distal tip of such means having sufficient cross-sectional area to facilitate suitable flow rates for injections of conventional contrast media used in standard interventional catheterization procedures. The lumen exit at the distal tip can be arranged so as to communicate along the length of the catheter body such that the proximal end can be connected to manual or automatic injection means, allowing the operator to hydraulically force the contrast media through the luminal space within the catheter. The contrast can then exit at the distal end of the catheter at the luminal opening or port and flow into the blood stream. The injected contrasted would then enable kinetic visualization and mapping of the vasculature as it flows with the blood when monitored under a fluoroscope.

The ability to image at the distal tip of the deployment means is also ideal since the apposition of the anchor 32 relative to the vessel wall can be well characterized prior to application of tension. Also, the anchor 32 and the surrounding vessel wall can be assessed for damage to the wall due to catheter manipulations, deployment of the anchor 32, or damage at the anchor 32 itself.

FIG. 30 shows a cross-sectional view of a representative distal tip 86 of a delivery system catheter capable of deploying the tensioning structure, illustrating the expandable balloon 92, a balloon expandable anchor formation 32, a lumen for contrast injection 88, and a guide wire lumen 90. The lumens can be configured in various geometries using standard plastic processing techniques such as extrusion. Ideally, the guide wire lumen 90 is located at the center of the catheter to facilitate coaxial delivery of the delivery catheter over standard guide wires in the preferred embodiment. The contrast lumen 88, can be positioned to exit at the tip or cut out of the sidewall of the lumen. The contrast lumen 88 diameter should be ideally sized to allow sufficient flow rates to inject radiopaque contrast media using standard interventional technique.

Figure 31A:
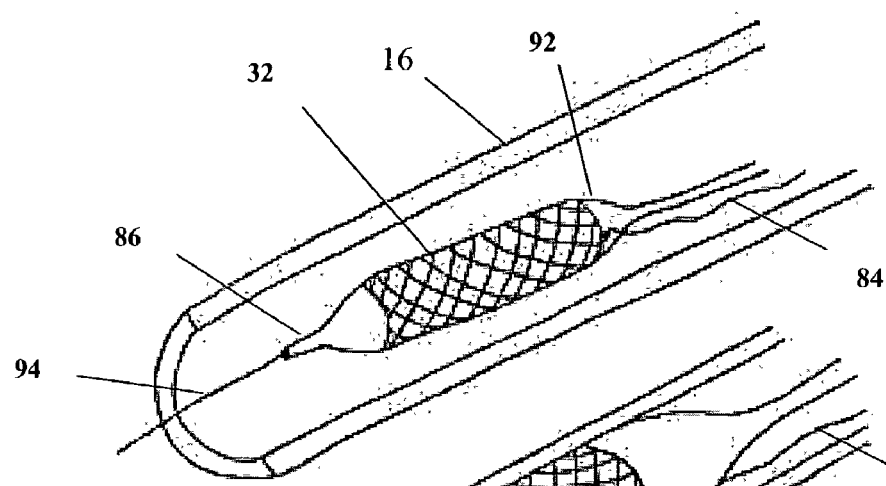
FIGS. 31A to 31C show side-sectional views of a vessel dramatizing the process of intravascularly deploying a tensioning structure comprising a deformable anchor using a balloon expandable, delivery system.
Figure 31B:
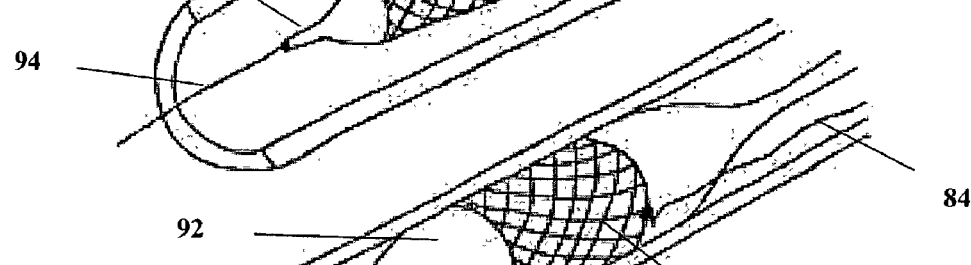
Figure 31C:
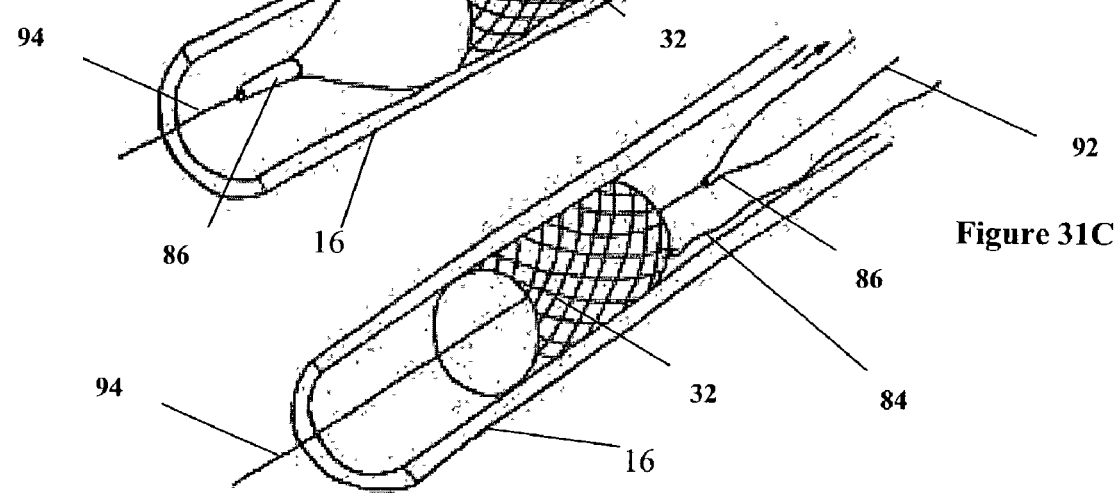

FIG. 31A shows the distal segment 86 of the delivery system catheter in a vessel prior to deployment of a distal anchor 32. The unexpanded balloon 92 with an anchor 32 crimped over its outer surface is shown traveling over a guide wire 94 to the distal vessel segment deployment target. FIG. 31B displays the expansion of the expandable balloon 92 inflated preferably with saline to deploy (i.e., plastically deform) the anchor 32 against the inner lumen of the vessel. FIG. 31C exhibits the retraction of the delivery catheter (in the direction of the arrow shown in the illustration) leaving the deployed anchor 32 behind at the vessel target location with tensile member 84 attached and extending proximal to the anchor. The tensile member 84 can be housed within the guide wire lumen 90, contrast lumen 88, a lumen of it's own (not shown), or outside the catheter to facilitate smooth, untangled delivery of the tensile member 84.

FIGS. 32A, 32B, and 32C shows the deployment of a proximal anchor 32 into the ostium of the coronary sinus located within the right atrium 76. In this embodiment, the anchor 32 is of the self-expanding variety and is shown with a retractable sheath system at the distal tip of the delivery system catheter 86. This system facilitates deployment and constraining of the anchor by the operator. In FIG. 32A, the delivery system catheter tip is shown with the tensile member 84 extending beyond the distal tip of the catheter. The termination of the tensile member is configured for attachment to a balloon expandable anchor 32 as shown in FIG. 31C or alternatively to a self-expanding anchor structure 32 as shown in FIG. 32C. FIG. 32B displays the self-expanding anchor 32 structure partially deployed in the coronary sinus 26. FIG. 32C displays the self expanding anchor structure 32 fully deployed within the ostium 76 with a flared or trumpeted end to enable mechanical lock up to fully secure the tensioning structure at the ostium.

FIG. 33A and FIG. 33B show cross-sectional areas of a coronary sinus 26 (or similar conduit) and the tensile member 84. FIG. 33A shows a smaller contact surface area 164 of the tensile member 84 to the inside wall of the coronary sinus 26 than that of FIG. 33B. A larger contact surface area 164 provides a means to reduce the stress from the loading of the tensile member 84 to the coronary sinus 26 and other adjacent venous structures to minimize the propensity for abrasion/trauma to or through the vessel wall. As such, the tensioning member 84 of the tensioning structure 4 described above can be fabricated from a rectangular or ovalized strip of flexible tensioning material such as expanded PTFE, FEP, polypropylene, PET, polyester, nylon-based materials, silicone, urethane derivatives, absorbable materials, cellulose acetate, regenerated cellulose, biological materials (e.g., pericardium, submucosal, saphenous vein, other vein or artery, skin, tendon, other collagen based material, strips of skeletal muscle, etc.). When metals or alloys are used as the tensioning member 84, they can be fabricated into a mesh, helix, sinusoid, elliptical bar, rectangular bar, or other geometry designed to distribute the stress applied to the vessel wall or other tissue structure when tension is applied to tighten the annulus or otherwise apply forces to the vessel or other tissue. Alternatively, a jacket of these same materials can be coaxially arranged over an inner tensile member component to achieve the same effect.

Figure 34C:
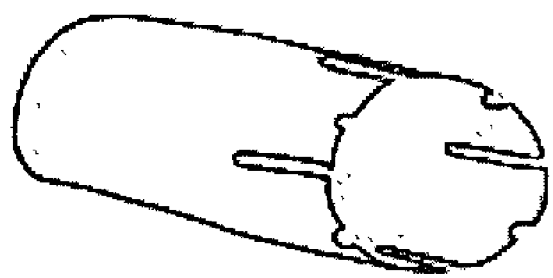
FIGS. 34C to 34E show side views highlighting fabrication steps of the locking mechanism used in FIGS. 34A and 34B.

FIGS. 34A to 34E and 35A to 35D show additional proximal anchor embodiments capable of securing the tensioning structure to the coronary sinus orifice. These embodiments show tightening capabilities described in FIG. 29 above. FIGS. 34A and 34B show a split wall anchor 166 designed to plastically deform into an expanded orientation partially within the coronary sinus and partially expanded beyond the outer diameter of the coronary sinus orifice to prevent movement or relaxation of the tensioning structure. A ratcheting or ball locking mechanism is incorporated in the side of the anchor such that as the tensioning member 84 is retracted relative to the anchor, the tensioning member becomes incrementally tighter as the locking balls or teeth are pulled into the mating latch of the anchor. This embodiment can alternatively be fabricated as a self-expanding anchor by utilizing superelastic components that transform into or maintain their austenite phase during deployment.

Figure 34D:
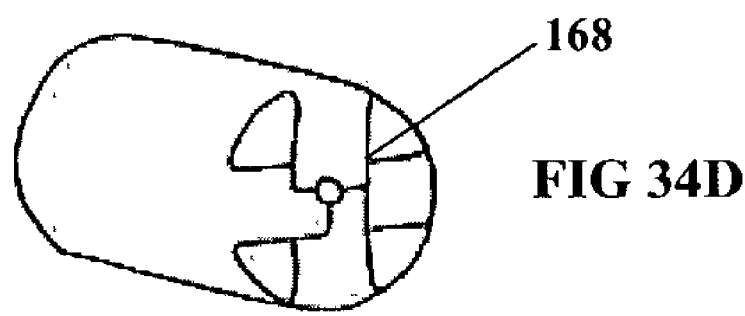
Figure 34E:
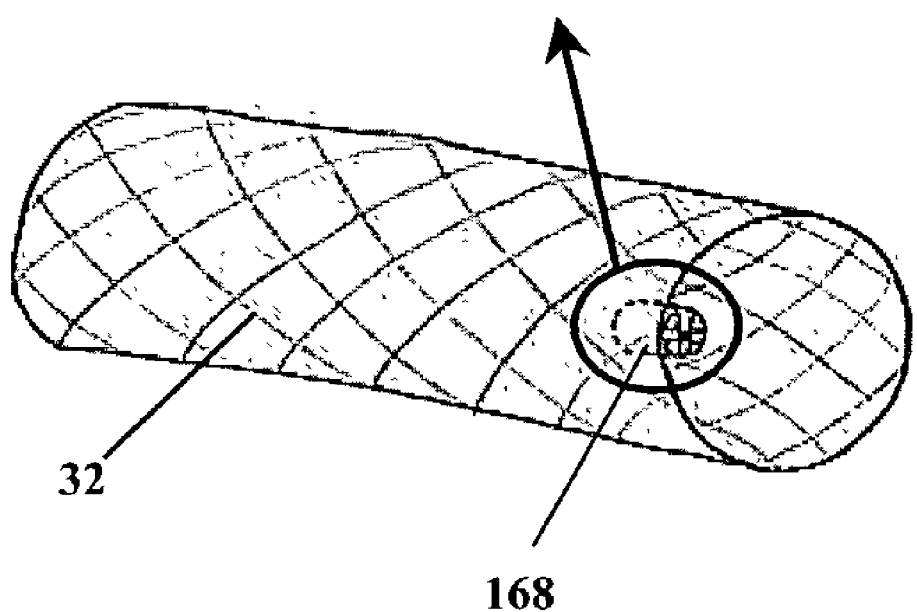

FIGS. 34C and 34D show a laser cut anchor locking mechanism pre-and post-forming. The anchor embodiment in FIG. 34E incorporates the formed locking mechanism 168 in FIG. 34D attached to the anchor mechanism, in this case a balloon expandable (or self-expanding) stent. The locking mechanism 168 in FIGS. 34D and 34E consists of radial extensions cut into the raw material as shown in FIG. 34C defining a one-way deflectable lock allows that a tensile member containing ratcheting teeth, balls, or other mechanism to move one way while inhibiting movement in the opposite direction. FIG. 34E shows the completed anchor assembly 32 which defines a mesh or open cell stent-like anchor (plastically deformable or self-expanding) capable of anchoring the tensioning structure to the coronary sinus orifice and orienting the mesh or open cell structure to produce a locking mechanism capable of engaging and restraining the ratchet teeth, balls, or other locking mechanism of the tensile members.

FIGS. 35A to 35D show another anchor embodiment capable of securing the tensioning structure to the coronary sinus orifice and incorporating a latching mechanism capable of engaging and locking mating components (teeth, balls, or other feature) of the tensile member 84 to enable manual tightening or adjustment of the tensioning structure once deployed. FIGS. 35A and 35B show a side view and a perspective view of an anchor containing a self-expanding (or plastically deformable) anchoring loop or loops 156 capable of engaging the right atrial, endocardial surface immediately adjacent to the coronary sinus orifice to prevent migration of the anchor into the coronary sinus once deployed and tension is applied. The housing that holds the anchoring loop 156 preferably constructed from a material that provides spring-like properties. The groove and slot shown in FIG. 35A and FIG. 35B would act in combination as a living hinge 154 facilitating passage of the ball detents 52 or knots 102. The inner conical lead-in 170 in combination with the living hinge 154 allows unidirectional ratcheting. FIG. 35C shows the tensile member 84 with locking features (in this case, balls 52 that engage the mating locking mechanism 168 of the anchor) being pulled through a channel to move toward the orifice thereby applying tension to the tensioning structure while preventing movement of the tensioning element in the opposite direction. FIG. 35D shows additional features of the deployment system. In this embodiment, the guiding catheter contains a channel through its side wall for the tensile member to pass such that tension can be applied through the guiding catheter whereby the distal segment of the guiding catheter can stabilize the anchor while applying the desired tension to ensure the tensioning member locking mechanism engage the mating components of the anchor. This channel through the sidewall can also incorporate a blade (movable or stationary) capable of cutting the excess tensile member after the tensioning structure is deployed and tightened in place.

The deployment systems and tensioning structures described above for reinforcing a mitral or tricuspid valve annulus can alternatively be used to reinforce infarcted and ischemic zones by positioning and securing tensioning structures intravascularly, as described previously, or directly into or through myocardium, as described below.

Myocardial Tensioning Structures

The tensioning structures 4 described above can additionally be positioned through or into myocardium to locally reinforce infarcted/ischemic zones and maintain wall motion adjacent to and throughout those zones. This aids cardiac output by increasing the left ventricular ejection fraction and wall motion throughout the heart thereby improving efficiency and reducing the effects of congestive heart failure aiding the process of reverse remodeling.

The delivery systems described above can additionally be used to insert the anchors of the tensioning structures into or through myocardium where they engage the myocardium, the epicardium, or the endocardium and attach the tensioning structures to the heart. These delivery systems can percutaneously access the desired attachment site through a catheter-based approach where a guiding catheter is passed retrograde through the aorta and into the left ventricle, transeptally through the interatrial septum from the right atrium and past the mitral valve into the left ventricle, or through the right atrium past the tricuspid annulus and into the right ventricle. With this catheter-based approach the tensioning structures are individually deployed into engagement with trabeculae or other endocardially located anatomic structures, through the endocardial surface into the myocardium, or through the myocardium where they engage the epicardial surface.

Alternatively the catheter-based or minimally invasive surgical approaches can access the epicardial surface by puncturing the right or left atrial appendage (which can be closed after the procedures), the inferior or superior vena cava, or other venous structures that can be closed readily after performing the procedure. In these cases, the tensioning structures are deployed through the epicardial surface into the myocardium or through the myocardium into engagement with the endocardium.

The delivery systems described above can also be used to deploy the tensioning structures through a thoracotomy, thoracostomy, subxiphoid access, median sternotomy or other surgical access. This way the deployment system can access the heart along the epicardium or endocardium and position the tensioning structures at the desired locations in the heart.

Many of the embodiments described previously incorporate a tensile member 84 terminating at anchor mechanisms 32 at each end. The embodiments described below are specially configured to be positioned into or through the myocardium and define anchor mechanisms augmented by the inherent structure and deployment process and/or can incorporate one or more anchors to aid in positioning and securing the tensioning structures 4 in place.

Figure 36A:
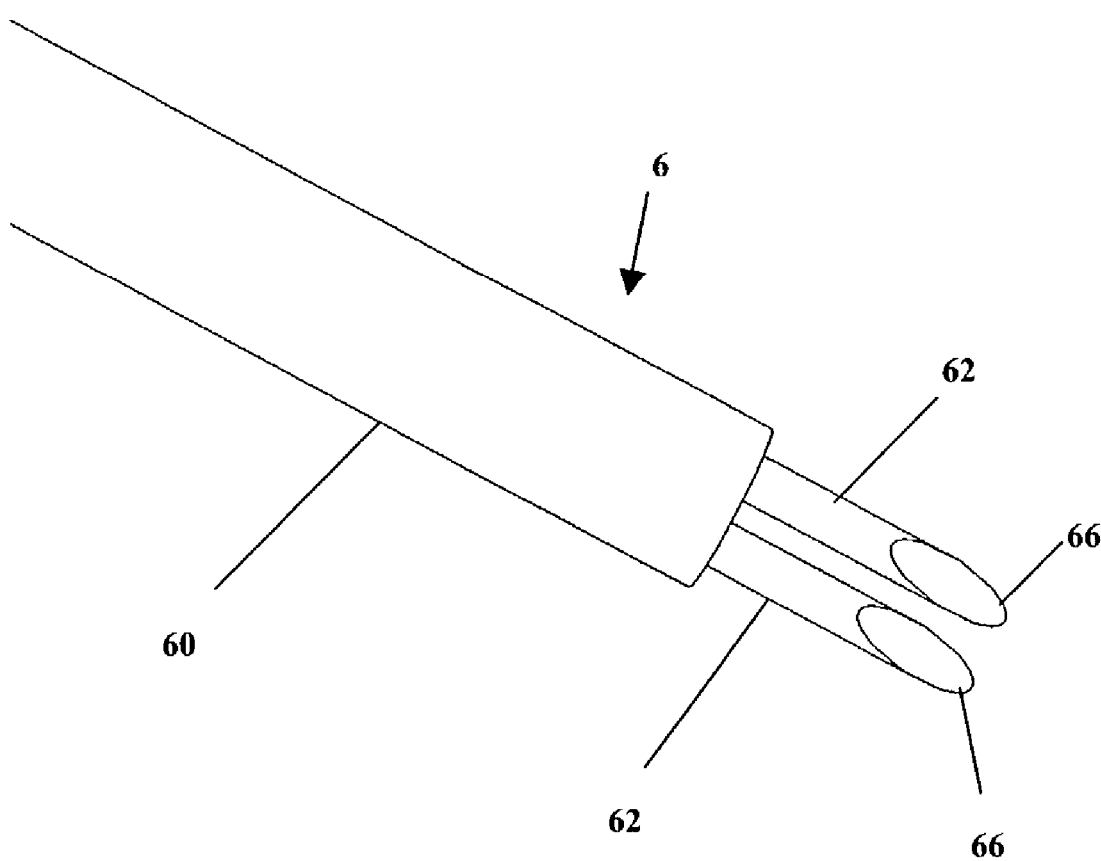
FIGS. 36A to 36D show top and perspective views, respectively, of a deployment system used to insert tensioning structures into or through myocardium.
Figure 36B:
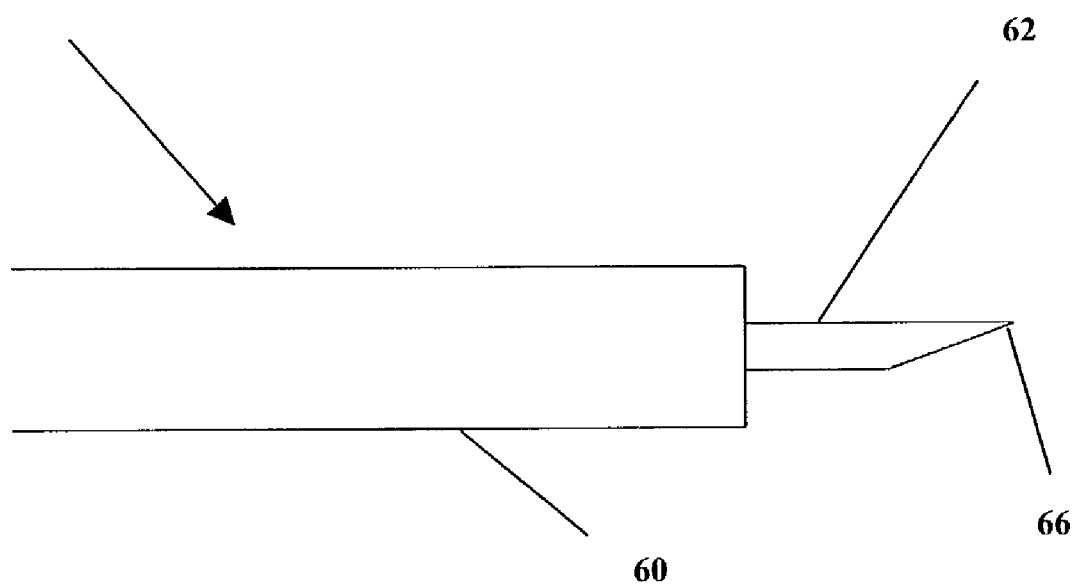
Figure 36C:
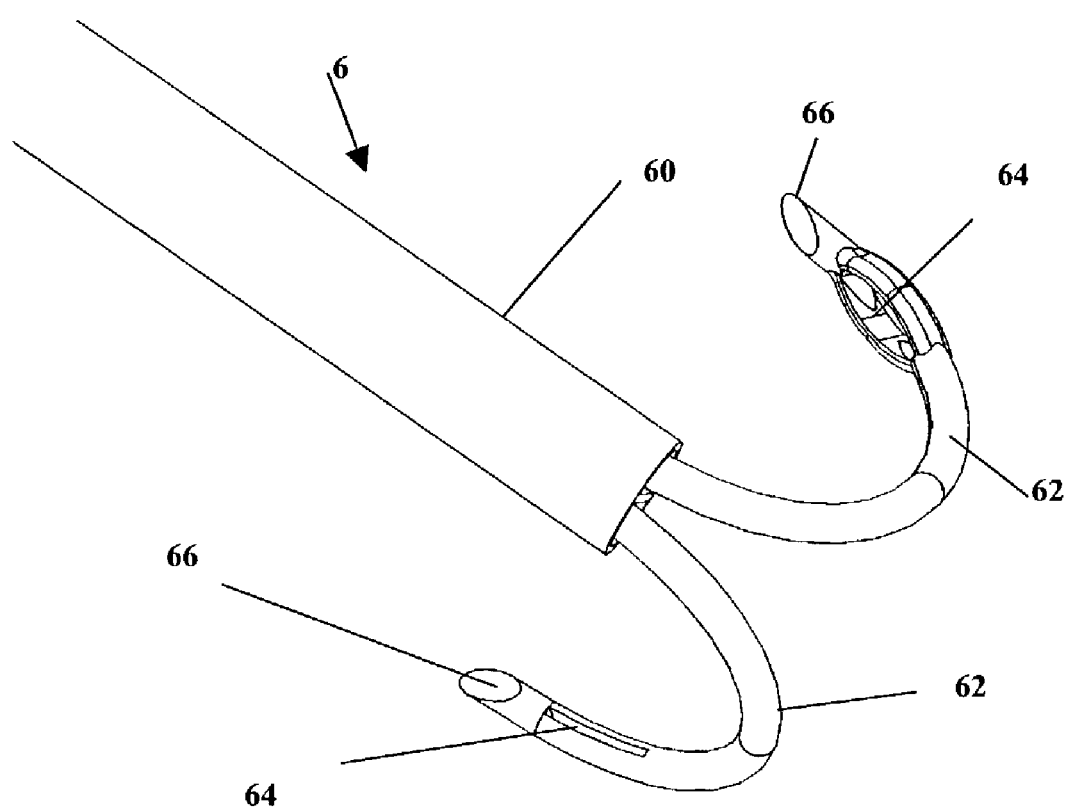
Figure 36D:
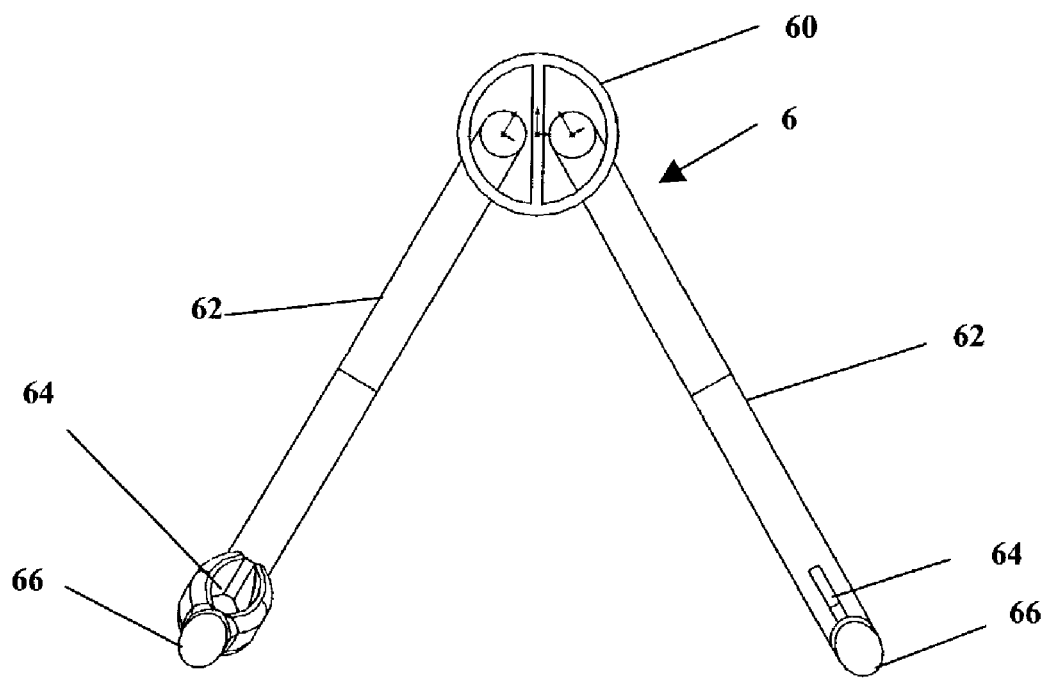

FIGS. 36A to 36D show a delivery system capable of simultaneously and/or independently inserting opposite ends or terminals of a tensioning structure through or into myocardium via a catheter-based or surgical approach. The discussion for this embodiment is described from a surgical approach initially inserting the tensioning structures through the epicardium to access the myocardium; although it should be noted that a catheter-based approach can be utilized with these embodiments if modified for percutaneous access and fluoroscopic visualization requirements facilitating insertion of the tensioning structures either through the endocardial surface to access to or through the myocardium. The delivery system embodiment shown in FIGS. 36A to 36D involves a pair of puncturing devices fabricated from superelastic materials (e.g., nickel titanium), metals (e.g., titanium) or other alloys (e.g., spring stainless steel) exhibiting sufficient elasticity and spring characteristics to compress into a low profile for insertion through a tissue surface and controllably expand as the puncturing devices are extended beyond the confines of the sheath used to apply the external force to compress the puncturing devices. The delivery system embodiment in FIGS. 36A and 36B show the puncturing devices compressed into a low profile inside a sheath (single lumen or multi-lumen with a dedicated lumen per puncturing device) having sufficient radial strength and column strength to straighten the puncturing devices. Each puncturing device incorporates a holder that engages a free end of the tensile member 84 of the tensioning structure, and advances or retracts the tensile member 84 as the puncturing device is advanced or retracted. This delivery system enables placing an independent tensile member 84 (without anchors) into or through myocardium and securing it to apply tension along an infarcted/ischemic zone to reinforce the zone. As implanted, the tensile member can contract and expand in conjunction with the wall motion about the border of the infarcted/ischemic zone.

FIGS. 36E to 36H show perspective and side views of two, 3-dimensional, cinching, tensioning structure embodiments that inherently define anchors at each end of the tensioning structure. These embodiments comprise at least one tensile member 84 (in these embodiments, only one tensile member is shown) supporting at least one stress distributing tube either secured 146 or movable 148 in relation to the tensile member 84.

As FIGS. 36E to 36H show, the stress distributing tubes, secured 146 to the tensile member 84, are located at the proximal end naturally forming a loop when opposite sides of the tensile member 84 are positioned at spaced apart insertion sites. This loop forms an anchor 96 and the secured 146 stress distributing tubes prevent highly localized stress from being applied against the tissue surface at the insertion or exit points of the tensile member 84.

Figure 36E:
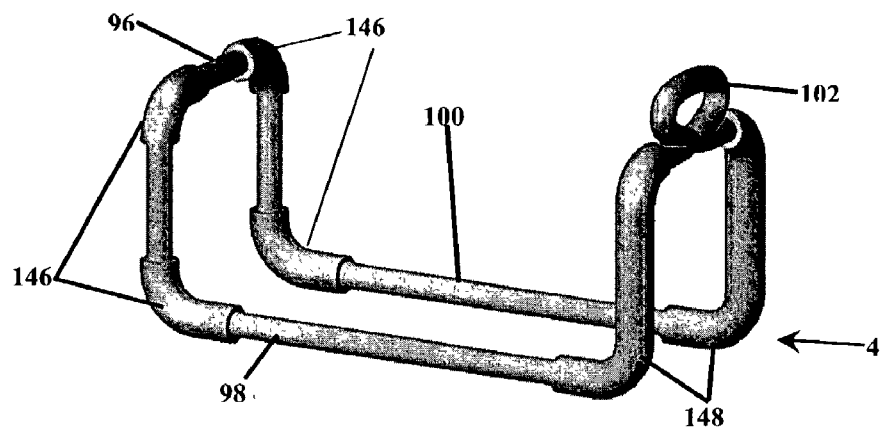
FIGS. 36E to 36H show perspective and side views, respectively, of two tensioning structures deployed into or through myocardium with delivery systems such as that shown in FIGS. 36A to 36D.
Figure 36F:
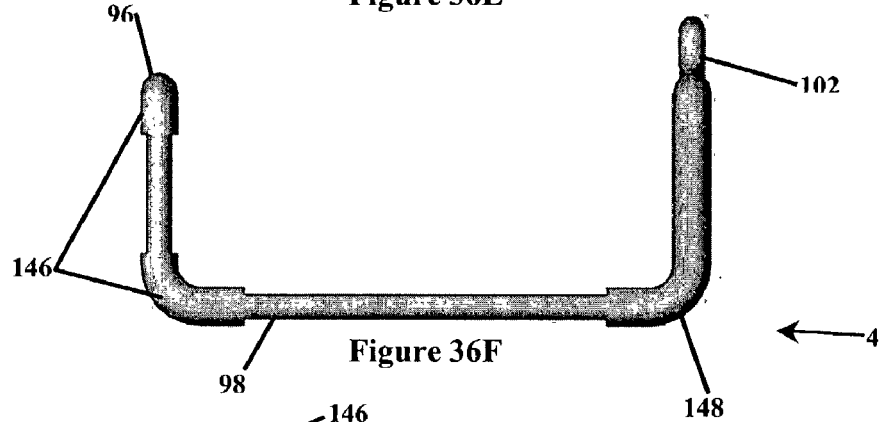

In the embodiment shown in FIGS. 36E and 36F, the secured 146 stress distributing tubes are located at the insertion sites for the proximal anchor 96 and the exit sites for the sides 98 and 100 of the tensile member 84. As such, the stress distributing tubes locally increase the stiffness of the tensioning structure at the insertion and exit sites to direct the tension applied to the tissue region between the stress distributing tubes. In addition, the secured 146 stress distributing tubes increase the surface area of the tensile member at the insertion and exit sides to distribute the force applied against the tissue along a larger surface area.

Figure 36G:
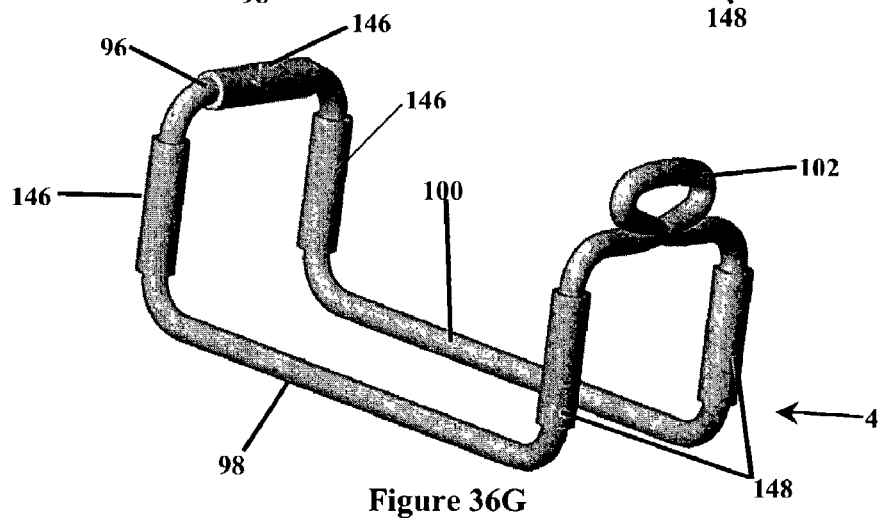
Figure 36H:
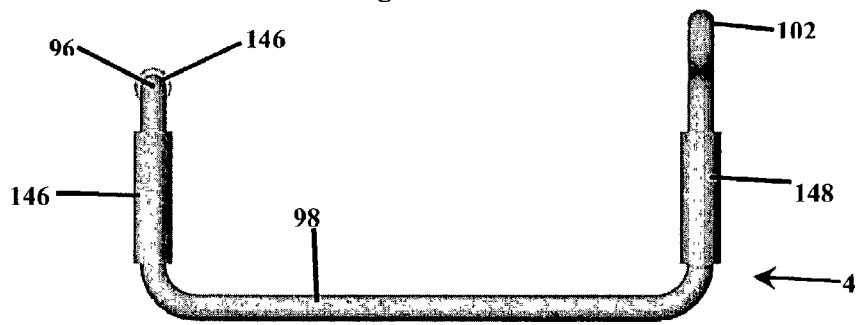

In the embodiment shown in FIGS. 36G and 36H, the secured 146 stress distributing tubes are located along the proximal anchor 96 and between the insertion and exit sites to regulate the amount of cinching, upon applying tension to the tensile member 84, along the plane defined by the length of the proximal anchor 96 loop and the plane defined by the space between the insertion and exit sites; two of the three planes defined by the 3-dimensional cinching tensioning structure. The third plane is defined by the relationship between the secured 146 and movable 148 stress distributing tubes. In this embodiment, the secured 146 stress distributing tubes limit the cinching and can vary the ratios of cinching along each plane by changing the cross-section thickness, the material type, the length of the tubes, or other parameter capable of making the tubes more flexible or rigid.

The secured tubes 146 can be fabricated by injection molding, extruding, ultrasonic welding, adhesive bonding, or by mechanically securing a covering over the tensile member 84 at defined locations. The secured tubes 146 can comprise a tubular, elliptical, rectangular, or other cross-sectional geometry. The secured tubes 146 can consist of materials such as expanded PTFE, silicone, cellulose acetate, regenerated cellulose, polyester, polypropylene, nylon-based materials, urethane or its derivatives, biological tissues (e.g., vessels, collagen based tissue structures, etc.), metals, alloys, other material capable of distributing stress over a length of the tensile member, or a composite of such materials.

The movable 148 stress distributing tubes can be fabricated with the same processes, parameters, and materials as the secured 146 tubes described above provided, the tensile member 84 can be pulled through the movable 148 stress distributing tubes. After placing the free ends of the tensile member 84 through myocardial tissue and pulling the free ends beyond the tissue surface, the movable (148) stress distributing tubes can be advanced over the tensile member 84 and positioned into the myocardial tissue. Once the stress distributing tubes are positioned, the tensile member can be tied into a knot 102 to compress the tissue region throughout the defined 3-dimensional region. The movable 146 stress distributing tubes can also comprise additional features such as flared proximal ends to abut the tissue surface to ensure hemostasis at the insertion and/or exit sites, and internal gaskets also to ensure hemostasis once a tensile member is advanced through a tube.

In the embodiments shown in FIGS. 36E to 36H and described above, the secured 146 and movable 148 stress distributing tubes prevent excess reduction or compression in the myocardial wall thickness upon application of tension to the tensioning structure. As such, the three-dimensional cinching tensioning structure is capable of compressing the region of myocardium along the tissue surface to reverse the remodeling effect and support the tissue region without applying excess force along the plane defined by the thickness of myocardium.

The three-dimensional, cinching, tensioning structures described above also exhibit required features to ensure the appropriate amount of compression against the tissue region is applied without tearing or damaging the tissue. A simple suture defines a highly localized stress concentration; especially at the insertion and exit puncture sites capable of cutting and severely traumatizing the tissue. In addition, a simple suture does not regulate the amount of compression applied along each of the three planes defined by the three-dimensional, cinching, tensioning structures; as such the myocardial wall thickness can be dramatically and undesirably reduced upon tightening without applying the desired compressive forces.

Figure 37A:
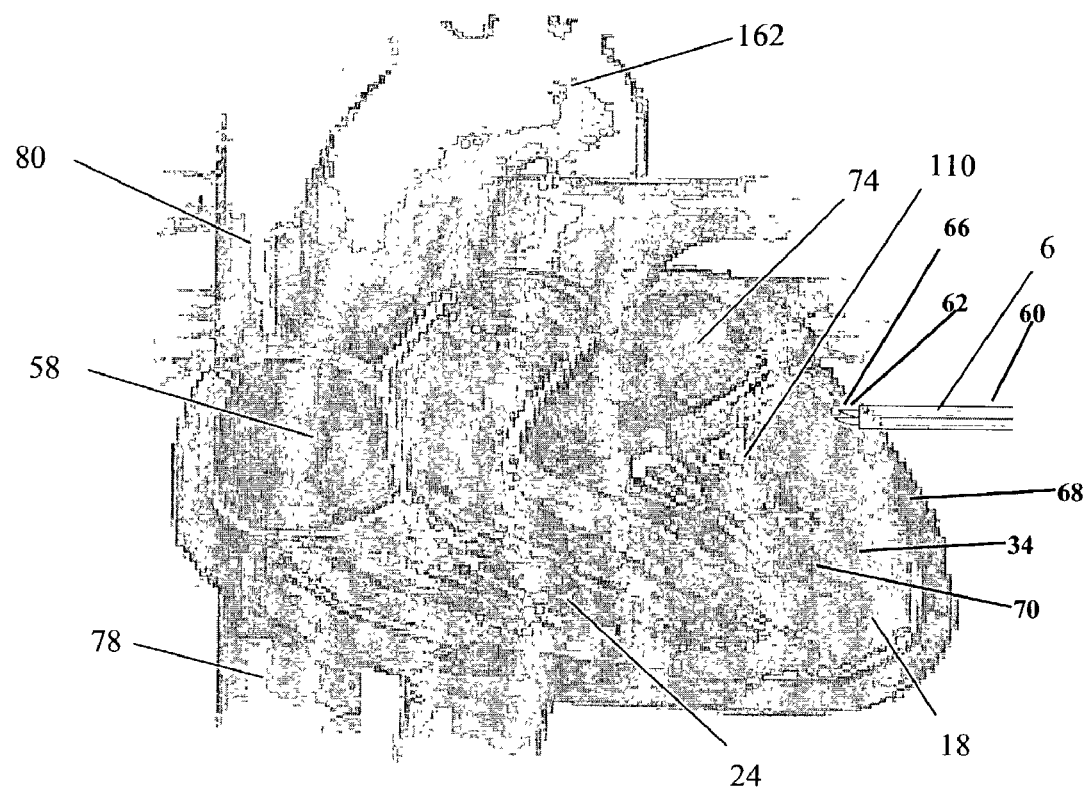
FIGS. 37A to 37C show cross-sectional views of the heart broken in sections with the deployment system of FIGS. 36A to 36D inserting the tensioning structures of FIGS. 36E to 36H into/through the myocardium.
Figure 37B:
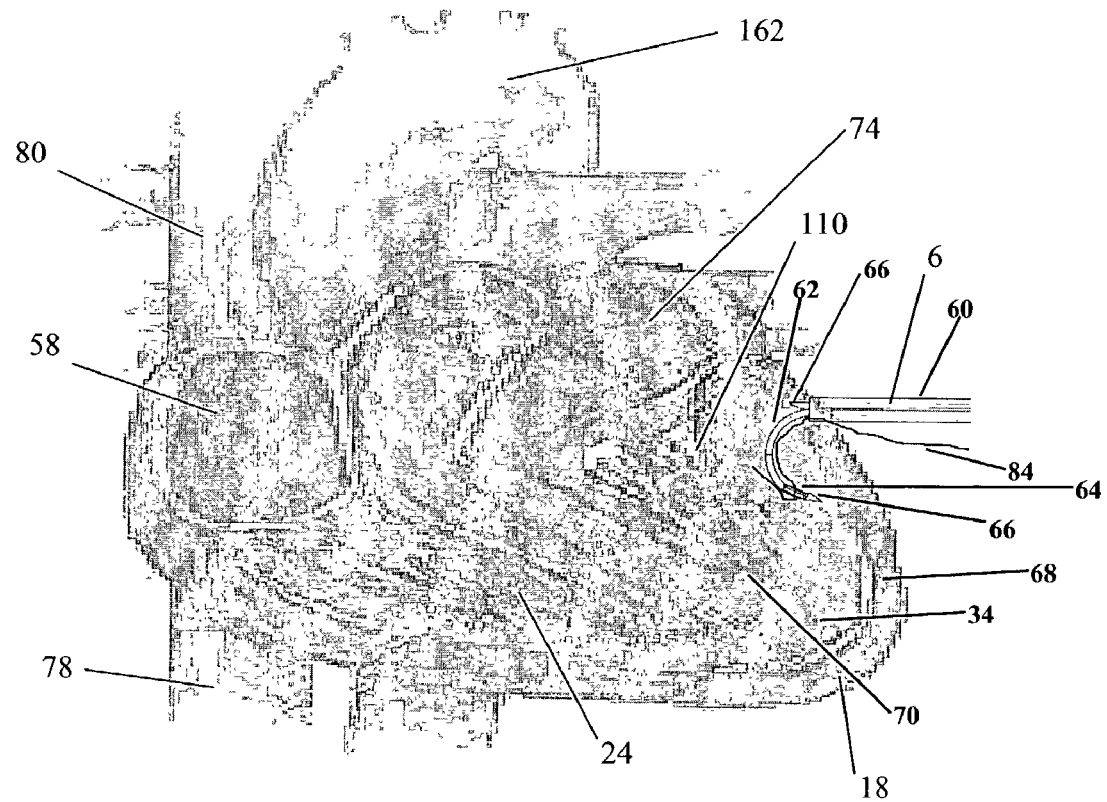
Figure 37C:
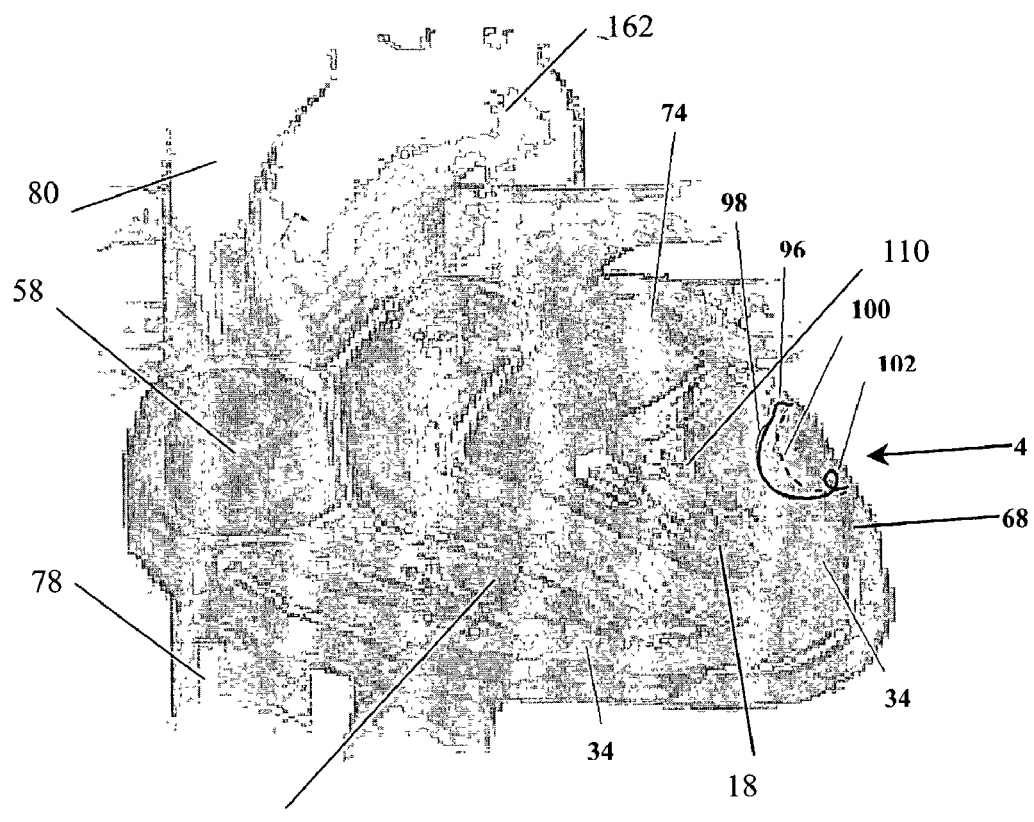

FIGS. 37A to 37C show the steps of placing a tensioning structure 4, such as shown in FIGS. 36E to 36H, through myocardium using the delivery system shown in FIGS. 36A to 36D. Each free end of the tensile member is placed through a holder 64 of a puncturing device and the puncturing devices are compressed inside the deployment sheath. In the minimally invasive surgical approach, it is preferred that the two puncturing devices are placed in contact with the epicardial surface as shown in FIG. 37A (or alternatively can be placed into contact with the endocardial 70 surface for catheter-based or open surgical procedures). The puncturing devices are designed to penetrate the epicardium with sharpened or beveled tips 66 at spaced apart intervals. Prior to inserting the puncturing devices, the tensile member 84 can be placed through a pledget 118 or other atraumatic surface (e.g., an ePTFE patch, polyester patch, other synthetic patch, a piece of pericardium, muscle or other tissue) to add additional support at the anchor and provide additional strain relief to the underlying tissue once the tensile member is tightened, not shown. As FIG. 37B shows, the puncturing devices 62 are advanced through the deployment sheath 60 at which time they expand toward their preformed configuration channeling through myocardium to define a space for the tensile member to pass. Alternatively, the puncturing devices 62 can pass the tensile member 84 from the epicardial surface through the myocardium, past the endocardium, along the endocardium, and back to the epicardium. Once the puncturing devices have advanced the ends of the tensile member through the heart wall and back past the epicardium, the ends of the tensile member are removed from the holder and the puncturing device is subsequently removed from the heart. The free ends of the tensile member are then tied together thereby tightening and compressing a region of the heart wall. Again, prior to tightening the free ends of the tensile member, they can also be inserted through pledgets 118 or other atraumatic structure to provide additional support and strain relief at the tissue puncture sites. FIG. 37C shows a heart with sections cut-out and a tensioning structure 4 placed through the myocardium. The solid line demarcates the tensioning structure on the surface of the heart wall or along the cut-out section of the heart wall and the dotted line demarcates the tensioning structure section positioned through a spaced away section of myocardium. The tensioning structure passes through the myocardium along two spaced apart lines thereby producing a 3-dimensional cinching mechanism capable of tightening the heart wall in three planes, (a) along the insertion line through the myocardium, (b) between the insertion points defined by the spacing between insertion points through the epicardial 68 surface and into the myocardium and between the exit points the tensioning structure traverses prior to tightening into a knot, and (c) along the myocardial wall thickness. The ratio between these tension parameters (i.e., a, b, and c above), in terms of the length of the insertion line and the spacing respectively, the stress distribution ratios defined by the secured 146 and movable 148 stress distributing tubes, and the magnitude of the tightening force applied to the tensioning structure defines the applied load to the heart tissue. This applied tensile load thereby also defines the degree of tightening of the heart wall in the axial (from the annulus to the apex), lateral, and vertical directions respectively and can be adjusted to custom tailor the reduction in volume of the infarcted/ischemic zone. Furthermore, the tension can be adjusted as required to alter the wall motion of this zone to better match that of adjacent myocardium. Also, it is noted that these tensioning structures can be oriented at other angles relative to the heart thereby defining different tensioning planes, and the tensioning planes do not have to extend perpendicular to one another.

The tensile members 84, and secured 146 and movable 148 stress distributing tubes of tensioning structure embodiments deployed into the 3-dimensional, cinching pattern, as shown in FIGS. 36E to 36H, 37A to 37C and described above, can consist of expanded PTFE, polypropylene, urethane derivatives, silicone, nylon, polyester, biological materials (e.g., pericardial tissue formed into strips, vascular tissue such as saphenous veins maintained in tubular form or cut into strips, submucosal tissue formed into strips, or other collagen or elastin based tissue structure), genetically engineered tissue formed into strips, metals (e.g., titanium), alloys (e.g., stainless steel, nickel titanium, etc.), polymers, or other material formed into a line, strip, tube, rod, bar, or other geometry.

Figure 38A:
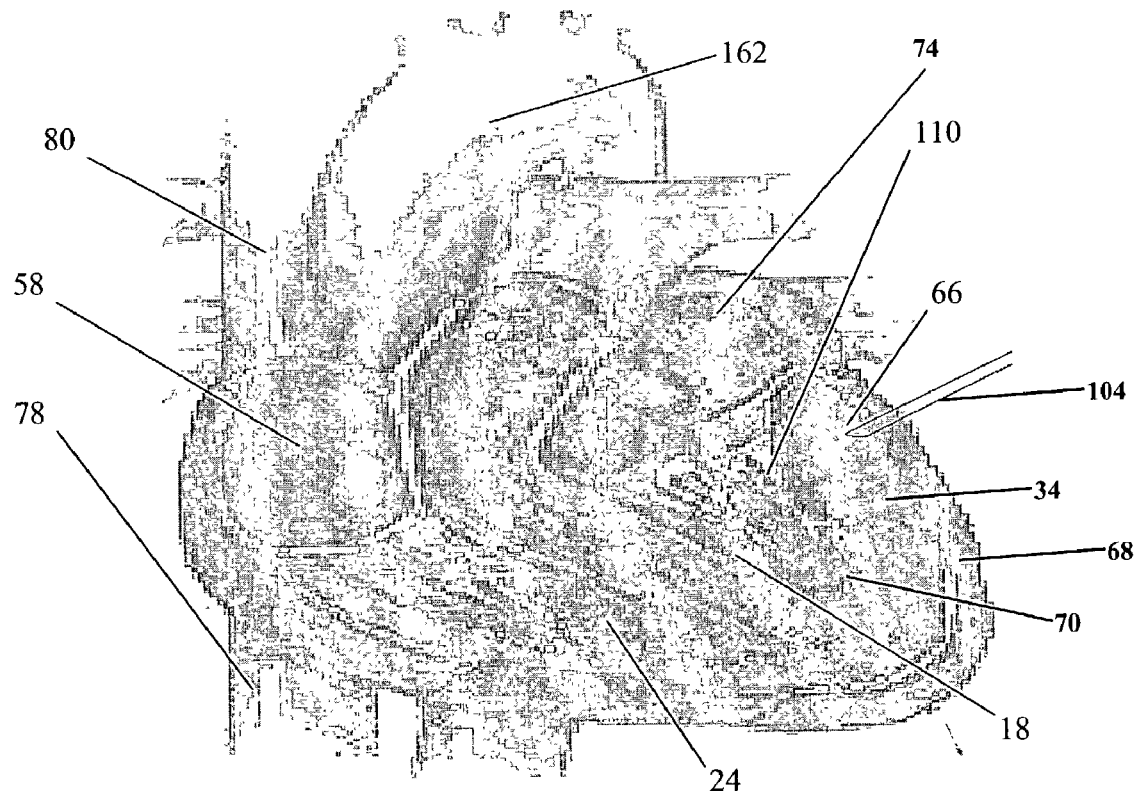
FIGS. 38A to 38C show cross-sectional views of the heart broken in sections with an alternative deployment system used to insert the tensioning structures of FIGS. 36E to 36H into/through the myocardium.
Figure 38B:
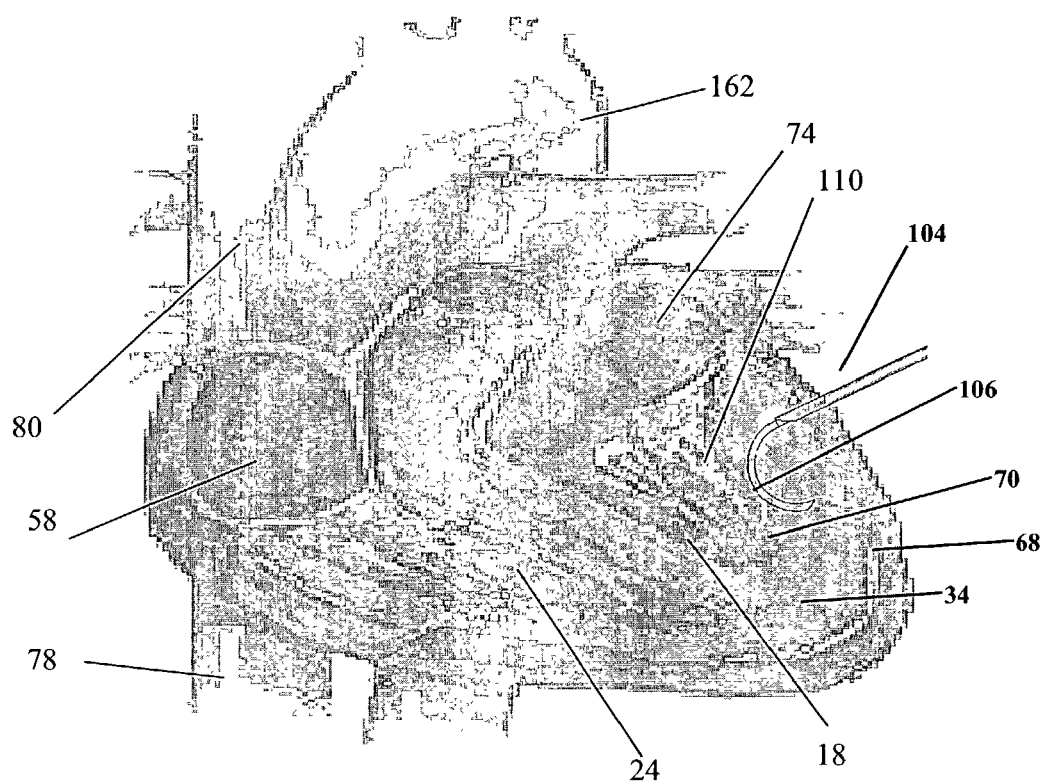
Figure 38C:
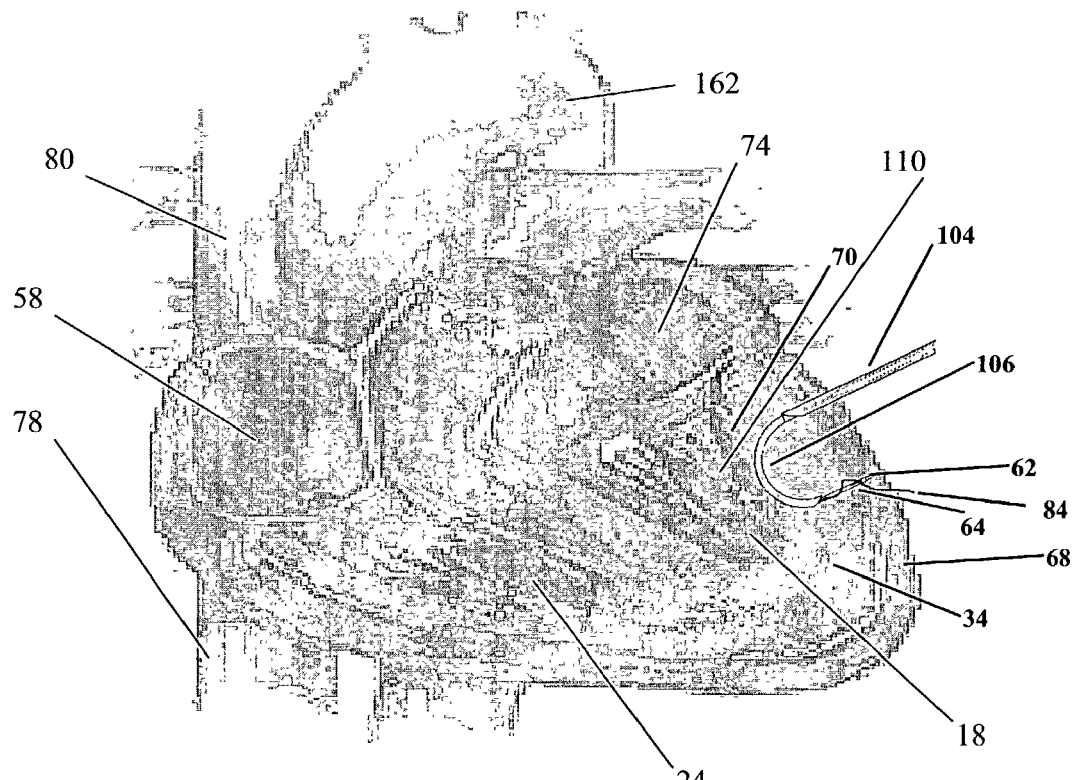

FIGS. 38A to 38C show the deployment of a tensioning structure through myocardium utilizing an alternative deployment system of the invention, which is shown in FIGS. 43A to 43D. In this embodiment, a single tensile member 84 is shown deployed through the myocardium. Afterwards, anchors can be placed over the free ends of the tensile member 84 to secure both ends of said member to the tissue surface. The opposite ends of the tensile member can then be tied producing an axially oriented tightening of the tensioning structure; or one free end of the tensile member can be subsequently inserted through myocardium at a spaced apart location to produce a three-dimensional, cinching effect; or a second tensile member can be inserted at a spaced apart location with the deployment system and the free ends of the tensile member pair can be tied together in some pattern to tighten the tensioning structure and reinforce the infarcted/ischemic zone. Again, secured 146 and movable 148 stress distributing tubes can be oriented to define the ratios of compression, regulate the amount of myocardial wall thickness reduction/compression, and distribute the stress at the insertion and exit sites of the tensile member.

Figure 43A:
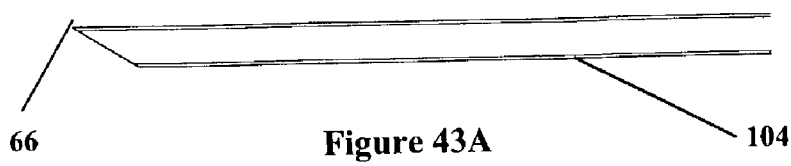
FIGS. 43A to 43D show two side-sectional views and two side views, respectively, illustrating the components of an alternative coaxially arranged delivery system used to deploy tensioning structures.
Figure 43B:
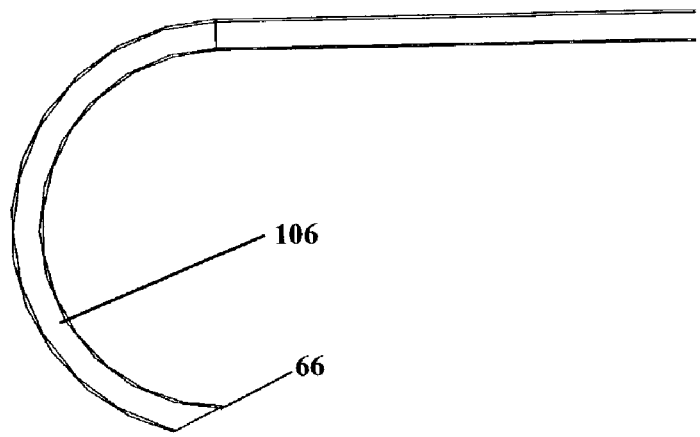
Figure 43C:
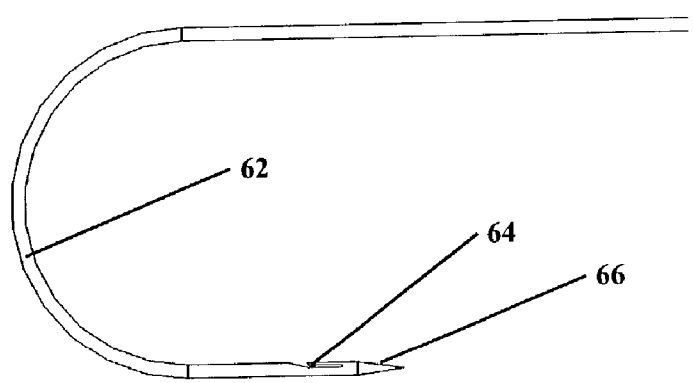
Figure 43D:
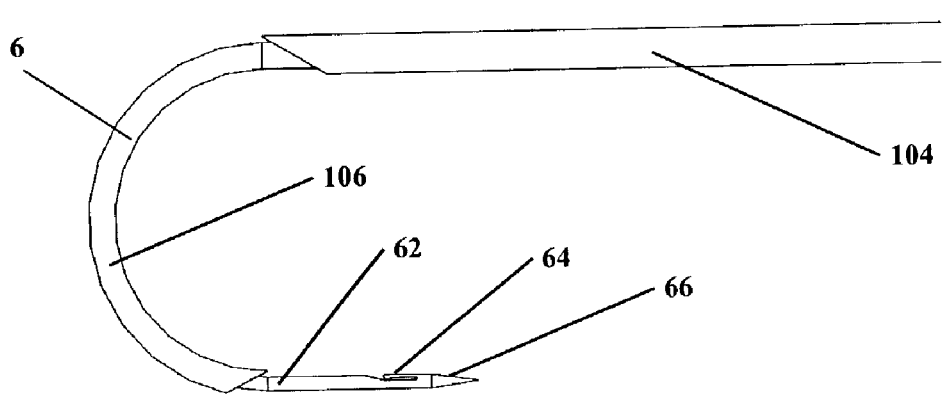

As shown in FIGS. 43A to 43D this delivery system embodiment incorporates two sheaths defining different curves and a puncturing device 62. The outer sheath 104 incorporates a beveled tip to define the initial penetration through the tissue surface. The middle sheath 106 incorporates a curved region and a beveled tip to tunnel through the myocardium (either partially or completely through the other tissue surface). The curved region of the middle sheath 106 straightens as the middle sheath is retracted into the outer sheath in a coaxial arrangement. The inner puncturing device 62 incorporates a curve to orient the distal end of the puncturing device back out of the myocardium and past the initial tissue surface at a defined distance from the initial penetration or insertion site defined by the curve of the middle sheath and the curve of the puncturing device as shown in FIG. 43D. The puncturing device 62 also incorporates a needle tip 66 (e.g., beveled tip, cutting tip, pointed tip, diamond tip, or other configuration) and a holder 64. The holder 64 in this configuration is a slotted region from one side that includes a small inward protrusion to prevent the tensile member from migrating out of the slotted region once positioned. The tensile member 84 is positioned into the holder by advancing a side of the tensile member through the slot until it is advanced past the protrusion. Removal of the tensile member can be done manually by pulling the member laterally from the slot or axially past the protrusion with forceps, needle drivers, or other surgical instrument. It should also be noted that two inner puncturing devices can alternatively be utilized with a larger middle sheath (single or dual-lumen) and a larger outer sheath to simultaneously deploy two ends of a single tensile member through tissue at spaced apart intervals or two individual tensile members through tissue at spaced apart intervals. Alternatively, three or more inner puncturing devices can be utilized with appropriately configured middle and outer sheaths to deploy more than two individual tensile members through tissue simultaneously.

Figure 42:
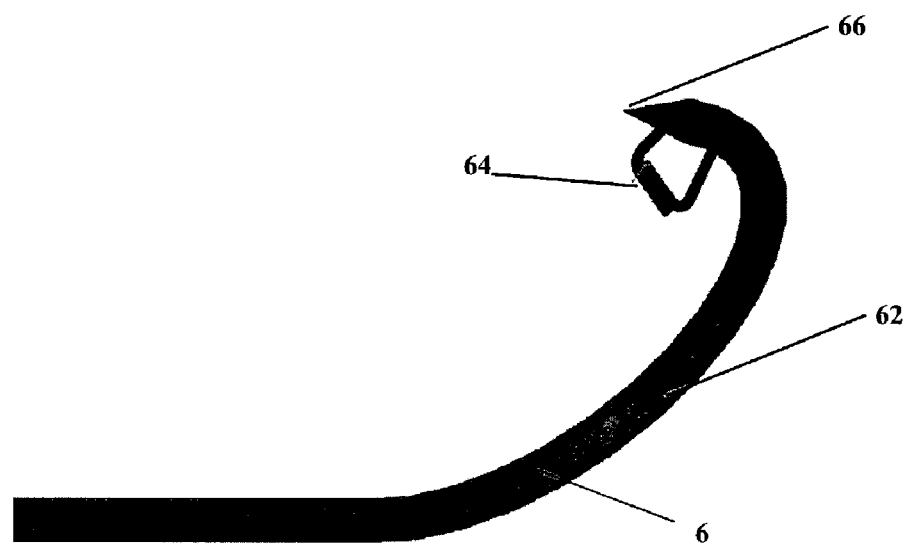
FIG. 42 shows an alternative, puncturing device used to deploy a tensioning structure.

FIG. 42 illustrates an alternative, puncturing device that incorporates the holder 64 as a separate component inserted through a hole or slot in the body of the puncturing device 62 just proximal to the needle tip 66. The holder 64 component of this embodiment consists of a wire wound into a shepherd's hook type or other similar geometry that can be fed through the hole or slot of the puncturing device such that it enables insertion or retraction of tensioning structures through tissue.

Figure 39A:
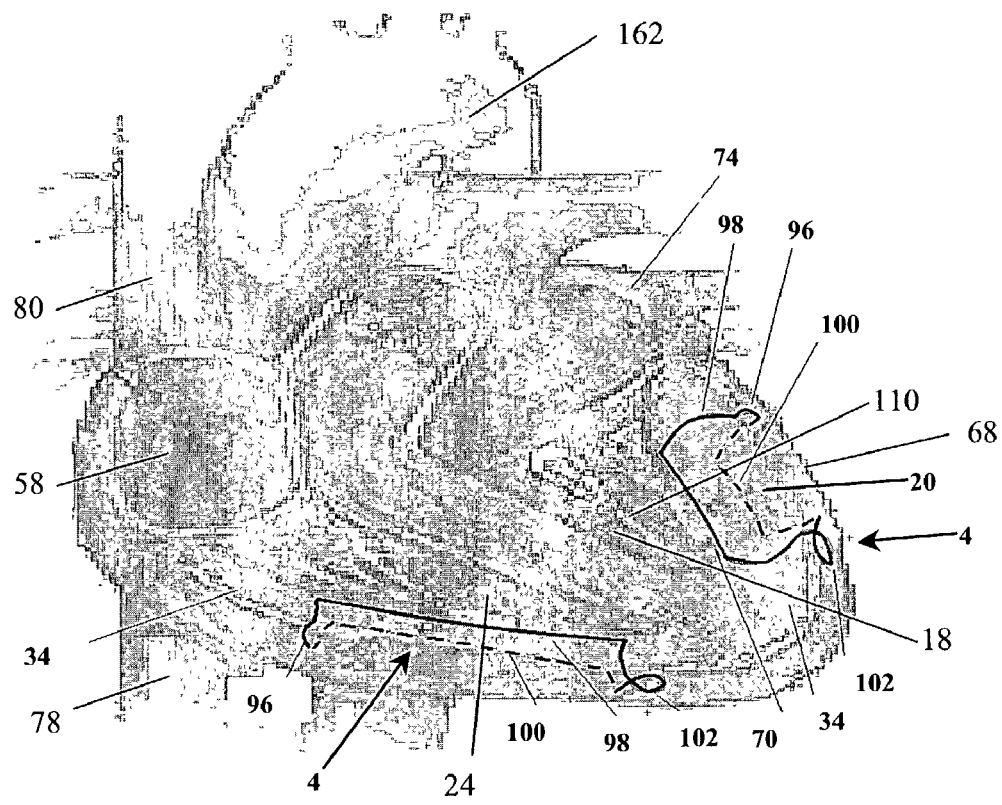
FIG. 39A shows a cross-sectional view of the heart broken in sections with the tensioning structures of FIGS. 36E to 36H deployed and secured into/through the myocardium in the right ventricle and the left ventricle.

FIG. 39A shows the placement of a three-dimensional, cinching, tensioning structure placed through myocardium of the left ventricle, extending from the epicardium, through myocardium, past the endocardium and back to the epicardium at a distance from the initial puncture site. It also depicts the placement of a three-dimensional, cinching pattern using tensioning structures through the myocardium of the right ventricle and extending along the endocardium of the right ventricle for a significant distance. The tensioning structures can be deployed with the systems described above to reinforce the left or right ventricle along an infarcted/ischemic zone or other weak or remodeling zones.

Figure 39B:
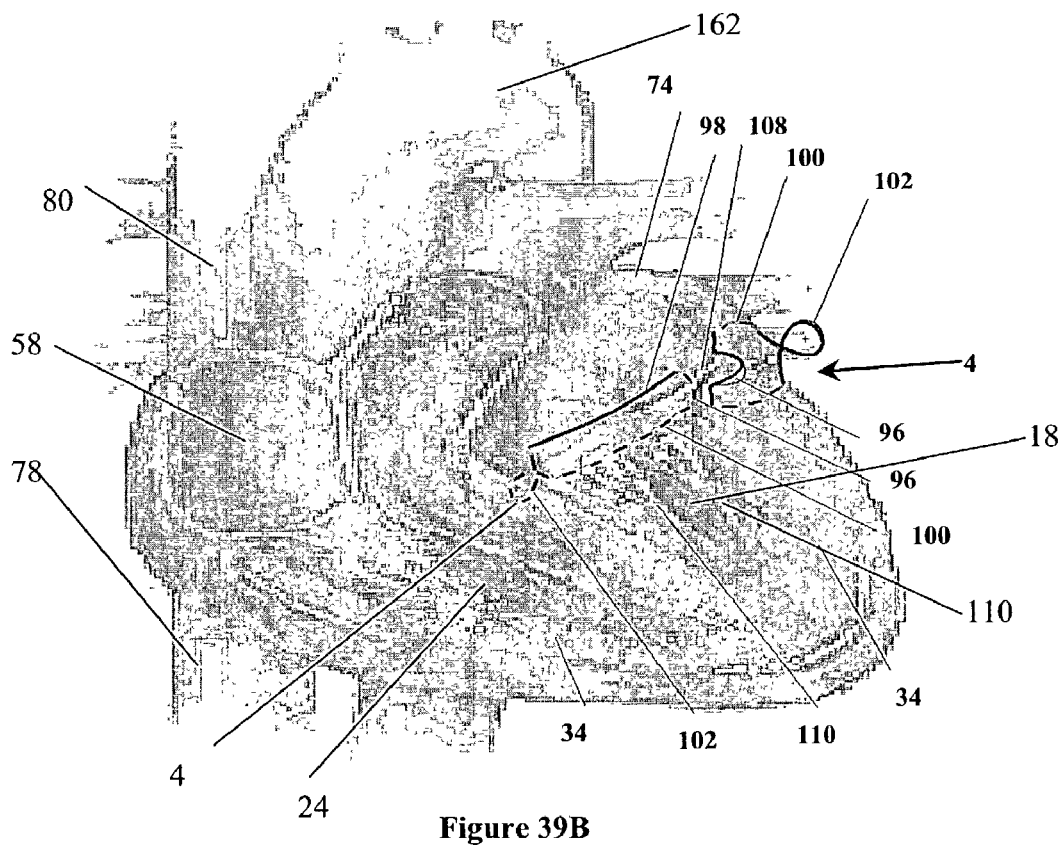
FIG. 39B shows a cross-sectional view of the heart with the tensioning structures embodiments of FIGS. 36E to 36H deployed and secured along the valve annulus.
Figure 40A:
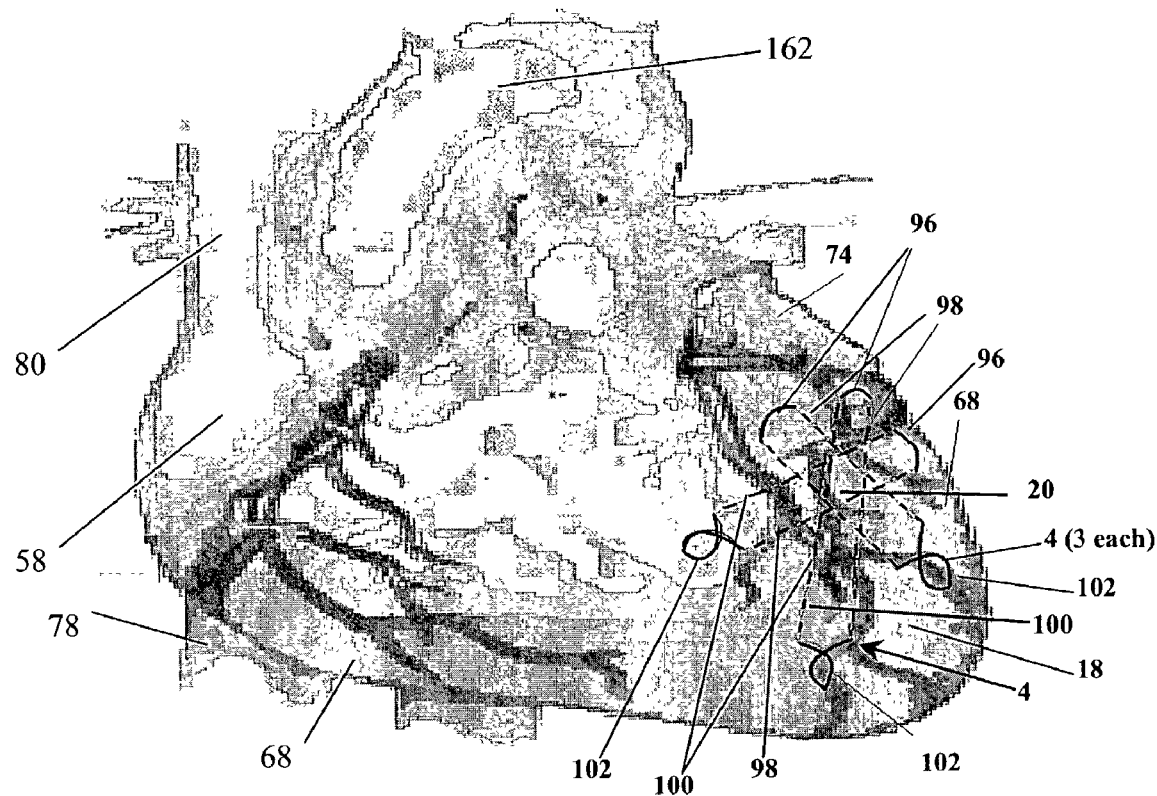
FIGS. 40A to 40F show perspective views of a heart indicating various placement configurations of the tensioning structures of FIGS. 36E to 36H.
Figure 40B:
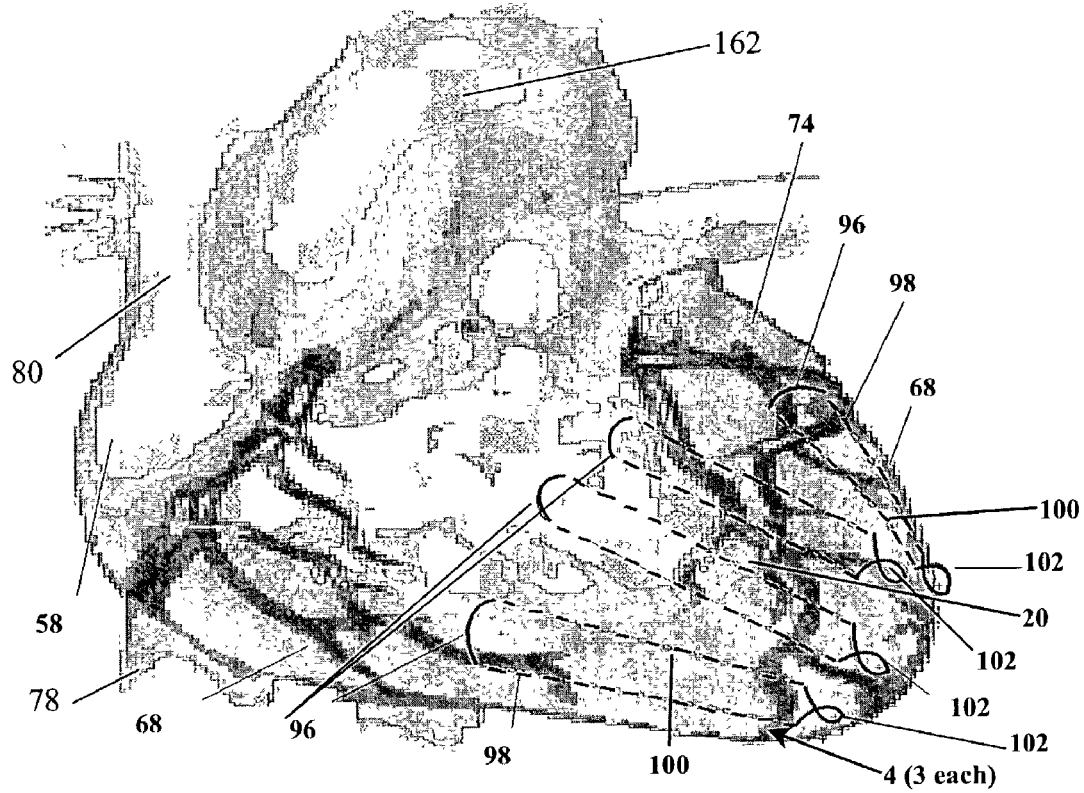
Figure 40C:
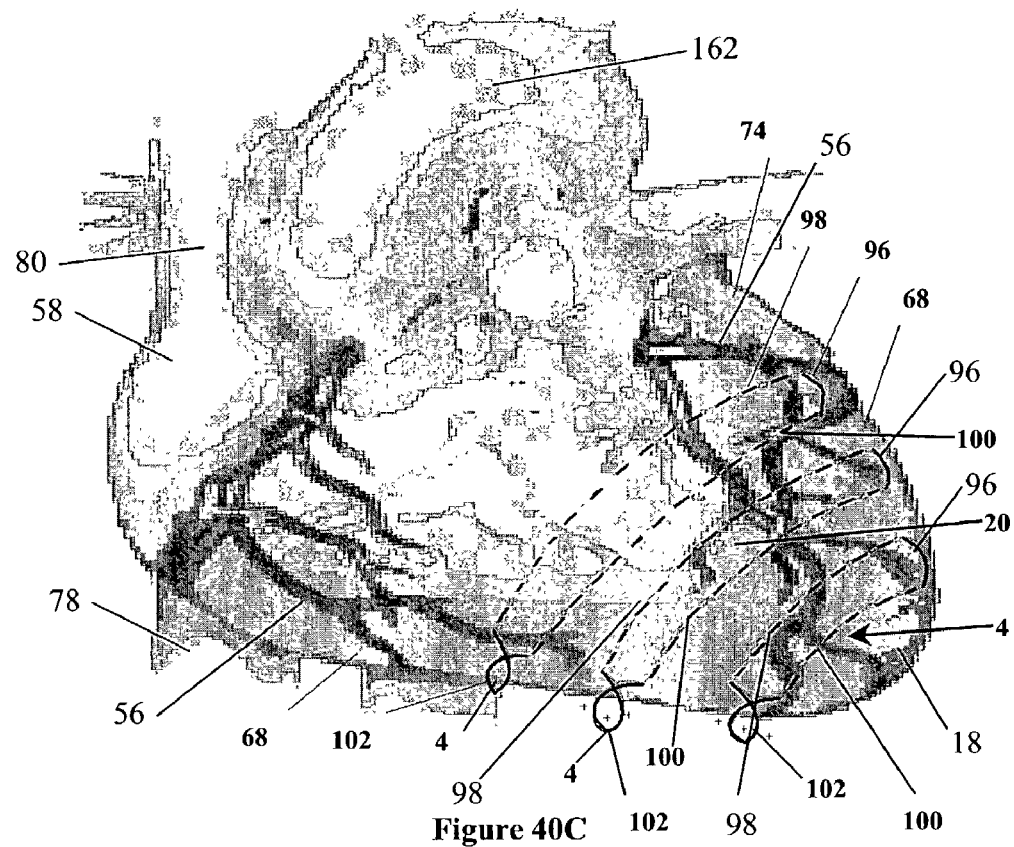
Figure 40D:
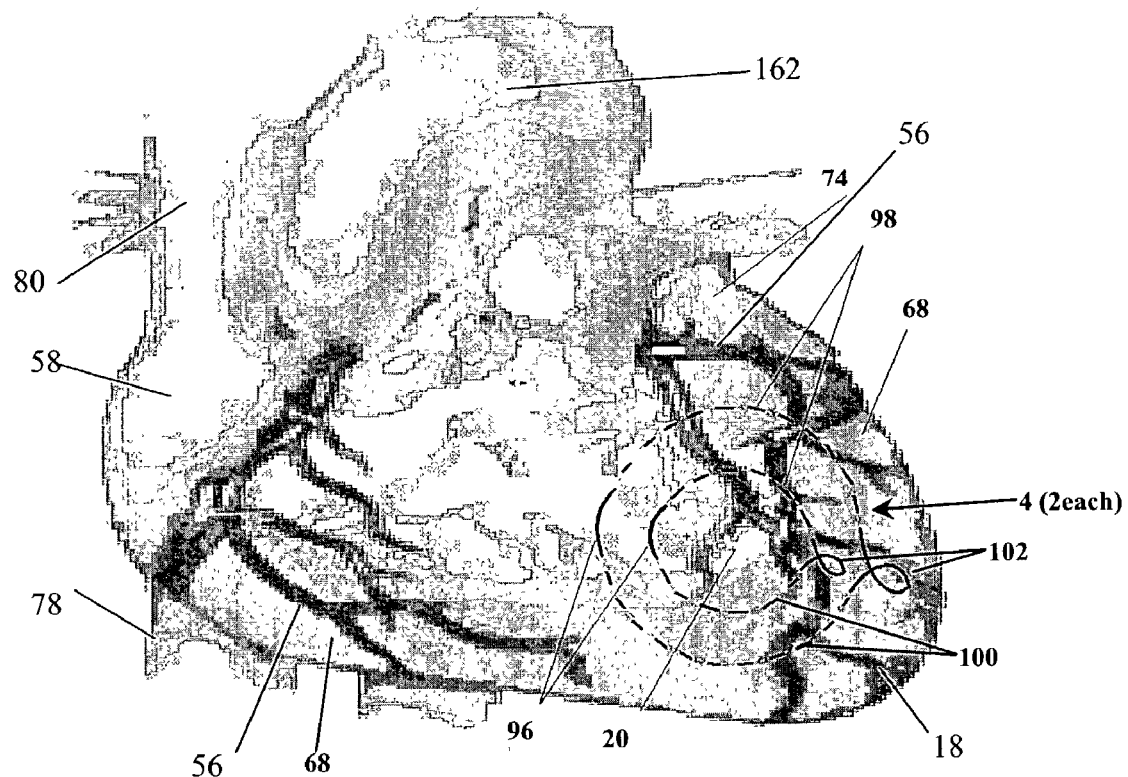
Figure 40E:
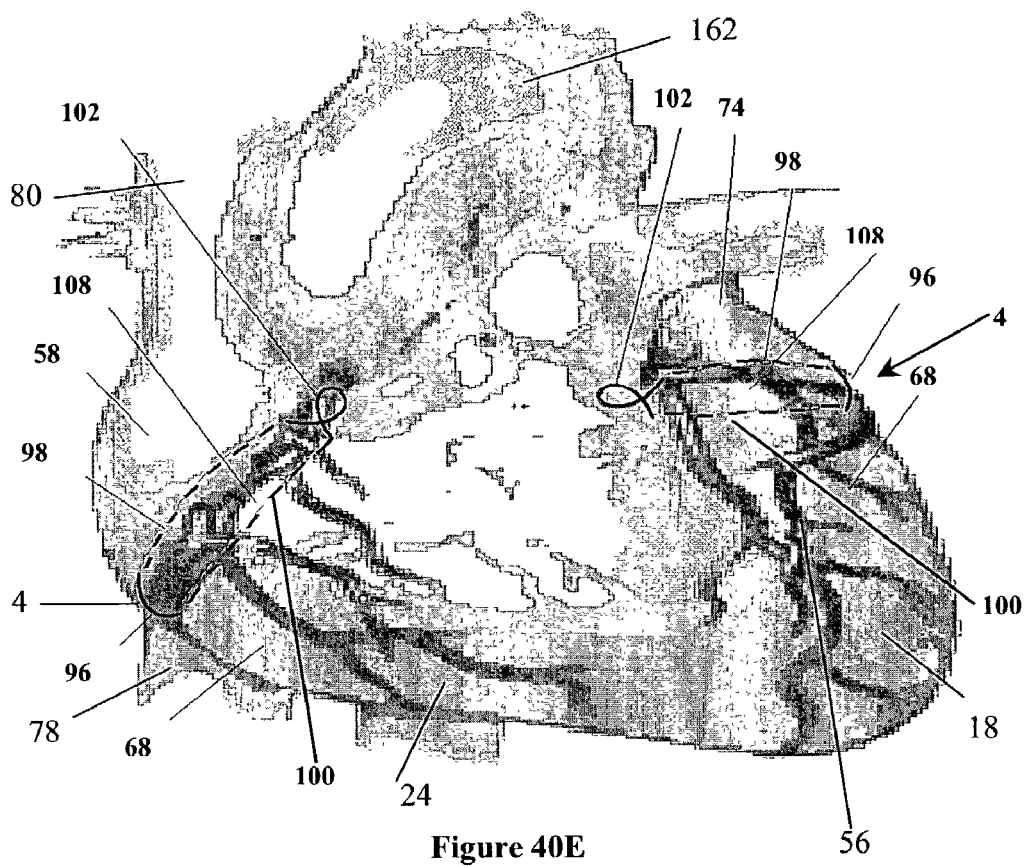

FIGS. 39B and 40E show three-dimensional cinching, tensioning structures placed along the mitral valve annulus 108 with one section of the tensile member (or one discrete tensile member as discussed above) placed on the left atrial side 74 and one section (or another discrete tensile member) placed on the left ventricular side. FIG. 40E also shows a three-dimensional, cinching, tensioning structure similarly placed along the tricuspid annulus. Once tied, the tensioning structure can cinch and tighten the mitral (or tricuspid) annulus similar to the tensioning structure embodiments discussed previously. This embodiment also enables further tightening of the tensioning structure intraoperatively, during follow-up procedures, or with mechanisms remotely actuated by directly tying the knot(s) tighter or providing a mechanism to twist, retract over a spacer, or otherwise manipulate the knot or insertion end of the tensioning structure, post procedure as desired. Alternatively, the tensioning structure can also reinforce the aortic valve by deploying one or more tensioning structures and tightening, until valve insufficiencies are resolved.

Figure 40F:
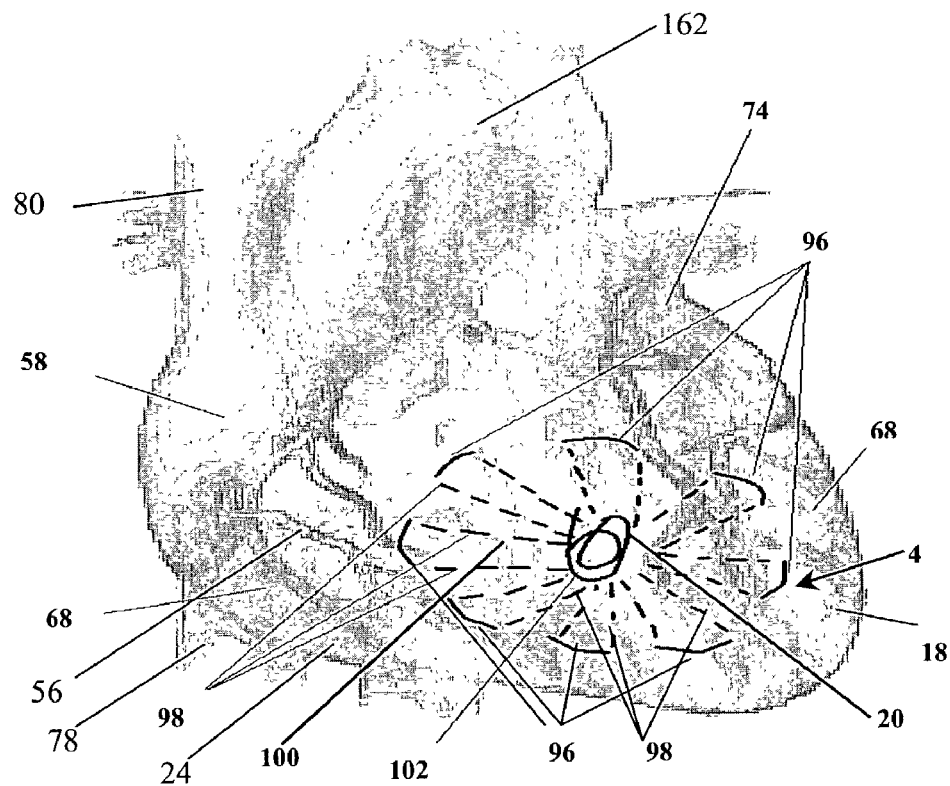

FIGS. 40A to 40D show representative three-dimensional, cinching, tensioning structure patterns capable of reinforcing infarcted and ischemic zones of the heart. Any pattern of tensioning structures can be capable of providing the desired recovery or reverse remodeling response where the tensioning structures extend between border regions of the infarcted/ischemic zones passing through the zone or extending from inside the infarcted/ischemic zone to just beyond the border regions. Also, an individual tensioning structure can pass through multiple infarcted/ischemic zones to reinforce a larger region of ventricular tissue. The flexibility of these tensioning structure and deployment system embodiments enable the physician to custom tailor the treatment options to the patient after careful analysis of the valve competency, ventricular wall motion, ejection fraction, and other diagnostic parameters. FIG. 40F shows a group of three-dimensional, cinching, tensioning structures extending around an infarcted/ischemic zone and passing from a border zone into or beyond the infarcted/ischemic zone. The free ends of this flower-shaped pattern of three-dimensional, cinching, tensioning structures can be tied together permanently or secured to a mechanism capable of twisting the knotted regions or otherwise manipulating the free ends to adjust or tighten the tensioning structures intraoperatively, during a follow-up procedure, or remotely post procedure. Again, these adjustments can facilitate chronic maintenance of positive hemodynamic conditions.

Figure 41A:
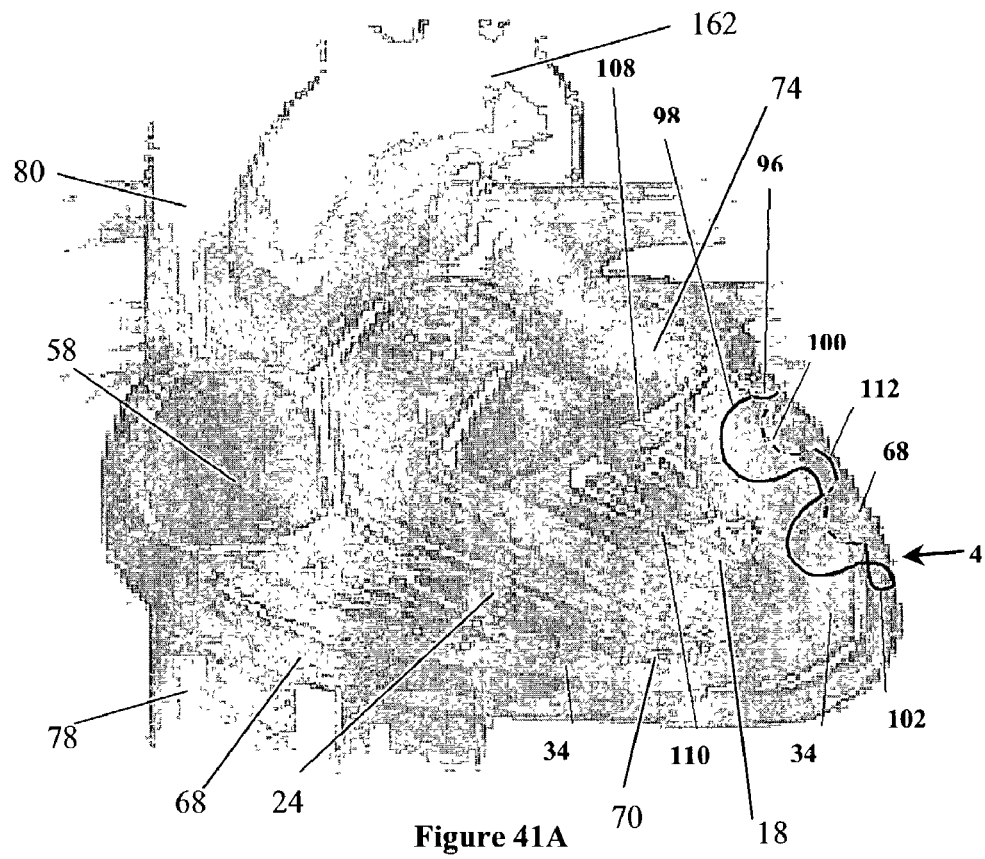

FIG. 41A shows a three-dimensional, cinching, tensioning structure incorporating two insertion and exit points along the axial plane. Again, secured 146 and movable 148 stress distributing tubes can be oriented along the tensile member, especially proximate to the various insertion and exit sites. In these tensioning structure embodiments, the tightening force is distributed at more than two locations (i.e., the insertion and knotted sites) thereby ensuring that a long, tightening structure will be capable of reinforcing tissue midway between the ends of the three-dimensional, cinching, tensioning structure. It is also noted that more than two, inline loops (as shown in FIG. 41A) can be utilized for the three-dimensional cinching tensioning structures.

Figure 41B:
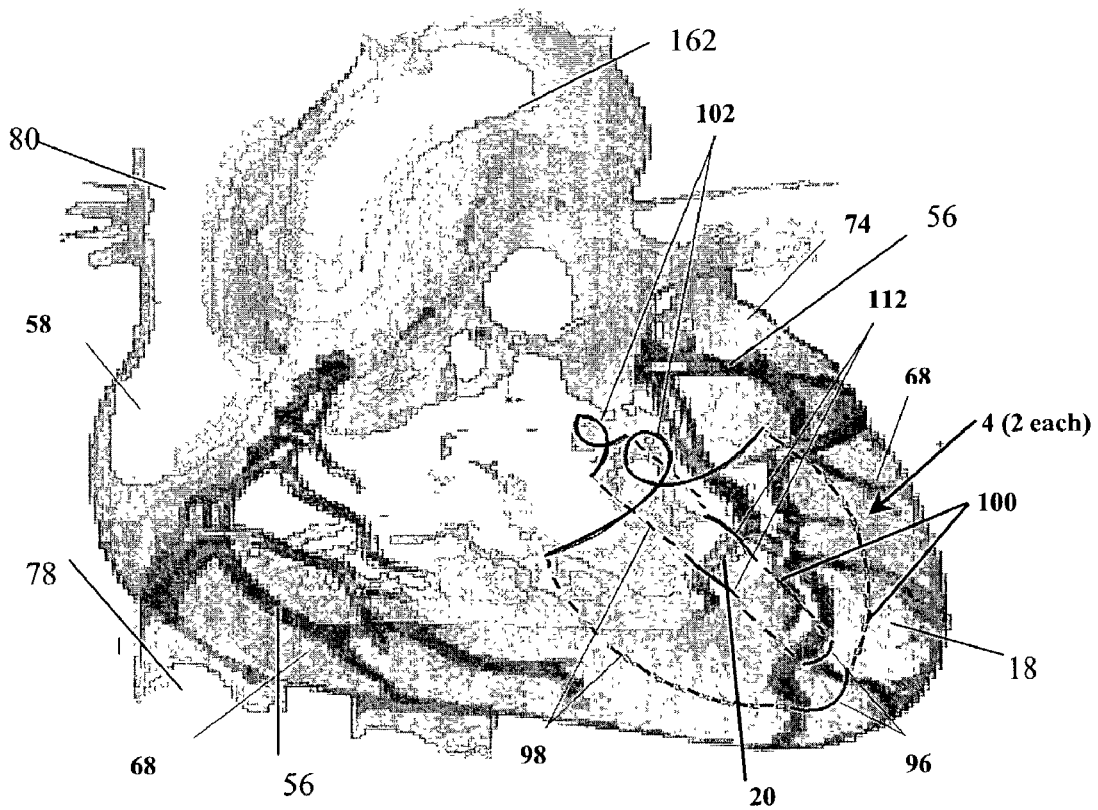

In FIG. 41B, a three-dimensional, cinching, tensioning structure oriented in a dual-loop shaped configuration surrounded by a similar tensioning structure oriented in a shield-shaped configuration. The tensile member passes through and above the tissue 112 at the center of the configuration. Together, the two patterns apply tightening forces laterally and apically to the heart to reinforce the infarcted/ischemic zone and restore a more desirable wall motion to the heart.

FIG. 41C. shows an alternative tensioning structure pattern that spirals around the infarcted/ischemic zones from the border region to the center of the zone. The free ends of this structure can be tightened to compress the zone inward towards the middle. The spiral pattern can be also be adjusted to take into account the different degrees of motion laterally versus apically by altering the length versus width ratio of the spiral pattern, the spacing between entry and exit points, and the spacing between each concentric ring of the pattern.

FIGS. 41D and 41E show a top view and a side-sectional, close-up view of another tensioning structure 4 embodiment that comprises tensile members 84 attached to radially extensible anchors 32 at each end. The tensioning structures 4 extend from within the infarct/ischemic region 20 to outside the border zone and also incorporate anchors 32 placed into or through myocardium. The proximal ends of each of the various tensile members are attached to a central hub 158 positioned on the external surface of the heart configured so that it can be tightened at or about this hub 158. The close up view of the anchor in FIG. 41E illustrates the outwardly expanded extensions placed against the endocardial (or epicardial) surface to lock the attached tensile member 84 to the heart. It is also noted that these tensioning structures can also comprise secured 146 and movable 148 stress distributing tubes as described above.

Figure 41I:
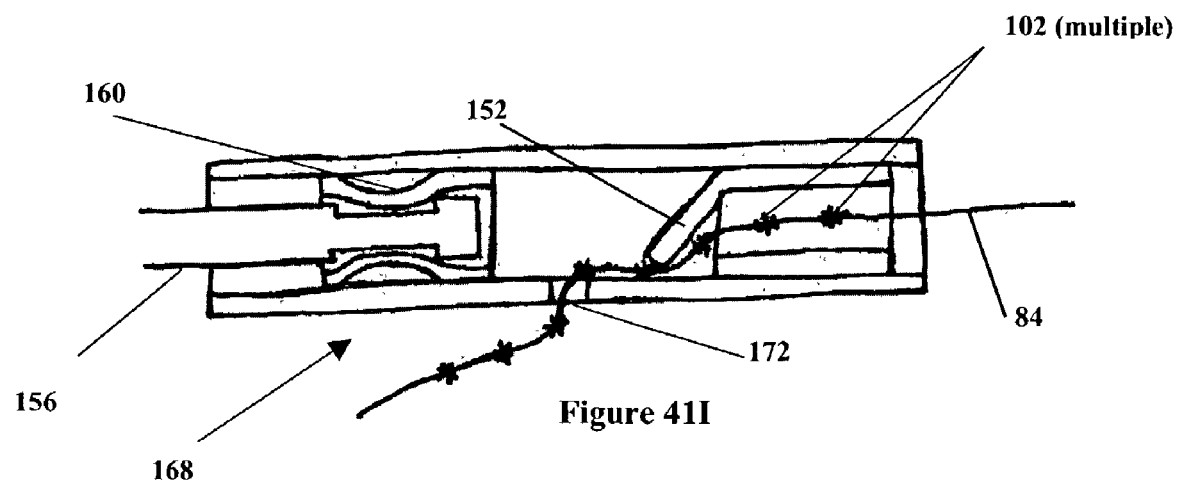
FIG. 41I shows a close-up, cross-sectional view of a proximal anchor from a cardiac valve annulus tensioning structure adapted for manual adjustment and locking of the tensile member.

FIGS. 41F and 41G show a perspective view of a heart with a three-dimensional, cinching, myocardial tensioning structure embodiment incorporating an automatic, knot-locking anchor mechanism to variably tighten the free ends of the tensile member 84. FIG. 41F shows the tensioning structure 4 with the knot anchor 150 engaging the tensile members 84, but not completely tightened. FIG. 41G shows the myocardial tensioning structure 4 with the knot anchor 150 tightened over the free ends of the tensile member 84. FIG. 41H shows a close-up, cross-sectional view of the knot anchor 150 in FIGS. 41F and 41G. A ratcheting extension or jaw 152 allows movement of the tensile member 84 in one direction, but prevents movement or migration of the tensile member in the opposite direction. FIG. 41I also depicts a close-up, cross-sectional view of an alternative, knot anchor embodiment with one end of the tensile member 84 attached and the other end movable relative to the ratcheting extension or jaw 152. In this embodiment and as with FIGS. 41F and 41G, the knot anchor also incorporates a ratchet mechanism jaw 152 that enables the tensile member 84 to pass in one direction through a sidewall exit hole 172, but prevents migration in the opposite direction allowing it to act as a locking mechanism 168. These knot anchor embodiments permit remote tightening and adjustment of the tensioning structure 4 once positioned to enable gradual tightening over a period of time to maximize and maintain the reverse remodeling effects.

Also seen in FIG. 41I is the anchoring loop 156. A formed tube 160 captures the anchoring loop 156. This tube is formed around the anchoring loop 156 such that an interference is created resulting in a mechanical joint between the components. This along with the ratcheting mechanism or jaw 152 is encapsulated by another tube to create a proximal anchor with a ratcheting capability. This embodiment is ideally suited for constriction of the valve annulus.

Figure 44A:
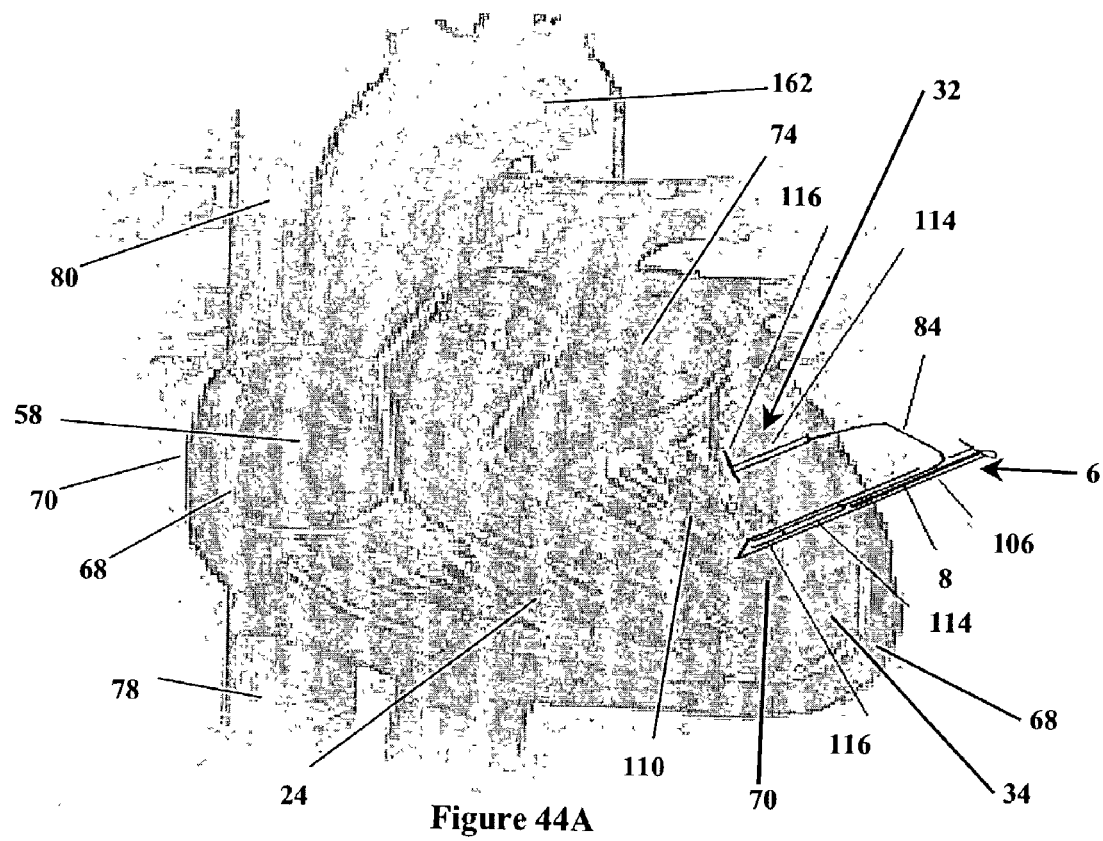
FIGS. 44A to 44C show cross-sectional views of the heart broken in sections dramatizing an extravascular deployment and securing process for a tensioning structure that incorporates anchors at each end.
Figure 44B:
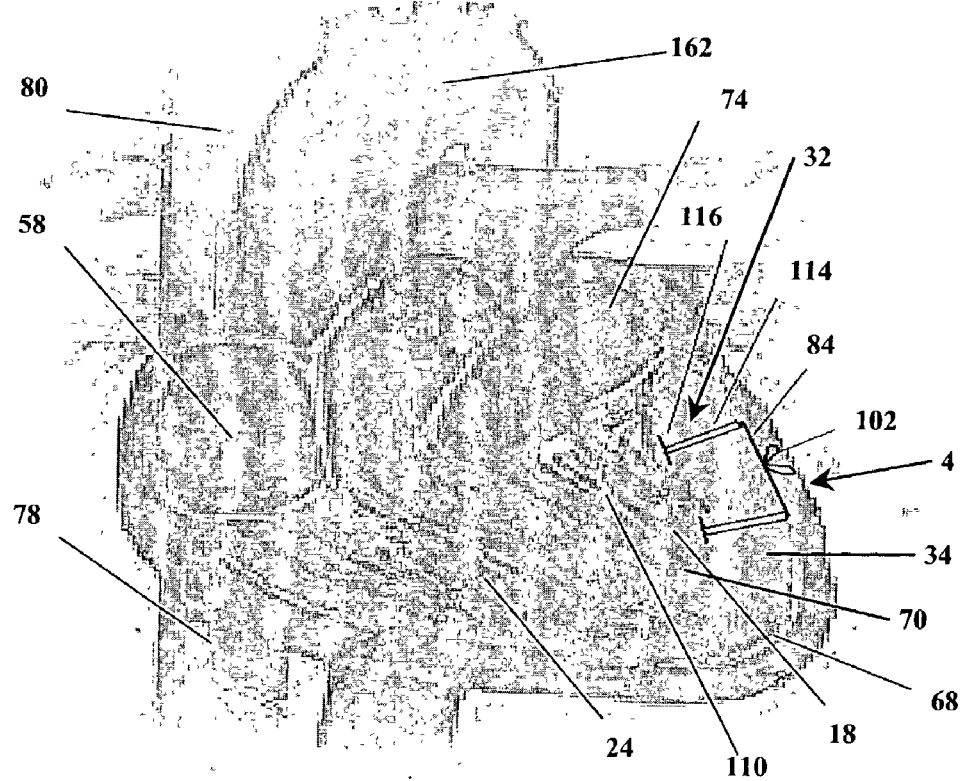

FIGS. 44A and 44B show a tensioning structure embodiment that incorporates a tensile member secured to a self-expanding (or plastically deformable) anchor as described above in the Intravascular Conduit Tensioning Structures and Cardiac Valve Annulus Tensioning Structures sections of this specification. Both anchor ends of a tensioning structure are compressed into a low profile within the lumen of a delivery sheath, similar to FIG. 43A, incorporating a beveled tip to puncture through tissue. A single sheath can be used to insert both anchors of the tensioning structure into or through myocardium, or each anchor can be compressed into individual sheaths. FIG. 44A shows a heart with sections cut away containing a deployed anchor extending through the myocardium and incorporating radial extensions engaging the endocardial surface. In this figure, a tensioning member is shown attached to the deployed anchor formation with the opposite end of the same tensioning member shown secured to an anchor compressed inside a sheath for deployment through the myocardium and into the left ventricular cavity. Once the sheath accesses the anchoring site, a stylet is used to advance the anchor beyond the confines of the constraining sheath where the anchor is allowed to expand into its preformed or radially expanded configuration. Then, the anchor can be retracted into engagement with the endocardial surface as shown in FIG. 44B with application of tension to the tensile member. At this point, the tensile member can be further tightened by creating a knot or by twisting to increase the applied force as required. It should be noted that the anchors can be placed into the myocardium such that the extensions lock to myocardial tissue without extending beyond the endocardial surface. The sheath used to deploy the anchors of the tensioning structure can incorporate a slot for the tensioning member to pass thereby preventing slack along the tensile member that is tightened by forming a knot or other tying mechanism. It is therefore noted that individual tensioning structures containing an anchor only at one end while the opposite end remains free can be deployed and secured using the deployment system previously described and the free ends can be tied together to tighten the tensioning structures to produce the desired volume reduction, reinforcement or other compressive response.

Figure 44C:
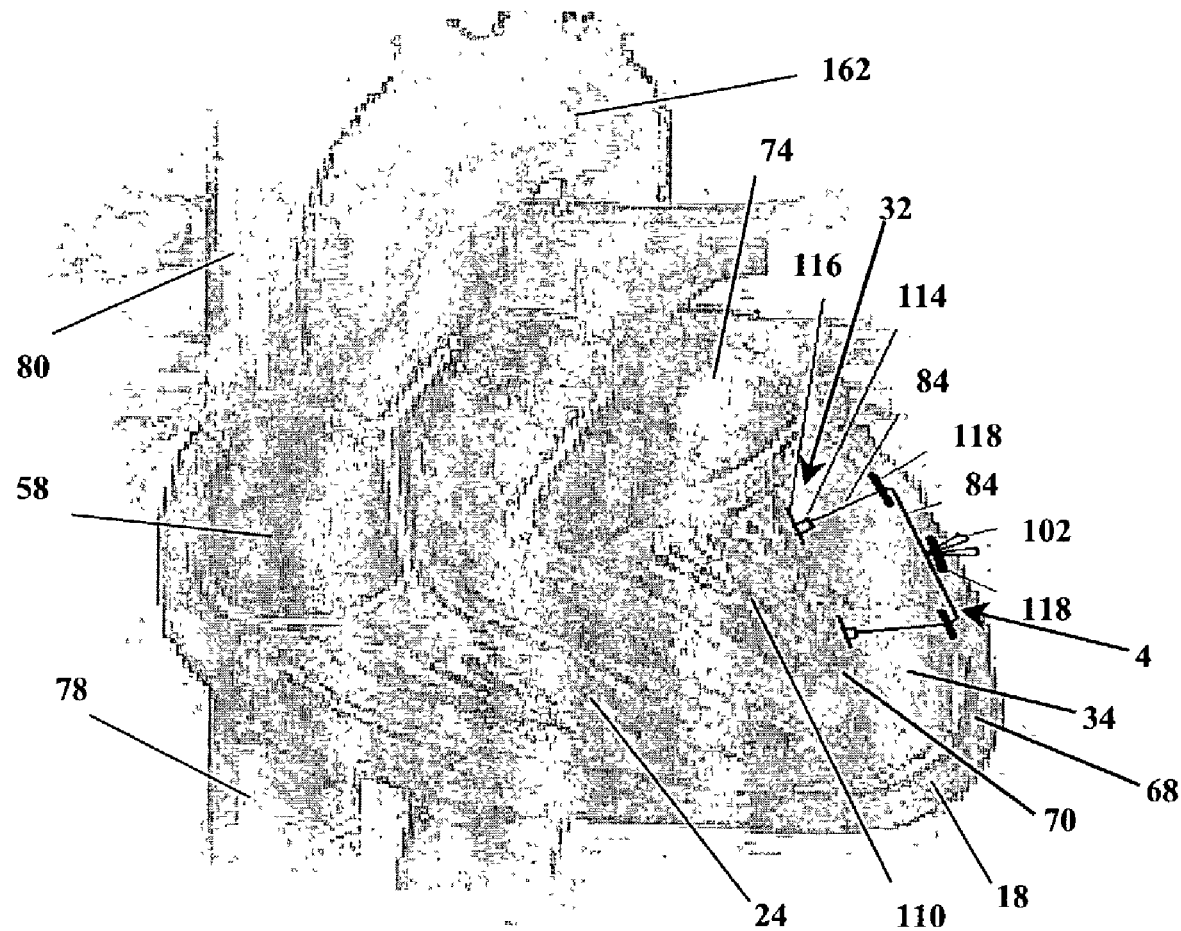

FIG. 44C shows additional features to the tensioning structure described above where pledgets 118 or other similar atraumatic interfaces mentioned elsewhere in this specification are positioned at each insertion point of the anchor through the epicardial surface to provide strain relief and to prevent abrasion or other unwanted effect of tightening of the tensile member against tissue. A pledget 118 or other atraumatic interface can also be placed under the knot used to tighten the tensioning structure. In addition, it is also noted that the tensioning structures can comprise secured 146 and movable 148 stress distributing tubes, as described above, at the insertion or exit sites, along the myocardium wall, or elsewhere along the tensile member(s).

Figure 45A:
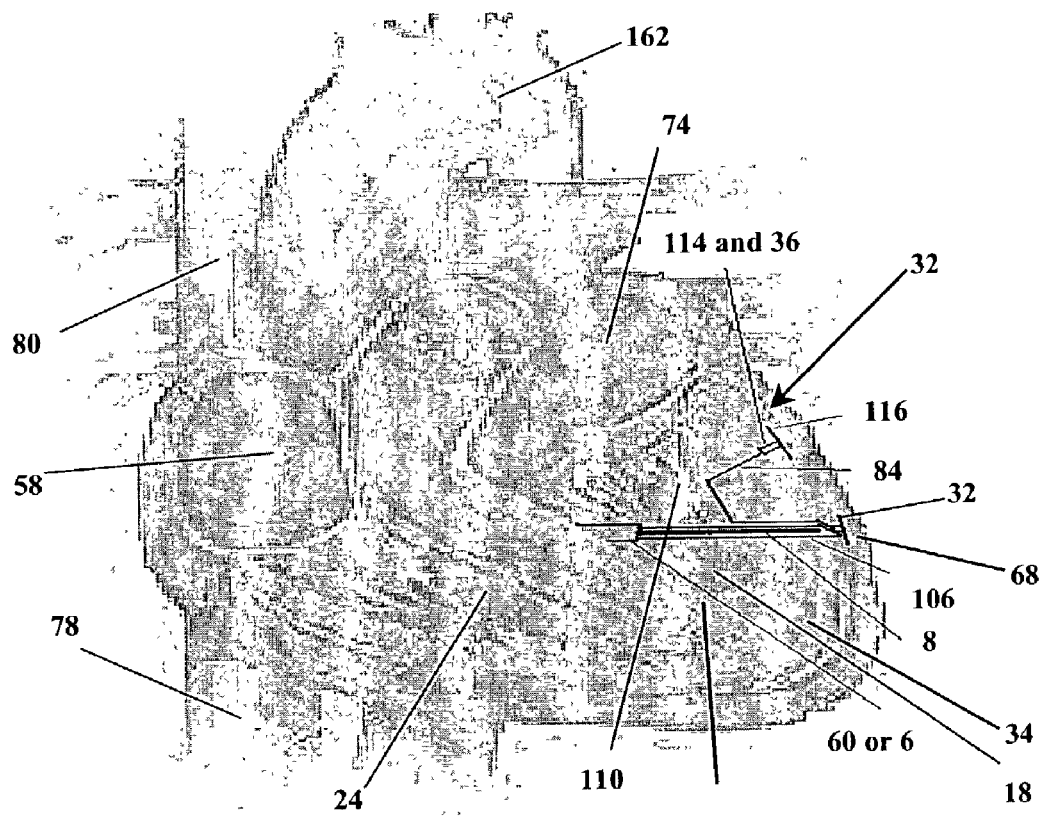
FIGS. 45A to 45B show cross-sectional views of the heart dramatizing a catheter-based delivery and securing process for a tensioning structure that incorporates anchors at each end.
Figure 45B:
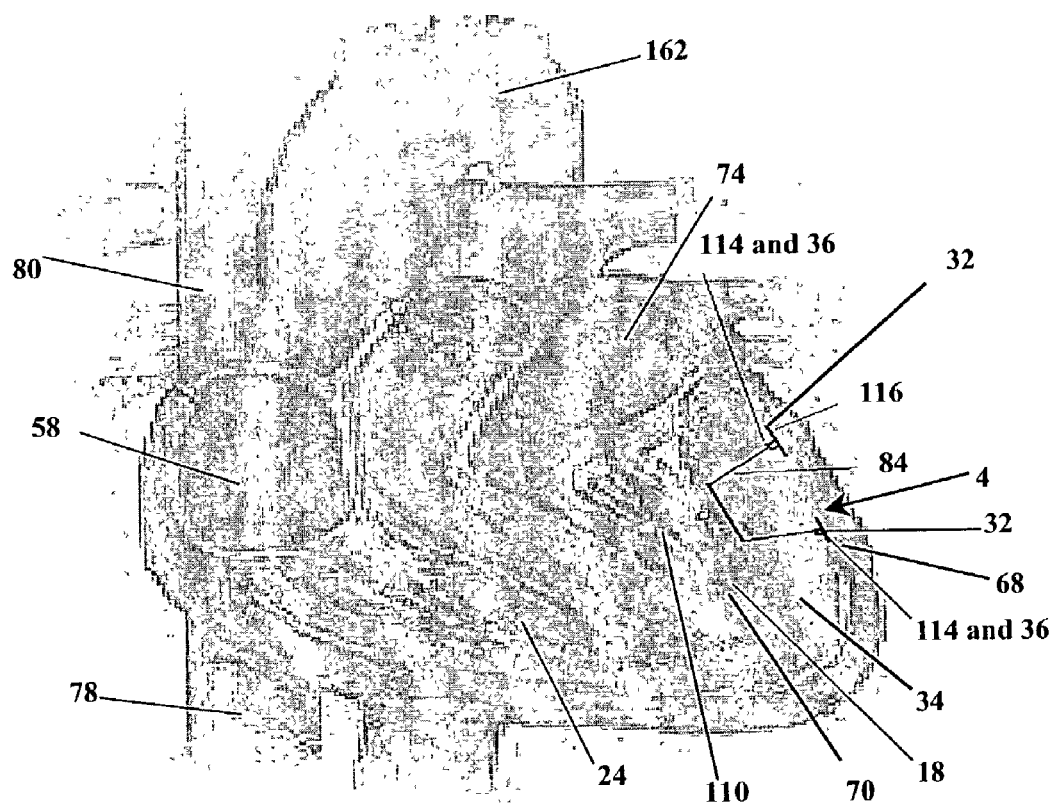

The tensioning structures and incorporated anchors can alternatively be inserted from the endocardial surface into myocardium or through myocardium such that the anchors contact the epicardial surface during surgical or catheter-based approaches, as shown in FIGS. 45A and 45B. One or more sheaths can be used to deploy the two anchors and the tensile member into the heart. The base 114 of such endocardial anchors can be configured with marker bands 36 in this approach.

Figure 45C:
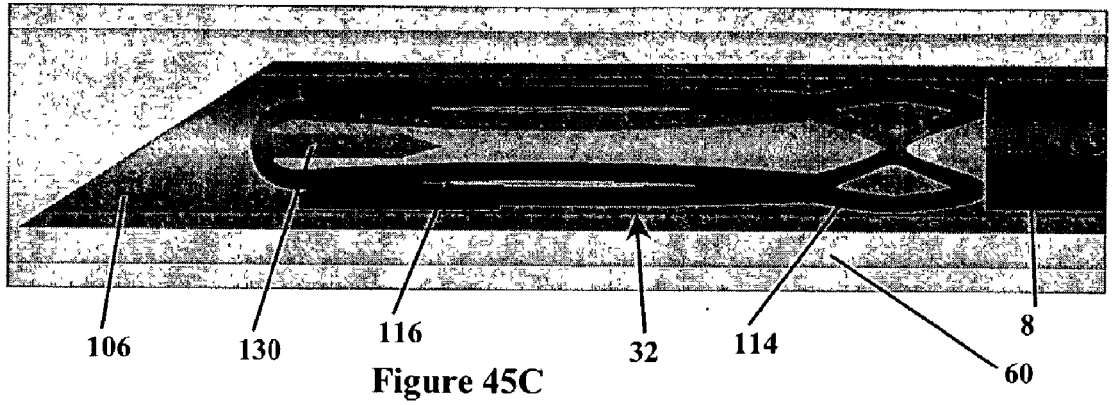
FIGS. 45C to 45E show side views with components of the delivery system and process used to deploy and secure the anchor of the tensioning structure in FIGS. 44A to 44C and 45A and 45B within the myocardium or to a tissue surface.
Figure 45D:
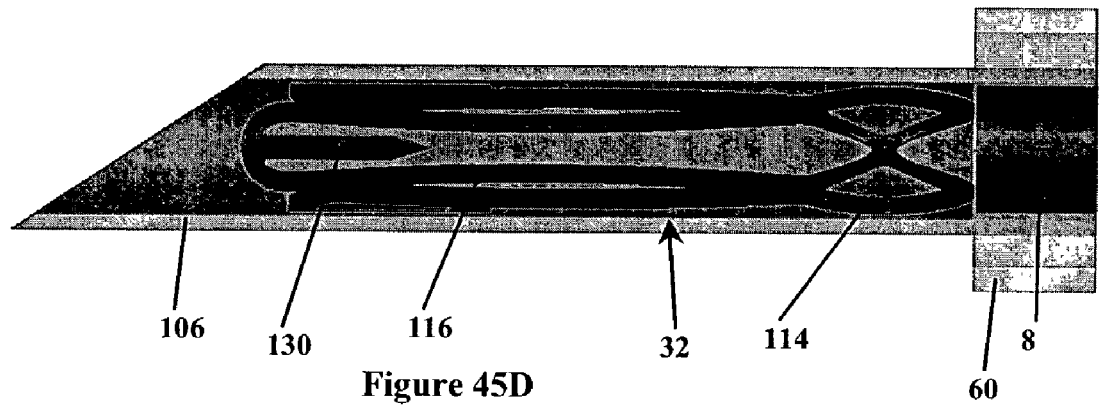
Figure 45E:
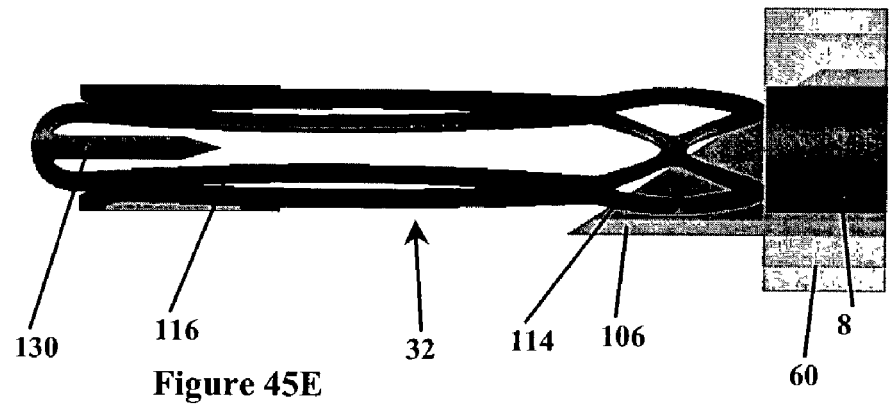

A guiding catheter, as shown in FIG. 45C, covers the beveled deployment sheath and is used to cross the aorta during a retrograde procedure, or the mitral valve during a trans-septal procedure or a surgical procedure accessing the left ventricular cavity from the left atrial appendage or atrial free wall. The deployment sheath is then advanced relative to the guiding sheath, as shown in FIG. 45D, and is used to puncture the endocardial surface to access the myocardium. The anchor can then be expelled by advancing a stylet or retracting the deployment sheath while maintaining the position of the stylet, as shown in FIG. 45E. The anchor is inserted within the myocardium or further manipulated through the myocardium, past the epicardial surface, and into the pericardial space where it expands towards its preformed configuration and is engaged against the epicardial surface, as shown in FIG. 45A.

FIGS. 45F to 45H show this anchor embodiment expanding towards its preformed enlarged, radially expanded configuration. Alternatively, a balloon or other expansion mechanism can be used to plastically deform the anchor into an enlarged orientation. The engagement pins 130 are biased outward to contact myocardium or the epicardial surface (or endocardial surface for surgical approaches described above) and prevent retraction of the anchor once positioned.

As shown in FIGS. 45F to 45H, the tensile member 84 is secured to the base 114 of the anchor preferably such that maximum outer diameter of the tensile member 84 is greater than the cross-sectional diameter of the base 114 of the anchor to ensure hemostasis through the channel created through the myocardium once the anchor is inserted and secured in place. In this embodiment, the tensile member 84 covers the entire cross-section of the base 114 of the anchor 32. Alternatively, the tensile member can be secured to one side of the base and have a diameter smaller than the outside diameter of the base 114. It should be noted that the deployment system and anchor embodiments shown in FIGS. 45C to 45H are directly applicable to the surgical process described for FIGS. 44A to 44C above.

Figure 45I:
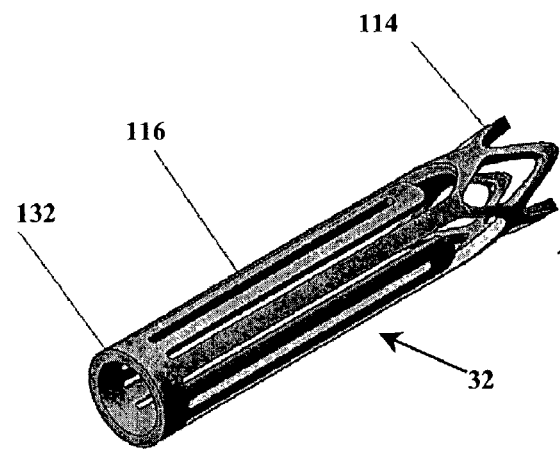
FIGS. 45I to 45L show three perspective views and one side view, respectively, of an alternative anchor member indicating the fabrication process for a tensioning structure.
Figure 45J:
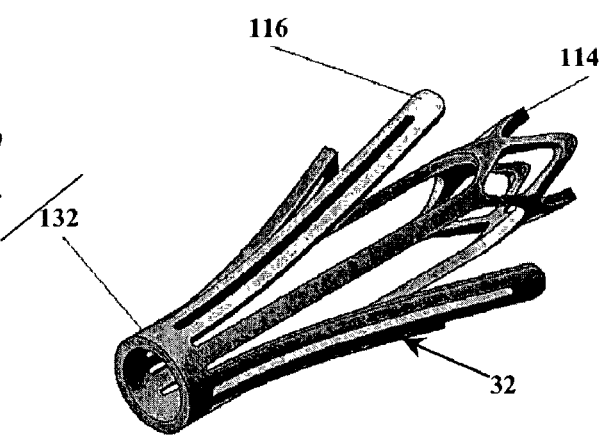
Figure 45K:
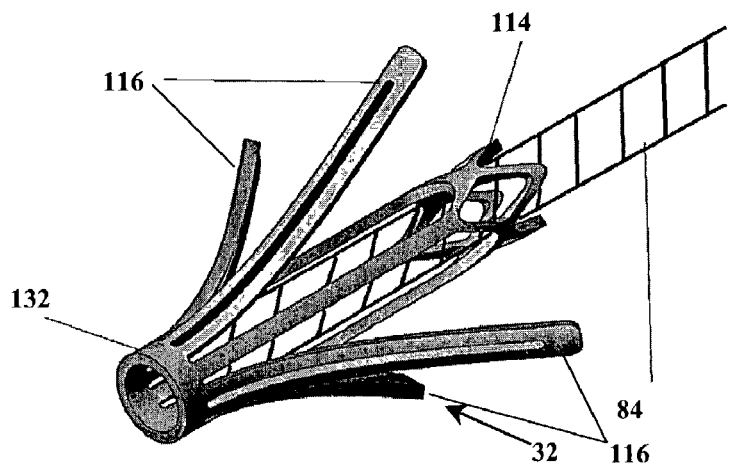
Figure 45L:
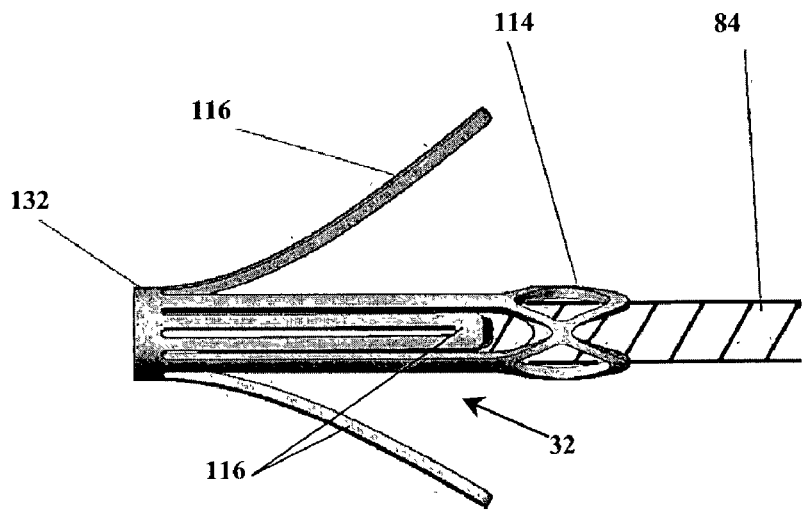

FIGS. 45I to 45L show an alternative anchor member 32 well suited for use as a myocardial tensioning structure embodiment. FIG. 45I shows a tube of anchor material (e.g., nickel titanium, titanium, stainless steel, superelastic polymer, or other such anchor material previously described) cut into a pattern of extensions 132 emanating from the distal end 132 of the anchor, and a base 114 to which the tensile member 84 is attached. The base 114 (and distal end 132) can be fabricated as expandable/compressible to enable expansion or compressing the anchor during or after deployment. FIG. 45J shows the process of thermal forming the anchor extensions 116 into a radially expanded orientation. FIGS. 45K and 45L show a perspective view and a side view of the anchor 32 with a tensile member 84 attached to the interior surface of the anchor from the distal end 132 to the base 114. As described in FIGS. 45F to 45H above, the tensile member 84 can alternatively be attached beyond the exterior surface of the base 114.

In addition, the anchor embodiments shown in FIGS. 45F to 45L can be utilized as an anchor that engages the coronary sinus orifice when inserting the tensioning structure intravascularly within the coronary sinus for tightening and reinforcing the valve annulus as described in the Cardiac Valve Annulus Tensioning Structures section above. These anchor embodiments can also be inserted through valve leaflets to reposition the valves upon applying tension via the tensioning structure, as described in the Chordae Tendineae and Valve Leaflet Tensioning Structures section below.

A single sheath incorporating two stylets having different profiles to accommodate different diameter anchors or anchors incorporating features enabling sequential deployment of the first anchor prior to actuation of the second anchor can be used to deploy the tensioning structure during catheter-based procedures. Once the first anchor is positioned and engaged into tissue, the second can be positioned and deployed. The final result of such an approach is illustrated in FIG. 45B.

Figure 46H:
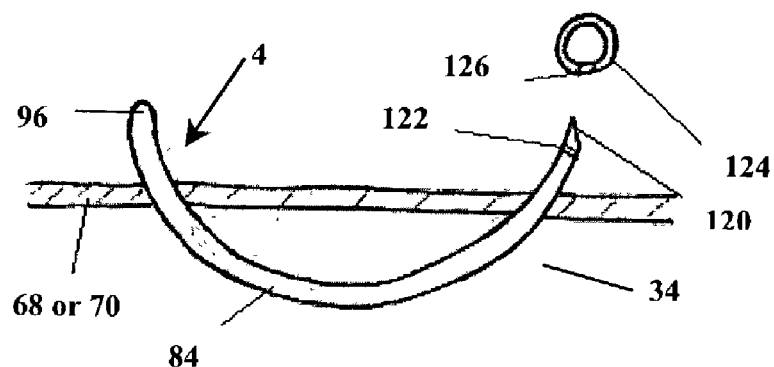
Figure 46I:
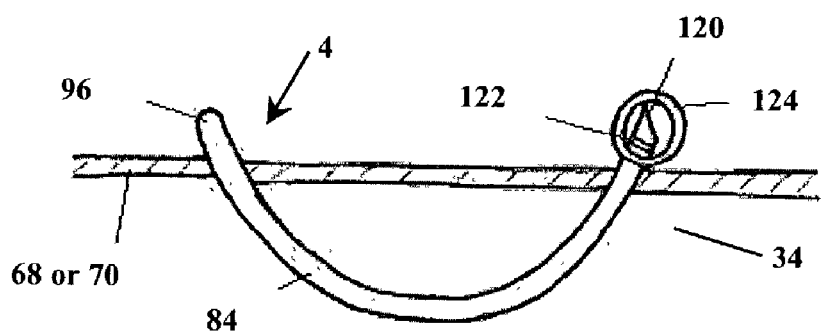
Figure 46J:
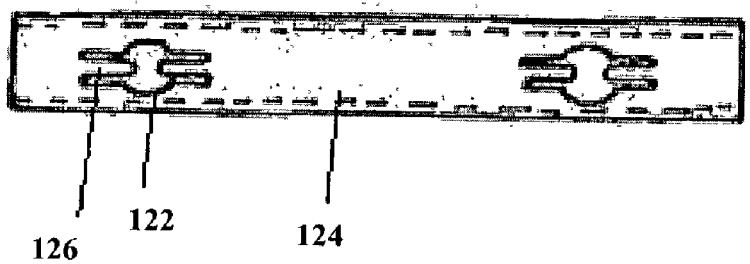
Figure 46K:
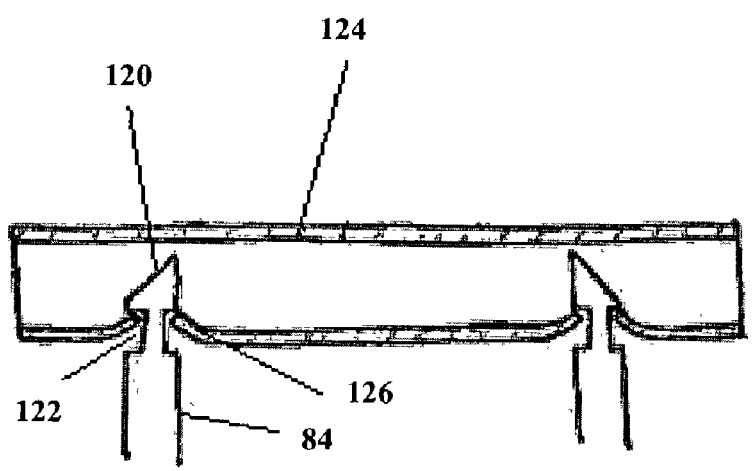
Figure 46Q:
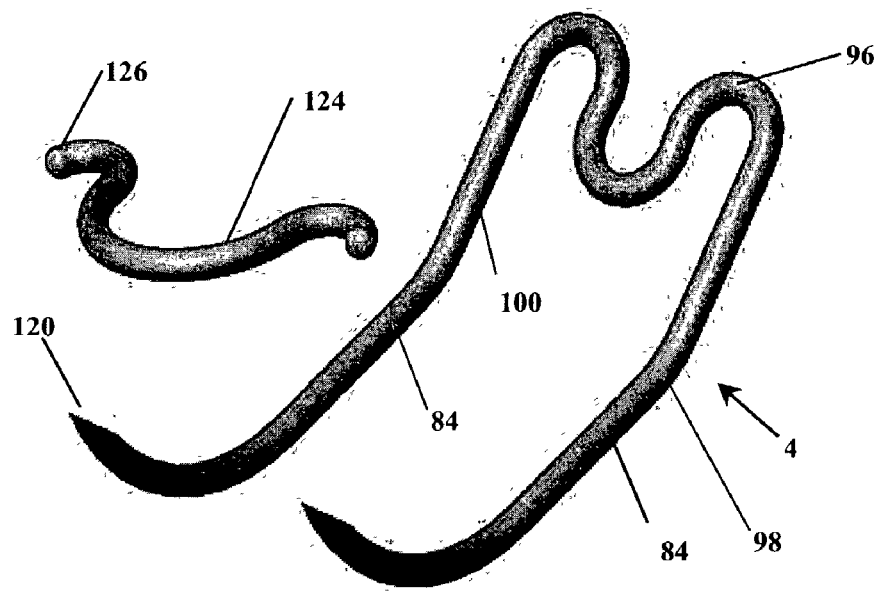
FIGS. 46Q and 46R show perspective views of additional integrated tensioning structures according to the present invention.
Figure 46R:
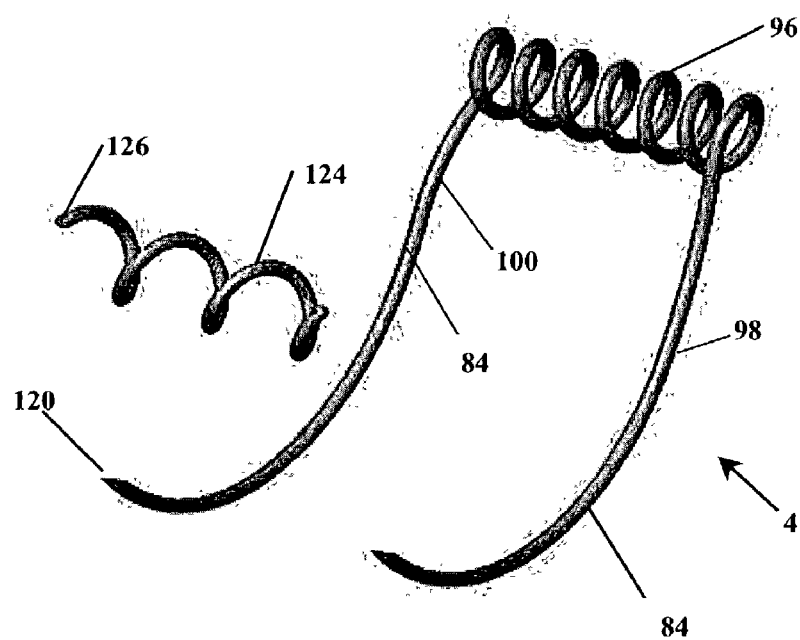
Figure 46S:
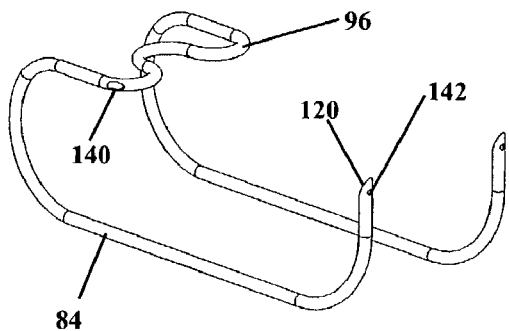
FIGS. 46S to 46T show a perspective view and a side view, respectively, of another integrated tensioning structure.
Figure 46T:
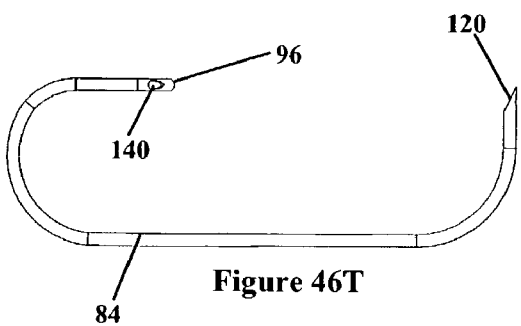
Figure 46U:
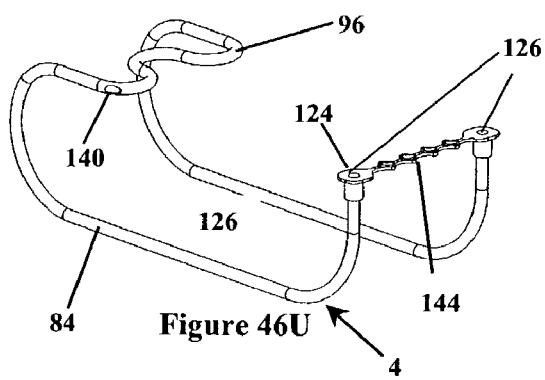
FIGS. 46U to 46Y show a perspective view, a side view, and side and top close-up views, respectively, of the integrated tensioning structure of FIGS. 46N to 46O with a separate anchor attached.
Figure 46V:
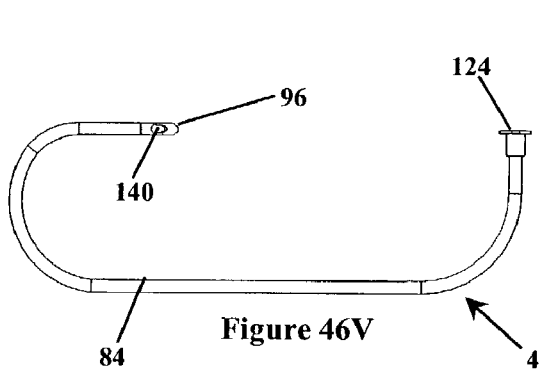
Figure 46W:
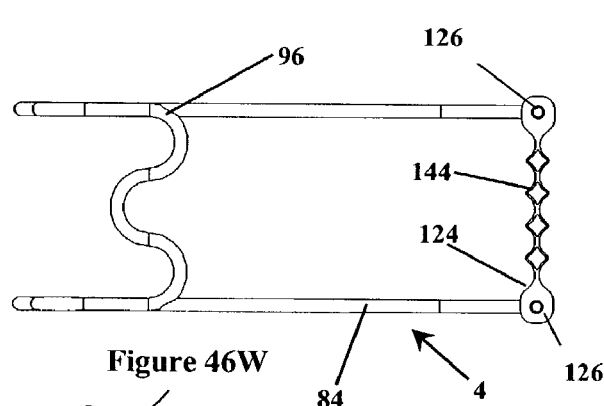

FIGS. 46A to 46M show an alternative, integrated tensioning structure embodiment where the tensile member 84 incorporates features to enable anchoring and a preformed geometry having sufficient column strength to be directed through myocardium without the need for the deployment sheath to puncture tissue to insert the tensile member and/or anchor. As shown in FIGS. 46A and 46B, the tensioning structure is constrained into a low profile inside a blunt tip deployment sheath. This tensioning structure embodiment is preferably fabricated from a superelastic alloy (e.g., nickel titanium), other alloy (e.g., stainless steel), or metal (e.g., titanium) incorporating an elastic component and a preformed geometry. As shown in FIGS. 46E through 46F, the tensioning structure itself is used to puncture the epicardial surface (or endocardial surface for catheter-based approaches) and channel through the myocardium. As the tensioning structure is further advanced beyond the confines of the blunt deployment sheath, as shown in FIG. 46G, the tensioning structure returns towards it preformed or expanded shape directing the free end of the tensioning structure back up towards and past the epicardial (or endocardial) surface. This tensioning structure embodiment consists of a stiff tensile member formed into a "U" shape with sharp free ends 120 to penetrate tissue. Each of the free ends 120 is inserted through the tissue surface at spaced apart intervals such that once positioned the looped or flat end of the "U" shape can be used to anchor the tensioning structure at one end. As described previously, secured 146 or movable 148 stress distributing tubes can be used as required at this end to dampen the trauma and regulate application of the compressive forces by the tensioning structure against the tissue surface. As shown in FIGS. 46H through 46K, a separate locking anchor 124 can be secured to the free ends of the tensioning structure into notches 122 or other mating features in the tensioning structure 4 to define and maintain the applied tension and to prevent migration. The anchor can consist of a tube, bar, or sheet containing openings and a ratchet mechanism that allows the sharp ends of the tensioning structure to enter while preventing separation once placed, as shown in FIG. 46K. FIGS. 46L and 46M show an illustrated placement of this tensioning structure embodiment after deployment and after locking with the anchor component, respectively. As with all of the 3-dimensional, cinching, tensioning structures described previously, this clip-like tensioning structure embodiment can traverse in any direction around the infarcted/ischemic zone and multiple clip-like tensioning structures can be inserted and secured throughout the infarcted/ischemic zones to custom tailor the reinforcement profile to the patients needs.

FIGS. 46N to 46P show additional delivery system features for deploying these integrated 3-dimensional, cinching, tensioning structures. FIG. 46N shows the deployment sheath with a flared, distal end 134 to provide strain relief during puncture, and FIGS. 46O and 46P show expandable/compressible extensions associated with the deployment sheath to enable low profile entry into the body, to stabilize and provide a surface to leverage the deployment sheath during puncture preventing inadvertent insertion of the sheath through the heart's surface. An outer constraining tube 138 is used to compress the extensions 136 during deployment through ports into the chest cavity or other less invasive access. Alternatively, the extensions can be fabricated rigid, especially for invasive surgical approaches such as a median sternotomy.

Figure 46X:
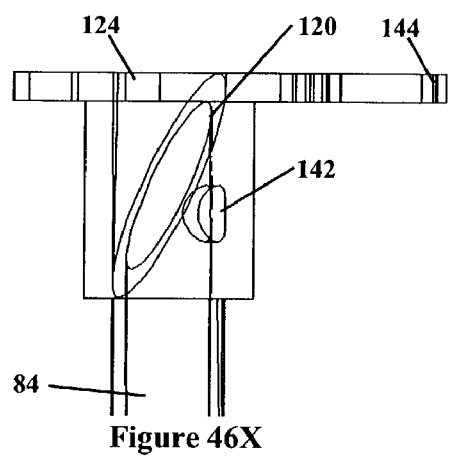
Figure 46Y:
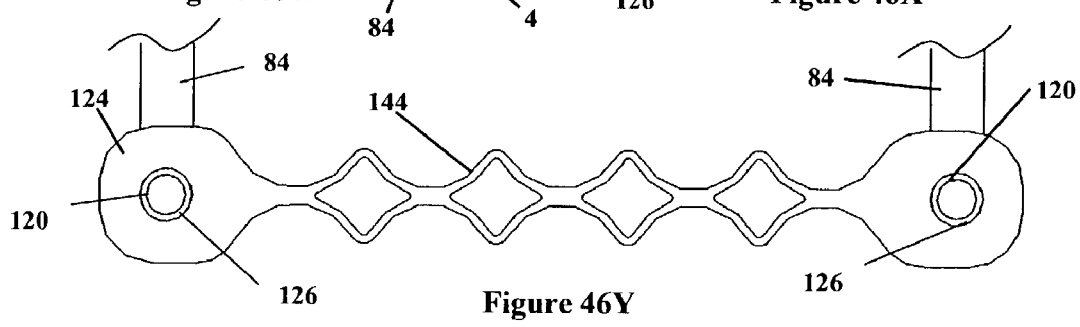

FIGS. 46Q to 46Y show alternative integrated, 3-dimensional, cinching, tensioning structures 4 of the invention. These tensioning structures 4 incorporate spring mechanisms at the loop anchors 96 and anchor lock springs 144 to further custom tailor the cinching forces applied by the tensioning structure to the heart tissue. These spring mechanisms can comprise a helix, a sinusoid, open cells, or other expandable and compressible mechanisms. As shown in FIG. 46X, anchor lock holes 142 can be incorporated in the distal end of the tensile member 84 to enable locking the anchor lock springs 144 to the tensile member 84 to define the attached tensioning structure 4.

The three-dimensional, cinching, tensioning structure in FIGS. 46S to 46Y further incorporates a straightening lumen 140 through which a stylet can be inserted to orient the tensile member 84 for deployment into or through myocardium. As the stylet (not shown) is advanced through the straightening lumen 140, the tensile member straightens for insertion into or through myocardium. As the stylet is retracted or the tensile member is advanced beyond the end of the stylet, the tensile member reverts back towards its preformed, curved shape channeling through tissue and defining the deployed configuration. Once deployed, the stylet is removed leaving the tensile member to be locked with the anchor spring 144.

Chordae Tendineae & Valve Leaflet Tensioning Structures

Figure 47A:
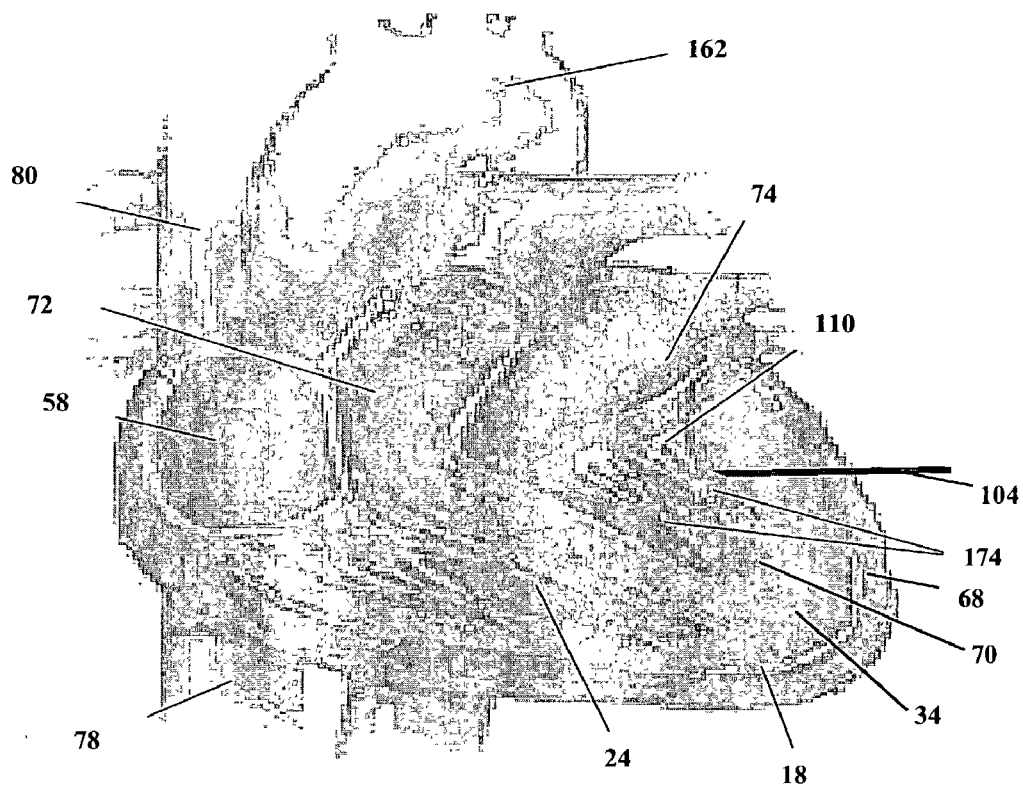
FIGS. 47A to 47D show a cross-sectional view of the heart dramatizing the process of deploying and securing a tensioning structure around and/or to a chordae tendineae or papillary muscle.
Figure 47B:
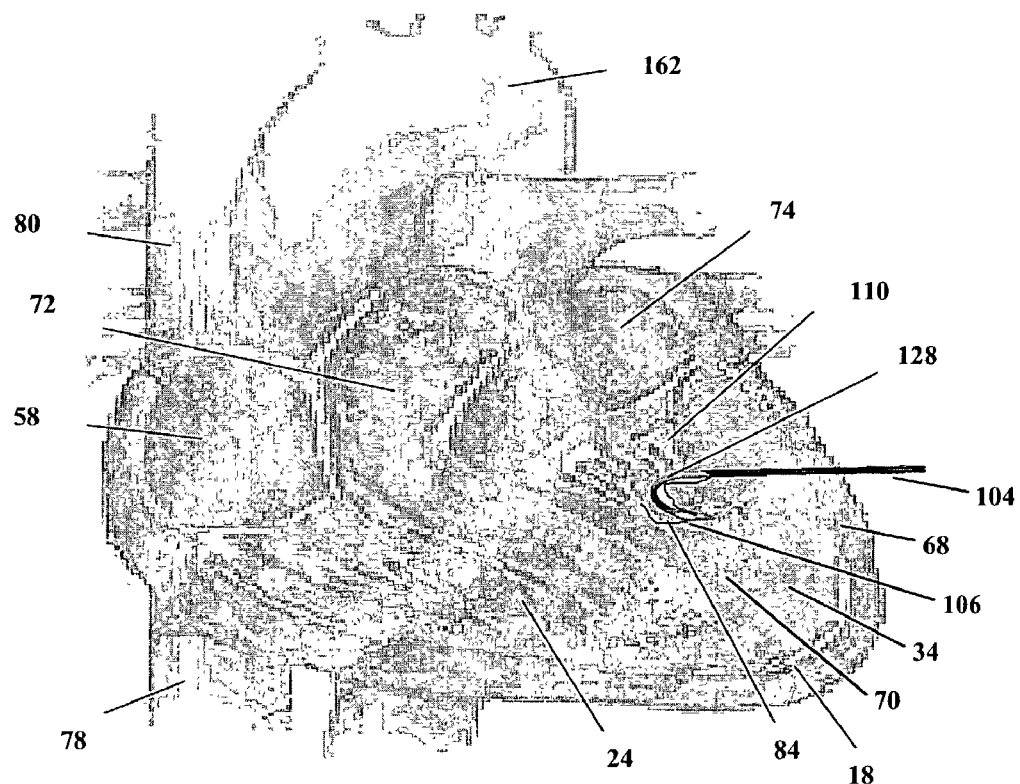
Figure 47C:
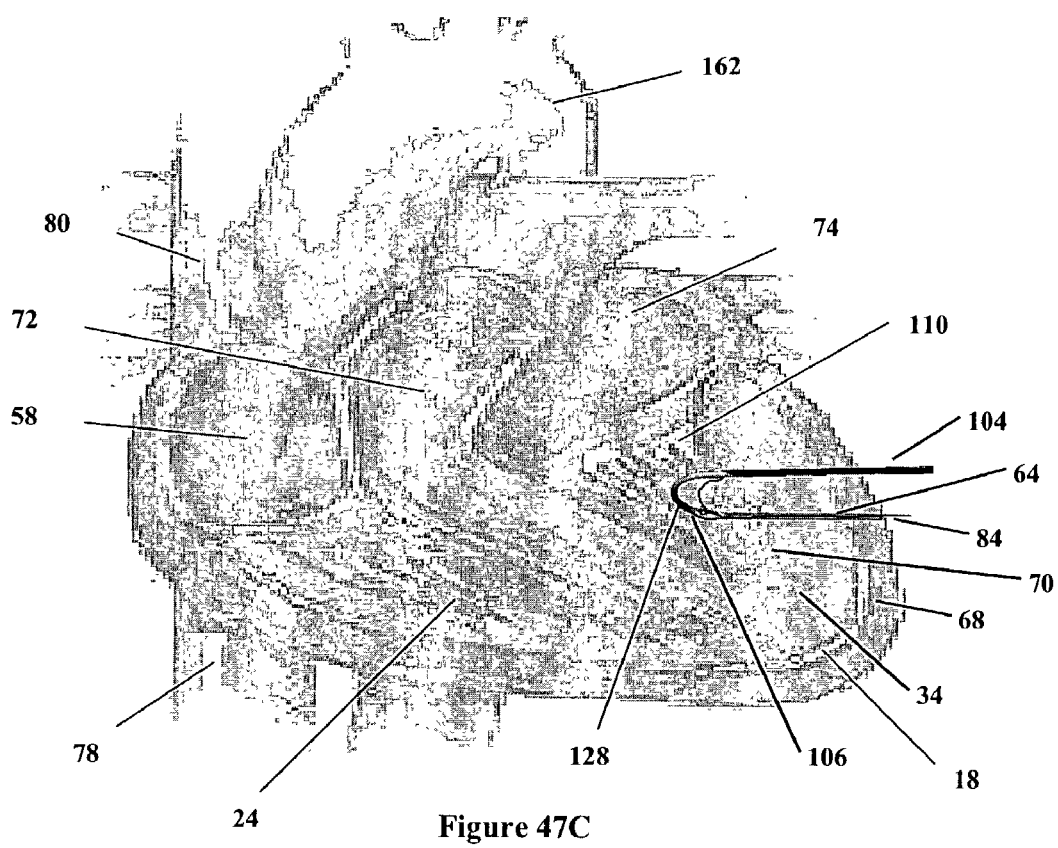
Figure 47D:
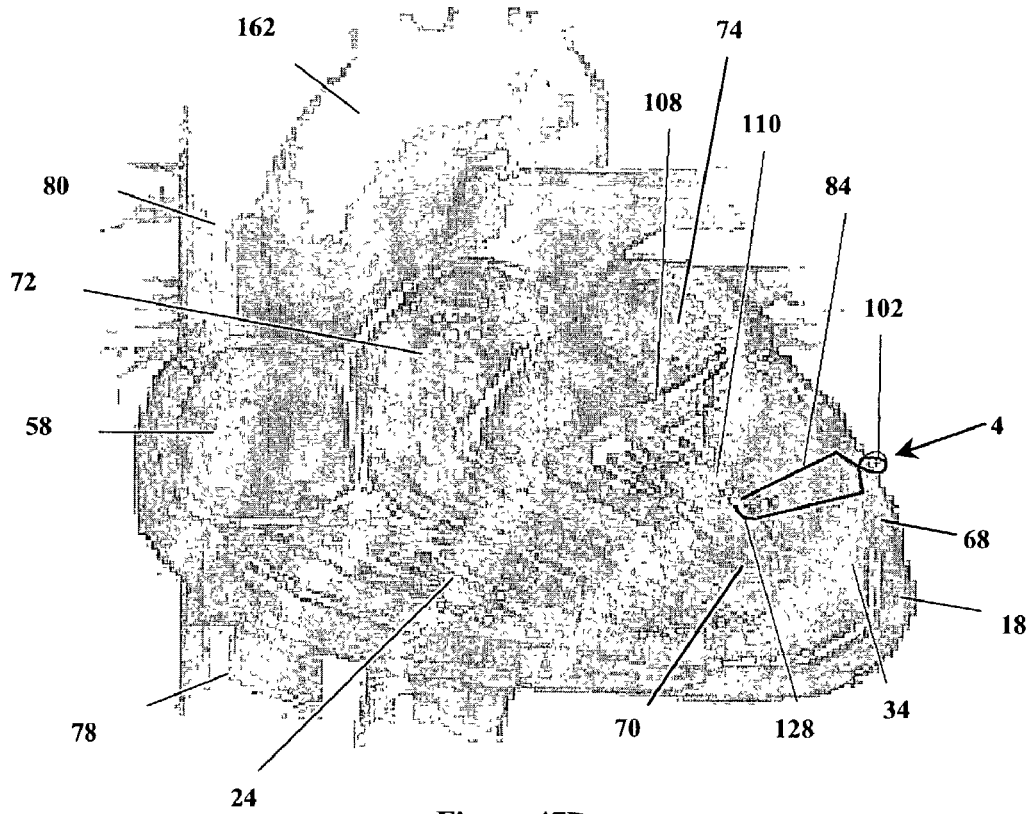

As mentioned before, the tensioning structures of the invention by also be used to apply tension to papillary muscles and/or chordae tendineae to reposition the valve leaflets to reduce/eliminate regurgitation, to limit the motion of the leaflets to improve/restore the function of cardiac valves; and to directly reposition the valve leaflets to prevent prolapse or other abnormalities of the leaflets and to prevent associated deficiencies. In this spirit, FIGS. 47A to 47D show a tensioning structure embodiment and delivery system used to place the tensioning structure from the epicardium through the myocardium, around one or more chordae tendineae or through a papillary muscle, and back through the myocardium where the tensioning structure is anchored such that it applies tension to these sub-valvular structures to reorient the valve leaflets and restrict valve prolapse. FIGS. 47A to 47C show the three-component delivery system from FIGS. 43A to 43D passing one or more tensioning structures through or around the chordae tendineae 110, or through or around a papillary muscle. The delivery system locates the free ends of the tensioning structures through myocardium and external to the endocardium where they can be tied to tighten the tensioning structures. As shown in FIG. 47A, the outer sheath is inserted through the heart wall. The outer sheath can incorporate a beveled tip as shown in FIG. 43A or can be inserted over a trocar, needle, or other penetrating mechanism. The middle sheath is then advanced through the outer sheath as shown in FIG. 47B. In this version, the middle sheath does not require a beveled or sharpened tip and it is preferred that the distal end is atraumatic so the middle sheath does not damage the chordae tendineae as it is advanced through the outer sheath where it is allowed to expand towards its preformed, curved configuration passing around chordae tendineae. If the middle sheath needs to pass through papillary muscles then it would require a beveled or sharpened tip to puncture the papillary muscle. Alternatively, the sheath can incorporate a steering mechanism to manually curve the sheath around the papillary muscle or chordae tendineae instead of relying upon a self-expanding preformed shape. Once positioned, as shown in FIG. 47C, the puncturing device is inserted through the middle sheath and is used to pass the tensioning structure 4 through the middle sheath and back through the endocardium, through the myocardium and past the epicardium where it can be removed from the holder with forceps or other similar instrument. Then as shown in FIG. 47D, the deployment system is removed and the tensioning structure is tightened. The degree of tightening can be guided or adjusted based on Transesophageal Echocardiography, Intracardiac Echocardiography, MRI, Fluoroscopy, CT, or other imaging or visualization modality capable of determining the apposition and movement of the valve leaflets.

Figure 48A:
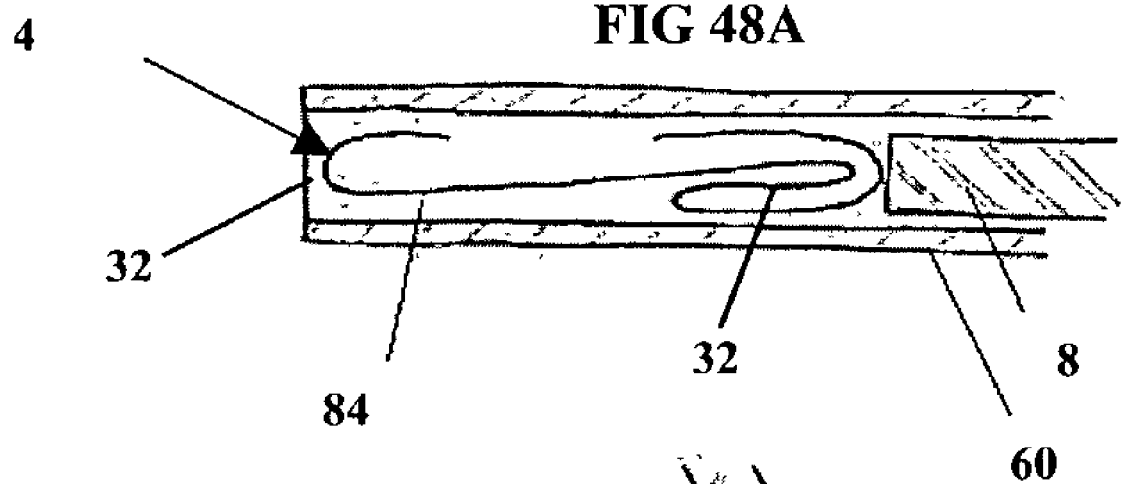
FIG. 48A shows a side-sectional view of another tensioning structure compressed into a low profile within a deployment device for placement inside the heart cavity and attachment to the chordae tendineae and/or papillary muscle.
Figure 48B:
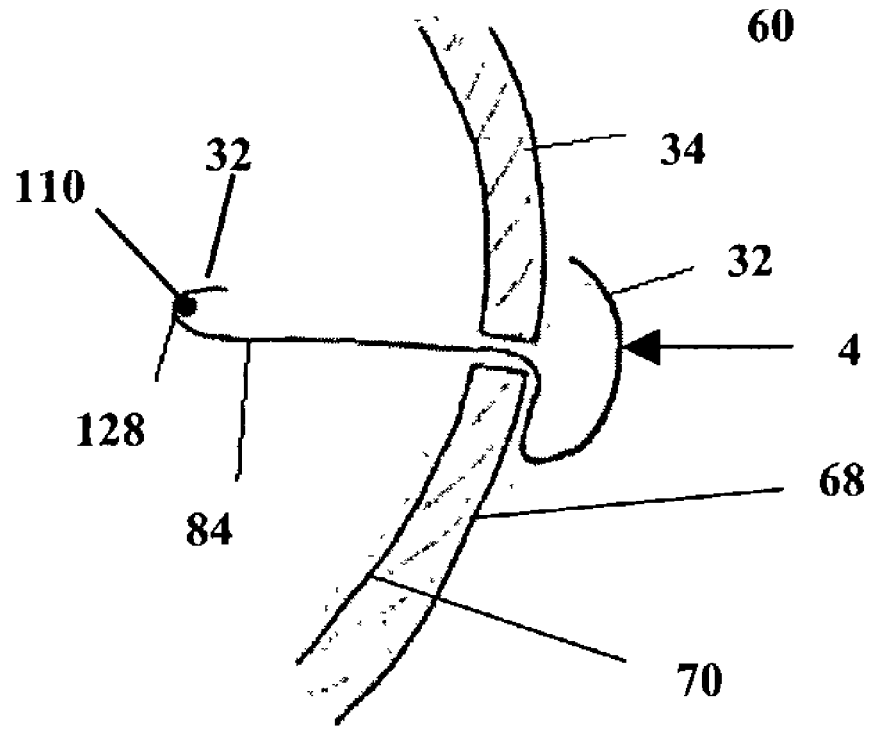
FIG. 48B shows a side-sectional view of the deployed and secured tensioning structure of FIG. 48A.
Figure 49A:
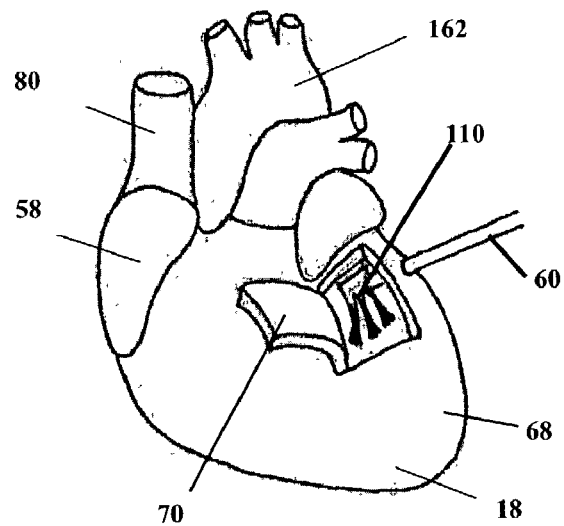
FIGS. 49A and 49B show perspective views of a heart with parts cut-out highlighting the process of deploying and securing a tensioning structure to the chordae tendineae.
Figure 49B:
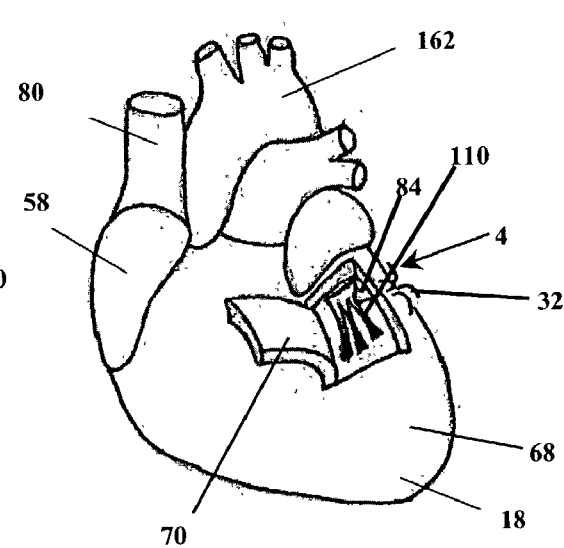
Figure 50A:
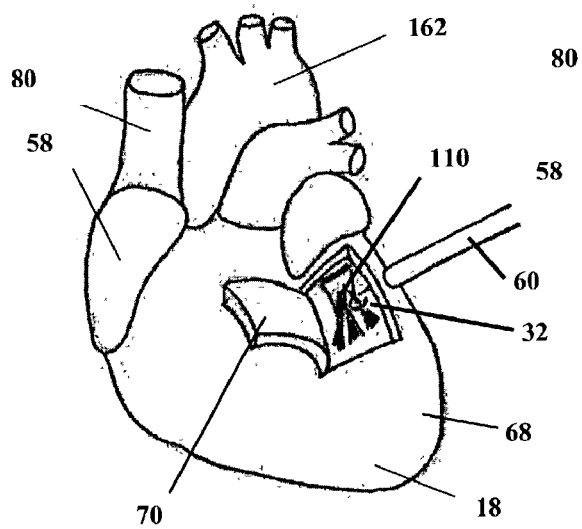
FIGS. 50A and 50B show cut-away perspective views of the heart showing the process of deploying and securing the tensioning structure embodiment of FIGS. 48A and 48B to the chordae tendineae.
Figure 50B:
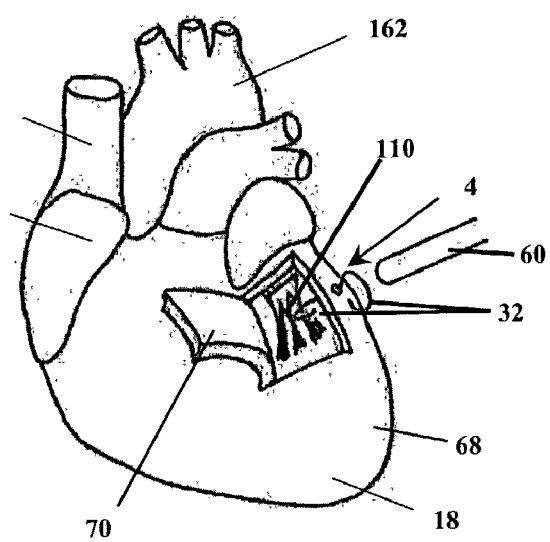

FIGS. 48A and 48B show an alternative tensioning structure and associated delivery system used to engage a chordae tendineac or papillary muscle with one end while the opposite end produces an anchor that is capable of tightening to apply tension to the chordae tendineae or papillary muscles 128. As shown in FIGS. 49A, 49B, 50A and 50B, the distal anchor 32 of the tensioning structure is advanced through the myocardium and is entangled to the chordae tendineae 110 or papillary muscle 128, and the proximal end is then pulled through the epicardial surface and expanded (plastically deformable) or allowed to expand (superelastic) into a preformed, enlarged shape preventing migration of the proximal anchor 32 into the heart cavity. At this point the amount of tension applied to the chordae tendineae or papillary muscle depends on the placement of the proximal anchor and the length of the tensile member 84 between these anchors. The tension can then be altered utilizing a variably tightening mechanism as described above or by relocating the proximal anchor 32 to increase or decrease tension as required.

Figure 51A:
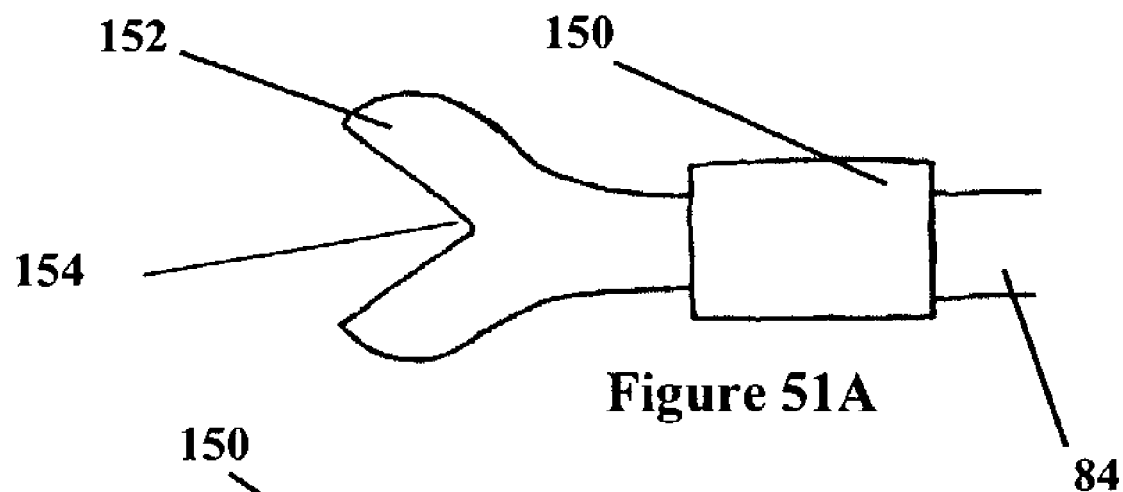
FIGS. 51A and 51B show close-up, side views of the end of a mechanism used to directly grasp, engage and reposition valve leaflets.
Figure 51B:
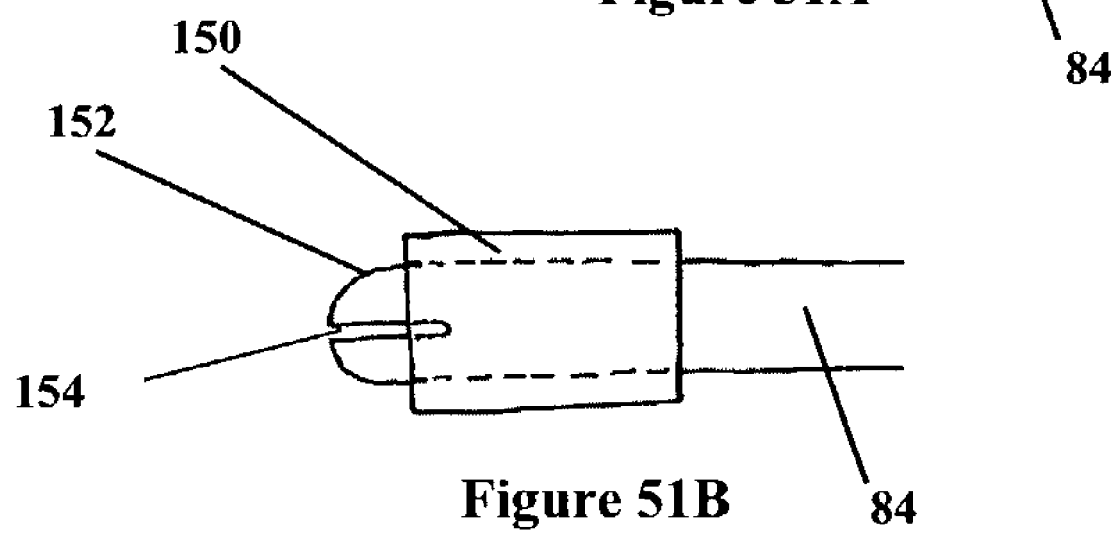

The tensioning structures, such as those shown in FIGS. 45F to 45L, can alternatively be inserted through the valve leaflets as opposed to around or through the papillary muscle or chordae tendineae to directly reposition the valve leaflets by tightening the tensioning structures from the epicardial surface of the heart. In this configuration, a grasping instrument containing a lumen providing passage for the puncturing device can be used to temporarily engage the valve leaflet and provide a path to advance the tensioning structure past the epicardial surface, through the myocardium, up to and through the valve leaflet. Then the anchor is deployed (by balloon expansion or release of a self-expanding anchor) against the valve leaflet thereby attaching the tensile member 84. The proximal end of the tensile member is then retracted past the epicardial surface and the desired amount of tension to reposition or stabilize the valve leaflet is applied based upon real-time assessment/visualization of hemodynamics and anatomic motion. Finally, the proximal end of the tensile member 84 is anchored to the epicardial surface at a suitable location. Alternatively, the delivery system used to engage the valve leaflet can provide a mechanism to grasp the tensile member 84 after insertion of the tensile member through the valve leaflet. Such a mechanism would enable retraction back past the myocardium and epicardium so that the opposite free ends of the tensile member 84 can be tied, tightened and used to manipulate the position of the valve leaflets, thereby defining the tensioning structure. Alternatively, the leaflets may be directly manipulated and repositioned using the mechanism in FIGS. 51A and 51B. This mechanism facilitates grasping and then locking onto the leaflet tissue by engaging the jaw 152 with an anchor cincher tube 150. Furthermore, the mechanism could be attached to a tensile member and anchor to facilitate locating and securing the structure at the desired position to urge valve competency.

Tensioning Structure Materials and General Fabrication Methods

The embodiments of the entire invention described herein can be fabricated from various biological, metallic, and polymeric materials. For self-expanding components of the embodiments, those components are preferably fabricated from a superelastic, shape memory material like nitinol (nickel titanium alloy). These types of materials elastically deform upon exposure to an external force and return to their preformed shape upon reduction or removal of the external force. This elasticity property renders the material as ideal for deployment with vascular conduit target about eccentric, three-dimensional tortuous geometries with limited concern toward fatigue failure and difficulty in placement. Superelastic shape memory alloys also enable straining of the material numerous times without plastic deformation. The repetitive strain capability facilitates a limited systolic stretch to enable adequate cardiac output while limiting or restricting the possibility of over stretch and continuation of the cyclic damage.

Various components of the tensioning structures can be fabricated from shape memory alloys (e.g., nickel titanium) demonstrating stress-induced martensite at ambient temperature. Other shape memory alloys can be used and the superelastic material can alternatively exhibit austenite properties at ambient temperature. The composition of the shape memory alloy is preferably chosen to produce the finish and start martensite transformation-temperatures (Mf and Ms) and the start and finish austenite transformation temperatures (As and Af) depending on the desired material response. When fabricating shape memory alloys that exhibit stress induced martensite the material composition is chosen such that the maximum temperature that the material exhibits stress-induced martensite properties (Md) is greater than Af and the range of temperatures between Af and Md covers the range of ambient temperatures to which the support members are exposed. When fabricating shape memory alloys that exhibit austenite properties and do not transform to martensite in response to stress, the material composition is chosen such that both Af and Md are less than the range of temperatures to which the supports are exposed. Of course, Af and Md can be chosen at any temperatures provided the shape memory alloy exhibits superelastic properties throughout the temperature range to which they are exposed. Nickel titanium having an atomic ratio of 51.2% Ni to 48.8% Ti exhibits an Af of approximately −20° C.; nickel titanium having an atomic ratio of 50% Ni to 50% Ti exhibits an Af of approximately 100° C. [Melzer A, Pelton A. Superelastic Shape-Memory Technology of Nitinol in Medicine. Min Invas Ther & Allied Technol. 2000: 9(2) 59–60].

Such superelastic components are able to withstand strain as high as 10% without plastically deforming. Materials other than superelastic shape memory alloys can replace superelastic materials in appropriate tensioning structure components provided they can be elastically deformed within the temperature, stress, and strain parameters required to maximize the elastic restoring force, thereby enabling the tensioning structures to exert a directional force in response to an induced deflection. Such materials include other shape memory alloys, bulk metallic glasses, amorphous Beryllium, suitable ceramic compositions, spring stainless steel 17-7, Elgiloy™, superelastic polymers, etc.

The tensioning structures are expected to be of limited thrombogenicity and with percutaneous deployment especially in venous structures of the heart, the risk of infarct, adverse cerebral embolic events and other similar ischemic events/injury is severely limited if not avoided. Also, administration of commonly used anti-clotting and anti-platelet pharmacological agents is generally restricted to the implant procedure and not required in an ongoing basis.

The tensioning structures can be fabricated from at least one rod, wire, suture, strand, strip, band, bar, tube, sheet, ribbon or other such raw material having the desired pattern, cross sectional profile, dimensions, or a combination of cross-sections. These raw materials can be formed from various standard means including but not limited to: extrusion, injection molding, press-forging, rotary forging, bar rolling, sheet rolling, cold drawing, cold rolling, using multiple cold working and annealing steps, or casting. When using superelastic materials or other alloys as the tensioning structures, they can be cut into the desired pattern and thermally formed into the desired three-dimensional geometric form. The tensioning structures can then be cut into the desired length, pattern or other geometric form using various means including, but not limited to, conventional abrasive sawing, water jet cutting, laser cutting, EDM machining, photochemical etching or other etching techniques. The addition of holes, slots, notches and other cut away areas on the support structure body facilitates the capability to tailor the stiffness of the implant.

The tensioning structure components, especially those that employ the use of tubular or wire raw materials, can also be further modified via centerless grinding means to enable tensioning structures that are tapered (i.e., have a cross-sectional diameter on the proximal end of the structure that progressively ramps down to a smaller cross-section on the opposite or distal end). Tensioning structure components of this type of geometry are ideally suited for placement in the vascular conduits since said anatomical conduits tend to taper in a similar fashion from the proximal ostia down to distal locations.

The tensioning structure components can be fabricated from a multitude of these individually processed or unprocessed components (rods, wires, bands, bars, tubes, sheets, ribbons, etc.) and joined together using various means including but not limited to the following: laser welding, adhesive bonding, soldering, spot welding, mechanical crimping, swaging and other attachment means to produce composite tensioning structures.

When fabricating superelastic tensioning structure components from tubing, the raw material can have an oval, circular, rectangular, square, trapezoidal, or other cross-sectional geometry capable of being cut into the desired pattern. After cutting the desired pattern, the tensioning structure components are formed into the desired shape, heated, for example, between 300° C. and 600° C., and allowed to cool an the preformed geometry to set the shape of the support members.

When fabricating superelastic tensioning structure components from flat sheets of raw material, the raw material can be configured with at least one width, W, and at least one wall thickness, T, throughout the raw material. As such, the raw sheet material can have a consistent wall thickness, a tapered thickness, or sections of varying thickness. The raw material is then cut into the desired pattern, and thermally shaped into the desired three-dimensional geometry.

Opposite ends or intersections of thermally formed tensioning structure components can be secured by using shrink tubing, applying adhesives, welding, soldering, mechanically engaging, utilizing another bonding means or a combination of these bonding methods. Opposite ends of the thermally formed tensioning structure components can alternatively be free-floating to permit increased flexibility.

Once superelastic tensioning structure components are fabricated and formed into the desired three-dimensional geometry, the supports can be electropolished, tumbled, sand blasted, chemically etched, ground, or otherwise treated to remove any edges and/or produce a smooth surface.

The previous discussions provide description of minimally invasive and percutaneous tensioning structures and delivery devices used to treat degenerative heart disease in patients suffering any stage of congestive heart failure. In addition, the described inventions provide a methods and devices to provide restriction of continued enlargement of the heart, potentially progressively reduce heart size via reverse remodeling (i.e., application of compressive force during both systole and diastole) and finally decrease valvular regurgitation associated with said enlargement.

It will be obvious to those skilled in the art that the support structures described herein can be applied across a broad spectrum of organ structures to provide reinforcement and to limit enlargement facilitated by compensatory physiologic mechanisms.

Though the invention has been described in reference to certain examples, optionally incorporating various features, the invention is not to be limited to the set-ups described. The invention is not limited to the uses noted or by way of the exemplary description provided herein. Numerous modifications and/or additions to the above-described embodiments would be readily apparent to one skilled in the art; it is intended that the scope of the present inventions extend to all such modifications and/or additions. It is to be understood that the breadth of the present invention is to be limited only by the literal or equitable scope of the following claims.

We claim:

1. A method of treating a heart with a venous tree adjacent said heart, said method comprising:
    introducing into said venous tree, a support device comprising a proximal anchor, a distal anchor, and an elongate member adapted to be engaged in tension between said anchors,
    deploying said support device,
    wherein tension is applied between said anchors by said elongate member, and wherein support force output of said device is adjusted during support device deployment.

2. The method of claim 1, wherein said elongate member is tightened after securing said anchors to adjust said force output.

3. The method of claim 1, wherein at least said distal anchor is secured in the coronary sinus of said heart.

4. The method of claim 1, performed percutaneously.

5. The method of claim 1, wherein said elongate member tension is further adjusted post-operatively.

6. The method of claim 1, wherein elongate member flexibility is increased to adjust said force output.

7. The method of claim 6, wherein flexibility is increased by releasing at least one tension spring.

8. The method of claim 1, wherein a detent means is employed to effect said force output adjustment.

9. The method of claim 1, wherein a delivery catheter for said support device includes means for a physician to adjust said support device.

10. The method of claim 1, wherein said distal anchor is positioned and secured in a vessel adjacent said heart.

* * * * *